US012185787B2

(12) United States Patent
Hall et al.

(10) Patent No.: US 12,185,787 B2
(45) Date of Patent: *Jan. 7, 2025

(54) PERSONAL AIR FILTERING DEVICE WITH AUTOMATIC CONTROL OF AIR MOVEMENT

(71) Applicant: Hall Labs LLC, Provo, UT (US)

(72) Inventors: Michael Hall, Provo, UT (US); David R. Hall, Provo, UT (US); Chandler Flinders, Provo, UT (US); Jordan Englund, Provo, UT (US); Jacob Dean, Provo, UT (US); Anthony E. Pullen, Tucson, AZ (US); Jeff Duncan, Tucson, AZ (US)

(73) Assignee: Hall Labs LLC, Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/209,169

(22) Filed: Mar. 22, 2021

(65) Prior Publication Data

US 2021/0289875 A1 Sep. 23, 2021

Related U.S. Application Data

(60) Provisional application No. 63/105,830, filed on Oct. 26, 2020, provisional application No. 63/053,519,
(Continued)

(51) Int. Cl.
*A42B 3/28* (2006.01)
*A41D 13/11* (2006.01)
(Continued)

(52) U.S. Cl.
CPC .......... *A42B 3/286* (2013.01); *A41D 13/1153* (2013.01); *A42B 3/06* (2013.01); *A42B 3/283* (2013.01); *A42B 3/285* (2013.01); *A42B 3/288* (2013.01); *A61F 11/14* (2013.01); *A62B 7/10* (2013.01); *A62B 9/00* (2013.01); *A62B 9/006* (2013.01); *A62B 17/003* (2013.01); *A62B 17/04* (2013.01); *A62B 18/045* (2013.01); *A62B 18/08* (2013.01); *B01D 39/083* (2013.01); *B01D 46/0093* (2013.01); *B01D 46/44* (2013.01); *G02F 1/0126* (2013.01);
(Continued)

(58) Field of Classification Search
CPC .... A42B 3/286; A41D 13/1153; A62B 18/045
See application file for complete search history.

(56) References Cited

U.S. PATENT DOCUMENTS

| | | | | |
|---|---|---|---|---|
| 5,054,480 | A * | 10/1991 | Bare | A41D 13/11 128/206.28 |
| 6,081,929 | A * | 7/2000 | Rothrock | A42B 3/286 2/424 |

(Continued)

*Primary Examiner* — Heather Mangine
*Assistant Examiner* — Erick I Lopez

(57) ABSTRACT

A personal air filtering device comprising a rigid component comprising a transparent face shield, a fabric component, wherein the face shield and fabric combine to cover an entire head of a user and form a seal around the user's neck, an intake port with an inlet filter, an exhaust port with an exhaust filter, an air mover causing filtered air to enter the intake port from outside the device and exhaust air to exit the exhaust port, and a controller configured to adjust the rate at which the air mover moves air.

22 Claims, 35 Drawing Sheets

Related U.S. Application Data filed on Jul. 17, 2020, provisional application No. 62/992,277, filed on Mar. 20, 2020.

(51) Int. Cl.

| | | |
|---|---|---|
| A42B 3/06 | (2006.01) |
| A61F 11/14 | (2006.01) |
| A62B 7/10 | (2006.01) |
| A62B 9/00 | (2006.01) |
| A62B 17/00 | (2006.01) |
| A62B 17/04 | (2006.01) |
| A62B 18/04 | (2006.01) |
| A62B 18/08 | (2006.01) |
| B01D 39/08 | (2006.01) |
| B01D 46/00 | (2022.01) |
| B01D 46/44 | (2006.01) |
| G02F 1/01 | (2006.01) |
| G02F 1/1524 | (2019.01) |

(52) U.S. Cl.
CPC .... *G02F 1/1524* (2019.01); *B01D 2239/0457* (2013.01); *B01D 2273/30* (2013.01)

(56) References Cited

U.S. PATENT DOCUMENTS

| | | | | |
|---|---|---|---|---|
| 6,751,807 | B2* | 6/2004 | Klotz | A42B 3/286 |
| | | | | 2/171.3 |
| 6,990,691 | B2* | 1/2006 | Klotz | A42B 3/286 |
| | | | | 2/901 |
| 8,302,599 | B2* | 11/2012 | Green | A62B 18/045 |
| | | | | 128/201.24 |
| 2015/0096102 | A1* | 4/2015 | Dick | A42B 1/008 |
| | | | | 2/207 |
| 2017/0196281 | A1* | 7/2017 | Rosati | A41D 1/002 |
| 2019/0064750 | A1* | 2/2019 | Awiszus | A62B 9/006 |
| 2019/0175961 | A1* | 6/2019 | Awiszus | A42B 3/0466 |

* cited by examiner

PERSONAL AIR FILTERING DEVICE WITH AUTOMATIC CONTROL OF AIR MOVEMENT

CROSS-REFERENCE TO RELATED APPLICATIONS

This application claims priority to U.S. Provisional Patent Application No. 62/992,277 titled "Head Covering Device" filed on Mar. 20, 2020, U.S. Provisional Patent Application No. 63/053,519 titled "Head Covering Device with Negative Air Flow", U.S. Provisional Patent Application No. 63/053,523 titled "Head Covering Device with Environmental Control", U.S. Provisional Patent Application No. 63/053,526 titled "Head Covering Device with a Communication Component", U.S. Provisional Patent Application No. 63/053,537 titled "Head Covering Device with Automatic Air Moving System", U.S. Provisional Patent Application No. 63/053,542 titled "Head Covering Device with Shroud", U.S. Provisional Patent Application No. 63/053,546 titled "Head Covering Device with Washable Filtering Fabric", U.S. Provisional Patent Application No. 63/053,548 titled "Head Covering Device with Electromagnetic Radiation Filtering Face Shield", U.S. Provisional Patent Application No. 63/053,552 titled "Protective Mask with Negative Air Flow" filed on Jul. 17, 2020, and U.S. Provisional Patent Application No. 63/105,830 titled "Head Covering Device" filed on Oct. 26, 2020, which are incorporated herein by reference in their entirety.

TECHNICAL FIELD

The present disclosure relates to head covering devices.

BACKGROUND

Head covering devices (HCDs) on the market, such as helmets, are typically designed for some type of injury prevention. For example, personal protection equipment (PPE) for the head is commonly construction helmets or welder's helmets. Recreational protective head gear includes motorcycle helmets and sports helmets such as helmets for skiers, bikers, mountain climbers, baseball, and football players. Other types of HCDs include protection equipment such as splash shields and filters for firefighters, policemen, HAZMAT specialists, health care workers, and other first responders. In many cases, the HCDs are heavy, bulky and can be uncomfortable.

SUMMARY

One aspect of the present invention is a personal air filtering device comprising a rigid component comprising a transparent face shield, a fabric component, wherein the face shield and fabric combine to cover an entire head of a user and form a seal around the user's neck, an intake port with an inlet filter, an exhaust port with an exhaust filter, an air mover causing filtered air to enter the intake port from outside the device and exhaust air to exit the exhaust port, and a controller configured to adjust the rate at which the air mover moves air.

In another aspect of the invention, the controller turns the air mover on when the head covering device is placed on the head of the user and turns the air mover off when the head covering device is removed from the head of the user.

In a still further aspect, the device further comprises a sensor for detecting proximity of the user's head.

In a yet still further aspect, the device further comprises a switch comprises a spring loaded lever that is depressed when the head covering device is placed over the head of the user and turns on the air mover.

In another aspect, the device further comprises two or more electrodes and wherein when the electrodes come into contact with the skin of the user, the air mover is turned on. The electrodes may be further located in the fabric component.

In another aspect of the invention, at least a portion of the transparent shield is configured with a hinge to allow the portion to be pivoted away from the user's face, and wherein the air mover is turned off when the portion is so pivoted.

In still another aspect, the device further comprises a sensor for generating signals indicative of at least one of air pressure, ambient temperature, body temperature, skin moisture, blood oxygen saturation, respiration rate and pulse rate, and a processor for processing signals from the sensor and providing instructions to the controller to adjust the rate of the air mover according to predetermined parameters.

In a still further aspect, the device is configured to communicate with an app running on the user's smart device, which app is configured to provide alerts to the user and to allow the user to adjust the rate of the air mover.

In a still yet further aspect, the device further comprises a communication module for receiving signals relating to at least one of air pressure, ambient temperature, body temperature, skin moisture, blood oxygen saturation, respiration rate and pulse rate, and a processor for processing signals from the communication module and providing instructions to the controller to adjust the rate of the air mover according to predetermined parameters.

In another still yet further aspect, the communication module is configured to receive signals from the user's smart device.

In another aspect of the invention, the device is configured to communicate with an app running on the user's smart device, which app is configured to provide alerts to the user and to allow the user to adjust the rate of the air mover.

In still another aspect, the communication module is configured to receive signals from the user's wearable smart device.

In a still further aspect, the device further comprises a sensor for generating signals indicative of the concentration of oxygen, and a processor for processing signals from the sensor and providing instructions to the controller to increase the rate of the air mover when the oxygen concentration of oxygen falls below a predetermined level. The device may further comprise a user warning system, configured to alert the user when the concentration of oxygen falls below the predetermined level.

In a yet still further aspect, the device further comprises a sensor for generating signals indicative of the concentration of carbon dioxide, and a processor for processing signals from the sensor and providing instructions to the controller to increase the rate of the air mover when the concentration of carbon dioxide rises above a predetermined level. The device may further comprise a user warning system, configured to alert the user when the concentration of carbon dioxide rises above the predetermined level.

In another aspect of the invention, the device further comprises a second sensor for generating signals indicative of the concentration of oxygen, and wherein the processor processes signals from the sensor and the second sensor and provides instructions to increase the rate of the air mover when either the concentration of carbon dioxide rises above a predetermined level or the concentration of oxygen falls below a second predetermined level.

In a still further aspect, the device further comprises a privacy shroud to cover the device to provide a more comfortable sleeping environment for the user. The device may be configured to detect when the privacy shroud is placed over the device and increase the rate of the air mover in response thereto.

Further aspects and embodiments are provided in the following drawings, detailed description, and claims. Unless specified otherwise, the features as described herein are combinable and all such combinations are within the scope of this disclosure.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Overview

Figure 1:
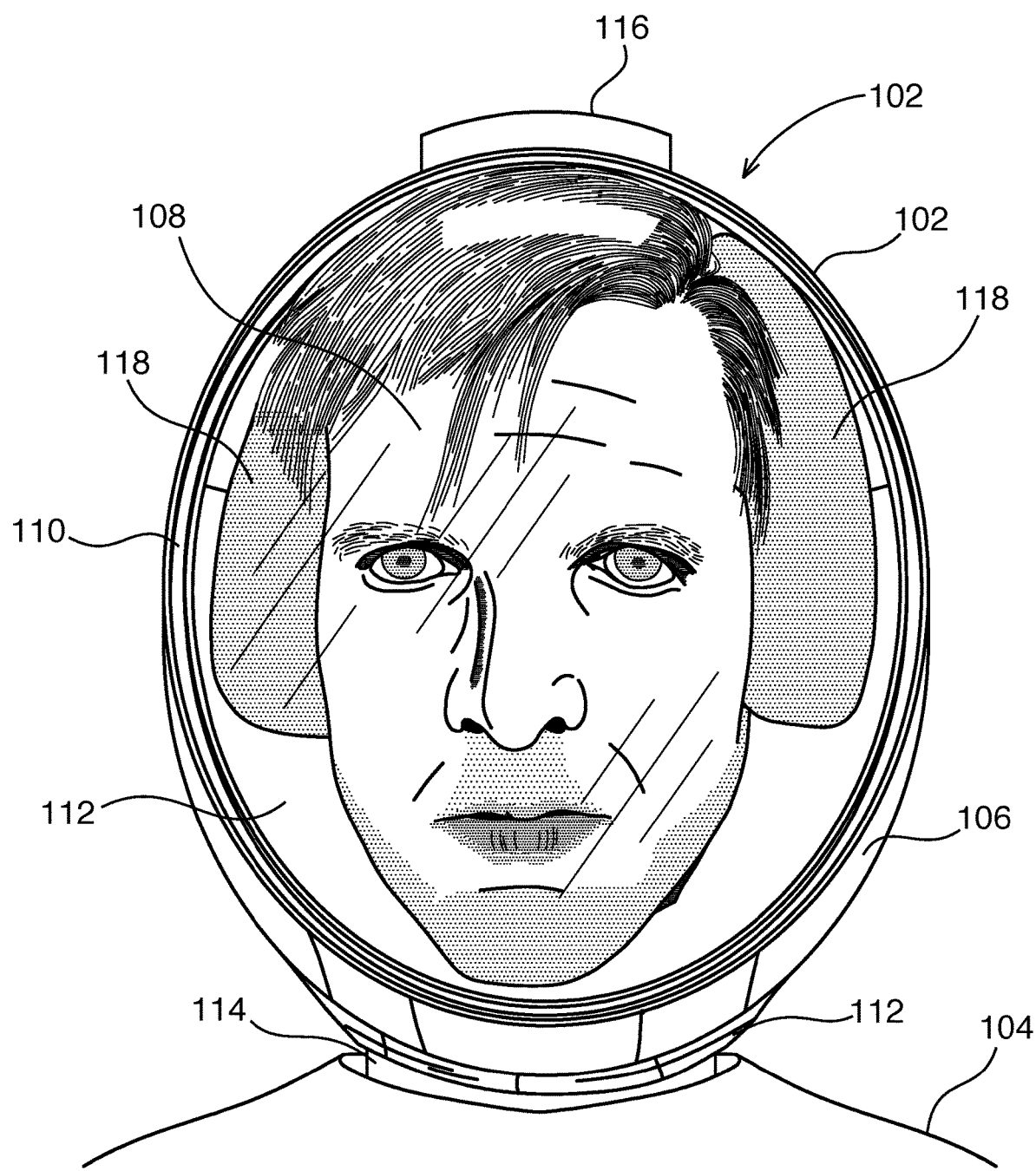
FIG. 1 is a front view of a user wearing a head covering device (HCD), according to an embodiment of the disclosure.

Embodiments of methods, materials and processes described herein are directed towards head covering devices.

Head covering devices, also referred to as personal protection headwear, can be used to provide a filtered air environment to a user to prevent a user from being infected with a contagious disease. Head covering devices may also filter the exhaust air to prevent a user from spreading a contagious disease.

Head covering devices disclosed herein include a rigid component and a flexible component combined to completely cover the head of a user. The rigid component includes a frame and a transparent face shield. The flexible component includes a fabric that seals around the neck of a user. The disclosure herein describes various designs and components including air movers to.

Definitions

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, the term "user" refers to any individual who uses an HCD.

As used herein, the term "filter," as a noun, refers to a device, typically composed of fibrous or porous materials which removes unwanted components, usually in the form of particulates, such as dust, pollen, mold, viruses, and bacteria, from air. Filters containing an adsorbent or catalyst, such as charcoal (carbon), may also remove odors and gaseous pollutants such as volatile organic compounds or ozone. Air filters are generally used in applications where air quality is important. As a verb, "filter" refers to the act of removing particles from air.

As used herein, the term "transparent" is used in its normal sense, that is the property of allowing light to pass through so that behind can be distinctly seen therethrough. The transparent components described and defined below are preferably clear, but may be tinted, in whole or in part.

The term "negative air flow" is used to indicate that, in accordance with embodiments of the invention, air is actively pulled inside the HCD through an intake filter by an air mover and the air is exhausted out an exhaust filter.

The term "positive air flow" is used to indicate that, in accordance with embodiments of the invention, air is actively pulled inside the HCD by an air mover through an intake filter in the air mover and exhausted through an exhaust filter.

The term "neutral air flow" is used to indicate that, in accordance with embodiments of the invention, a substantially static flow of air is maintained in the HCD. The air flow into and out of the HCD is controlled by the breathing in and breathing out of the user.

As used herein, the term "electrochromic" is where optical properties such as optical transmission, absorption, reflectance and/or emittance can be controlled in a reversible manner upon, application of an electrical energy, such as a voltage bias.

As used herein, the term "augmented reality" (AR) refers an interactive experience of a real-world environment where the objects that reside in the real world are enhanced by computer-generated perceptual information, sometimes across multiple sensory modalities, including visual, auditory, haptic, somatosensory and olfactory. AR can be defined as a system that fulfills three basic features: a combination of real and virtual worlds, real-time interaction, and accurate 3D registration of virtual and real objects.

As used herein, the term "hook-and-loop fastener" which is commonly referred to as "Velcro" refers to two components: typically, two lineal fabric strips (or, alternatively, round "dots" or squares) which are attached (sewn or otherwise adhered) to the opposing surfaces to be fastened. The first component features tiny hooks, the second features smaller loops. When the two are pressed together the hooks catch in the loops and the two pieces fasten or bind temporarily. When separated, by pulling or peeling the two surfaces apart, the strips make a distinctive "ripping" sound.

As used herein, the term "proximity sensor" refers to a sensor that is able to detect the presence of nearby objects without any physical contact. A proximity sensor often emits an electromagnetic field or a beam of electromagnetic radiation (infrared, for instance), and looks for changes in the field or return signal. The object being sensed is often referred to as the proximity sensor's target. Different proximity sensor targets demand different sensors. For example, a capacitive proximity sensor or photoelectric sensor might be suitable for a plastic target; an inductive proximity sensor always requires a metal target. Other types of proximity sensors include capacitive displacement sensor, Doppler effect sensor, magnetic sensor, reflective sensor, photoelectric sensor, laser rangefinder sensor, thermal infrared sensor, radar sensor, ionizing radiation sensor, ultrasonic sensor, fiber optics sensor, or a Hall effect sensor.

As used herein, the term "QR (quick response) code" refers to a type of matrix barcode (or two-dimensional barcode) first designed in 1994 for the automotive industry in Japan. A barcode is a machine-readable optical label that contains information about the item to which it is attached. In practice, QR codes often contain data for a locator, identifier, or tracker that points to a website or application. A QR code uses four standardized encoding modes (numeric, alphanumeric, byte/binary, and kanji) to store data efficiently; extensions may also be used. A QR code consists of black squares arranged in a square grid on a white background, which can be read by an imaging device such as a camera and processed using Reed-Solomon error correction until the image can be appropriately interpreted. The required data is then extracted from patterns that are present in both horizontal and vertical components of the image.

As used herein, the term "occupational noise" refers to the amount of acoustic energy received by an employee's auditory system when they are working in the industry. Occupational noise, or industrial noise, is often a term used in occupational safety and health, as sustained exposure can cause permanent hearing damage. Occupational noise is considered an occupational hazard traditionally linked to loud industries such as ship-building, mining, railroad work, welding, and construction, but can be present in any workplace where hazardous noise is present.

EXEMPLARY EMBODIMENTS

The present disclosure relates to HCDs and other mouth and nose-covering devices to provide a controlled and comfortable environment to a user. Users may need a controlled environment due to various health-related reasons such as to protect those with respiratory ailments, compromised immune systems, advanced age, from airborne contagion. The same protection may also be needed for the protection of health care providers. Alternatively, such devices may be desirable to use in harsh environments, such as extreme cold or heat, or environments with high levels of suspended particulate, such as dust. Still further, such devices may also be desirable to protect the user from harsh noise environments. The present disclosure illustrates embodiments of HCDs and masks that include filtering fabric and an air mover.

In various exemplary embodiments, the HCD includes an air intake filter fabric component (FFC) designed to provide clean air to a user. Fabric located in the neck and head area may act as an air intake filter. Exhaled air from a user may be exhausted through an exhaust port. An air mover pulls the air from inside the HCD and exhausts it to the environment. The exhaust air is filtered in instances where the user is infected with a disease but wishes to go out in public.

In various exemplary embodiments, an HCD includes a fabric component where a portion of the fabric is permeable to air and a portion that is impermeable to air. An air mover can pull air from inside the HCD and exhausts it to the environment, pull air from outside the HCD to inside the HCD and exhaust it to the environment, or maintain a neutral air flow as desired by a user. The air passes through an inlet port to enter the HCD and an outlet port to exit the HCD that is spanned by a filter cartridge assembly comprising an air filter.

In various exemplary embodiments, the HCD includes a rigid component and fabric component that when combined, completely cover the head of a user and seals around the neck of the user. In various exemplary embodiments, the fabric component comprises a portion that is permeable to air and a portion that is impermeable to air. An air mover can pull air from inside the HCD and exhausts it to the environment, pull air from outside the HCD to inside the HCD and exhaust it to the environment, or maintain a neutral air flow as desired by a user. The air that passes through an inlet port to enter the HCD is filtered and an outlet port to exhaust air is also filtered.

In various exemplary embodiments, the HCD includes an automatic air mover. The automatic air mover turns on when the HCD is placed on the head of a user and turns off when it is removed. The automatic air mover increases or decrease the flow rate based on the conditions of the environment inside of the HCD.

Head Covering Device (HCD) with Filtering Fabric

The following embodiments relate to a HCD with filtered air and capable of negative, positive, or neutral air flow mode to provide a comfortable and controlled environment for a user. The HCD comprises a fabric component that can filter coming into or out of the device.

The term "negative air flow" is used to indicate that, in accordance with embodiments of the invention, air is actively exhausted from inside the HCD by the air mover. The negative flow" thus created by the active exhaust serves to draw air into the HCD through the FFC. As a result of this design, the intake air can be drawn into the device from a large surface. Consequently, the intake air can be a gentler stream of air, as compared to the stream of air if an air mover were pushing the intake air into the device. This gentler stream is believed to improve the comfort of the preferred embodiments of the invention.

The HCD may also be capable of "positive air flow" wherein air is actively drawn into the device through an inlet filter by an air mover and exhausted through the FFC. The HCD may also be capable of "neutral air flow" wherein air is drawn into and out of the device through the breathing of the user.

FIG. 1 is a front view of a user 104 wearing a head covering device (HCD) 102, according to an embodiment of the disclosure. An HCD 102 is placed over the head of a user 104. HCD 102 comprises a frame 106 and a transparent face shield 108. Frame 106 may be constructed from a rigid or semi-rigid material. Frame 106 is a hoop-like structure wherein the perimeter of the frame has a generally oval shape but may also be generally circular or some other appropriate shape, such as pear-shaped. Frame 106 comprises a channel 110. The edge of the face shield 108 may be placed in and sit in the channel 110.

Frame 106 may be constructed from a polymer or metal or a combination thereof. The polymer may comprise fiberglass, carbon fiber, graphene, polyamide, polycarbonate (PC), polyester, high density or low density polyethylene, polyethylene terephthalate (PET), polypropylene (PP), polystyrene (PS), polyurethane, polyvinyl chloride (PVC), polyvinylidene chloride, acrylonitrile butadiene styrene (ABS), polymethylmethacrylate (PMMA), polytetrafluoroethylene (PTFE), phenolic, polyetheretherketone (PEEK), maleimide, bismaleimide, polyetherimide, polyimide, plastarch, furan, silicone, polysulfone, rubber, or a combination thereof. The frame may have a generally oval shape and circles a user's head, with a lower half passing below the user's chin and an upper half passing above a user's forehead.

In a preferred embodiment, face shield 108 is shaped as a hemi-ellipsoid. The shield comprises a transparent polymer or glass. The polymer may comprise an acrylic such as polymethylmethacrylate. The polymer may comprise polystyrene (PS), polycarbonate, glycol modified polyethylene terephthalate (PETG), or cellulose acetate butyrate or a combination thereof. In some embodiments, the face shield is made from a laminate of polymeric films, each contributing to the structural or optical properties of the face shield. As an example, one layer of the laminate may be included to provide shatter resistance.

The face shield is preferably set close enough to the face of a user where the user's eyes are unable to focus on the inner surface of the face shield, and thus not interfere with the vision of the user. In some embodiments, the inner surface of the face shield is not set close enough where the eyes are unable to focus on the inner surface of the face shield. Face shield 108 may be permanently attached to the frame 106 or may be detachable from the frame. If permanently attached, this may be accomplished by using an adhesive, thermal welding, or some other means. If detachable, the face shield may be held securely to the frame using an attaching device, such as a hook and loop fastener (Velcro®), clamps, clasps, magnets, screws, or other means.

The face shield may have a thickness in the range of about 0.05-0.25 inches. In the depicted embodiment, the face shield 108 has a thickness of about 0.125 inches. The face shield may be constructed from materials that are approved for impact resistance by the American National Standards Institute (ANSI). The face shield may be double-walled, preferably with a vacuum therebetween, for extra insulation. The face shield may comprise a scratch resistant coating or layer on the inner and/or outer surface. The face shield may comprise an anti-fogging coating on the inner or outer surface. A replaceable protective layer may be placed over the outer surface of the face shield. Naturally, the replaceable protective layer should comprise a transparent polymer.

A top portion of the transparent face shield may extend above a user's eyes, a bottom portion extends below the user's mouth and a first and second side portion extend beyond the user's side peripheral vision. The top portion of face shield may extend above a user's forehead and the bottom portion extends below the user's chin.

FIG. 1 also illustrates a view of a filtering fabric component (FFC) 112. The FFC 112 may also be referred to as a neck skirt, neck seal, neck collar, or neck shroud. FFC 112 preferably fits snugly around the neck 112 of a user 104, such that particulates do not able to pass between the FFC and the neck of the user. FFC may be flexible or stretchable and may be made of a polymer such as polyester, polypropylene, polytetrafluorethylene (PTFE), polyether ether ketone (PEEK), polyethene-co-chlorotrifluoroethene (E-CTFE), silicone, rayon, spandex, lycra, viscose, or nylon. FFC may be made of a natural fabric such as cotton or wool. FFC may be a composite of a natural fabric and a polymer. FFC may comprise a pharmaceutical grade textile.

Preferably, the FFC filters the replacement air entering the HCD 102 so that the filtering blocks at least 95% of particles 0.3 microns or larger (N95) or at least 99% of particles 0.3 microns or larger (N99) or at least 99.97% of particles 0.3 microns or larger (N100). While N95 may be most comfortable for a mask wearer, who is required to draw fresh air in and expel air out by normal breathing activity; higher levels of filtration may be obtained by the inventive devices because the exhaust and the drawing fresh air in are aided by the fan(s).

As depicted, the FFC 112 is comprised of a single piece or sheet of filtering fabric. The single sheet of filtering fabric, together with the transparent face shield and the frame, cover a user's entire head and a lower portion of the single sheet of filtering fabric encircles the user's neck and forms a seal therewith. FFC may comprise a drawstring to tighten around the neck of a user for better sealing properties. The single sheet of filtering fabric may possess enough stretch to allow the device to be placed over the user's head while leaving the lower portion of the single sheet of filtering fabric intact and still capable of forming a seal around the user's neck.

Alternatively, the lower portion of the single sheet of filtering fabric may comprise a slit to allow the device to be placed over the user's head. In this embodiment, the lower portion further comprises a closure to close the slit and form the seal around the user's neck. That closure may be effected by a hook and loop fastener®, a zipper, snaps, buttons or any other means of closing the slit. When the zipper is unzipped, allows the device to be fit over the user's head, and when zipped facilitates the fabric component forming a seal around the user's neck.

In some embodiments, the FFC may comprise two types of fabric, whereby only a portion of the fabric allows air to pass through. In other embodiments, the fabric is the same, but some of the fabric is coated to make it impermeable to air. In this way, air flow through some of the FFC, but through not all of it. In yet other embodiments, the fabric may be impermeable to air flow and filter sections are incorporated into the FFC. In these embodiments, less than 50% of the FFC allows air to pass through while the remaining balance of the FFC is impermeable to air flow. In other embodiments, less than 50% of the FFC 112 is impermeable to air flow while the remaining balance of the FFC allows air to pass through.

In yet other embodiments, the FFC is equipped with filtering components that are held in place by the fabric part of the FFC. Such filtering components are preferably made of a porous filter medium. Alternatively, the filtering components use or are combined with other air filtering methods, such as electrostatic filtering or water filtering.

In some embodiments, the length of the FFC may be extended in some instances to cover the area for those users who have a tracheotomy or have a tracheotomy tube. The fabric may have a port to allow for a tracheotomy tube to pass through. The port may have an elastomeric ring to form a seal around the tube.

In some embodiments, the FFC may extend to the base of the neck and rest on the shoulders of the user. The FFC may be a stiff fabric to help provide support for the user. In other embodiments, shoulder supports may extend from the frame of the HCD to the shoulders.

In some embodiments, the FFC may comprise a frontal fabric seal located in front of the neck region of the user below the bottom of the frame. Such a frontal fabric may be designed to be impermeable to an air flow. This provides additional protection of a user, such as a health care working with a person, such as a patient, who is coughing or sneezing.

In other embodiments, a separate frontal fabric may be attached to the FFC near the bottom of the frame in front of the neck region of the user. The bottom of the frontal fabric may or may not be attached to the bottom of the FFC. The frontal fabric may act like an apron, i.e. blocking particles exhaled by someone directly in front of the user. This embodiment may be particularly useful for healthcare workers, attending to patients who are coughing or sneezing. Such an apron may be convenient to take off and clean. Alternatively, the apron may be disposable, such as a paper-based tissue.

In some embodiments, the FFC may comprise a small foam block or insert that a user can use to scratch their noses without having to remove the HCD. The foam block or insert may be mounted on the face shield or on the frame. In other embodiments, the FFC comprises finger sockets that protrude into the facial area of the HCD 102. Finger sockets allow a user to insert their fingers without compromising the environment inside the HCD but yet allow the user to scratch or rub an itch. The FFC may be baggy and stretchable enough for a user to scratch their nose or dab their face without breaking the seal around the user's neck.

In some embodiments, the FFC may comprise two or more layers of fabric and wherein an ultra-violet (UV) light emitting diode (LED) may be placed between the two or more layers of fabric. The UV-LED is to disinfect the air that enters the device. In a preferred embodiment, the UV LED is a UV-C emitting LED that emits light with a wavelength in the range of about 200-280 nm.

In yet other embodiments, the HCD may be equipped with at least one UV source that is directed at the inside of the FFC, so as to disinfect the inside surface of the FFC and the air that passes through it before being inhaled by the user.

Figure 5:
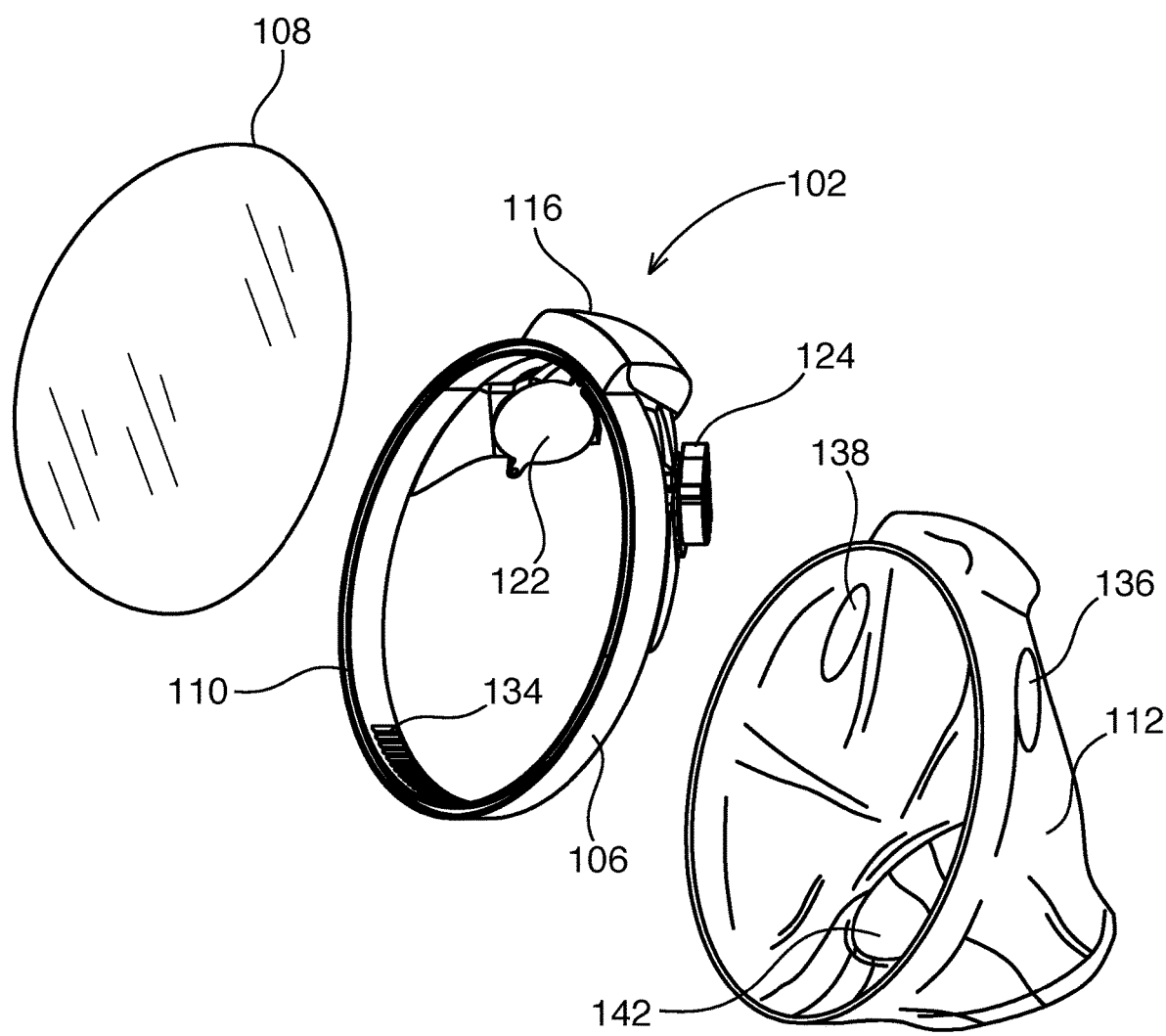
FIG. 5 illustrates an exploded view of an HCD, according to an embodiment of the disclosure.

Referring to the embodiment depicted in FIG. 5, FFC 112 also attaches to the frame 106 to form a seal. The FFC 112 may be stretched over the frame 106 and channel 110 and held in place by inserting of the face shield 108 in the channel 110 to pinch the FFC 112 in place. Alternatively, the transparent face shield may be attached to one side of the frame 108 and the FFC is attached to another side of the frame, such as in a channel parallel to the channel the face shield is attached in.

Further illustrated in FIG. 1 is a view of a compartment 116. Compartment 116 may be used for storage.

Also shown in HCD in FIG. 1 are earpieces 118 to reduce noise, and dampen sound, and reverberations inside of the HCD 102. This may be necessary when the user 104 speaks or from an audio device inside the HCD. The earpieces or noise reduction devices 118 are preferably placed in front of each ear of the user. Testing has shown that using such noise reduction devices prevents undesirable audio properties, i.e. where the user's voice sounds to the user like he is in a bubble. The noise dampening device may comprise sound blocking panels situated between each ear of the user and the mouth of the user.

The earpieces or noise reduction devices 118 are mounted to the face shield 108 but may also be mounted elsewhere such as on the frame or FFC. The noise absorbing devices may be made of a noise and vibration absorbing material such as a polymeric foam, rubber, or cloth. The noise reduction devices may be permanently adhered to the face shield or frame or may be adhered using a hook and loop fastener or other detachable mechanism. The noise reduction devices 118 may be removable, replaceable, and washable.

The earpieces may also serve the purpose of keeping the HCD centered laterally on the user's head. In other words, the earpieces may provide soft buffers between the user's head and the inside surfaces of the HCD. In some embodiments, it is preferred to provide multiple sizes of earpieces, which can be removably attached inside the HCD, in order to accommodate different sizes of users' heads.

Figure 2:
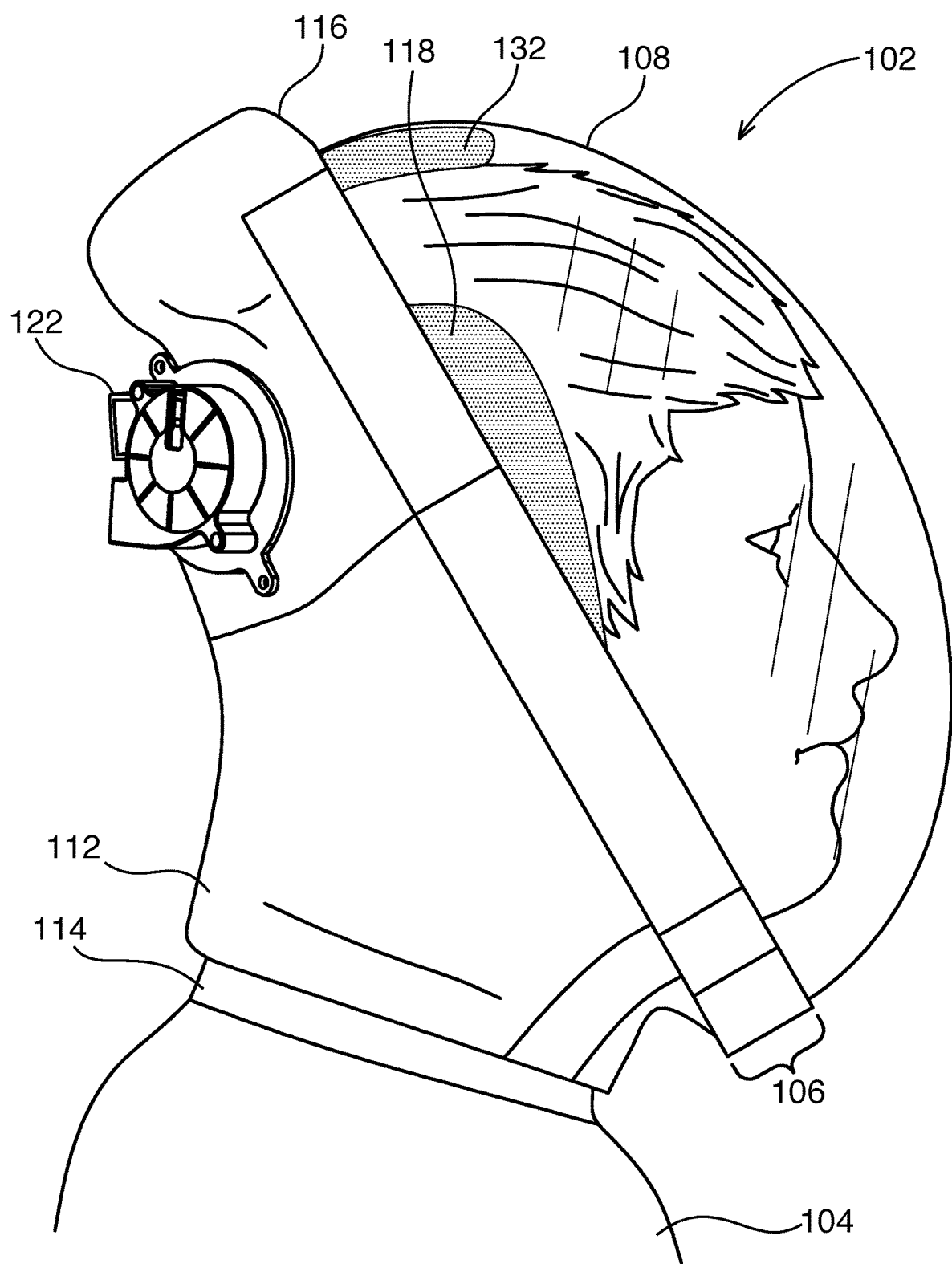
FIG. 2 is a side view of a user wearing an HCD, according to an embodiment of the disclosure.

FIG. 2 is a side view of a user 104 wearing an HCD 102, according to an embodiment of the disclosure. FIG. 2 further illustrates another view of FFC 112. FFC seals around the frame 106 and around the neck area 114 of a user 104. The HCD 102 rests on top of the head of the user. A resting pad 132 is placed at the top of face shield 108 that provides support and cushion between the HCD 102 and the head of the user. The resting pad may comprise a cushion-like material such as cloth, foam, rubber, or other soft material and may be replaceable and washable. As with the earpieces, it may be preferred to provide multiple sizes and/or shapes of removable resting pads, so that the user can select the most comfortable one for his size and shape of head.

FIG. 2 further illustrates an air mover 122 to move air from inside to outside the HCD 102. The air exhausted from inside the HCD is replaced by air outside the device. In this depicted embodiment, the air mover 122 is a fan. The battery pack to supply power for the fan is stored in compartment 116. The fan may be an axial or radial centrifugal fan. The HCD may comprise one or more additional fans. The fan is preferably attached to the housing with a resilient mount, such as foam, cloth, silicone, or a combination thereof, to reduce noise and vibration. The battery pack preferably comprises rechargeable batteries. The batteries may be charged by a cord connected to a wall outlet or by a solar cell. Preferably, a solar cell is mounted to the HCD. The solar cell may provide about 2-6 W of power. In a preferred embodiment, the solar cell may be about 6×6 in$^2$ and provide about 5 W of power to recharge the battery and thus power the components of the HCD.

FIG. 2 also illustrates the hemi-ellipsoid shape of the face shield 108. The hemi-ellipsoid shape allows for more uniform air flow around the face of the user in the HCD 102. The face shield may have a longitudinal length in the range of about 10-15 inches, a width in the range of about 8-11 inches and a height in the range of about 3-6 inches. In an exemplary embodiment, the face shield has a longitudinal length of about 13 inches, a width of about 9 inches and a height of about 4.5 inches. The face shield may be detachable from the frame or may be of unitary construction with the frame. The face shield may form an airtight seal with the frame. A polymer gasket, such as a rubber gasket or an O-ring may be located in between the face shield and frame in channel. The face shield may be double-walled for extra insulation. A vacuum may be located between the double walls.

Figure 3:
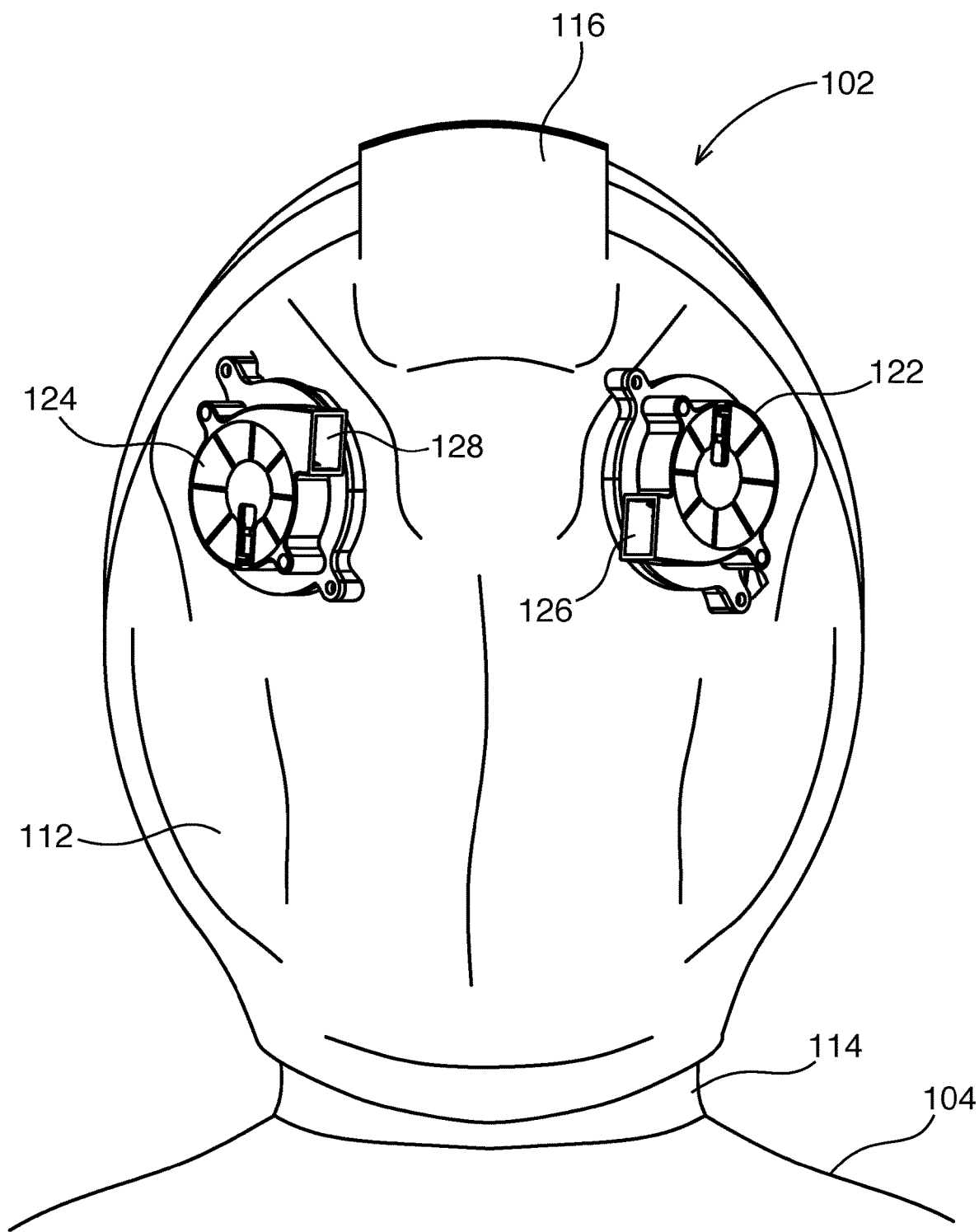
FIG. 3 is a rear view of a user wearing an HCD, according to an embodiment of the disclosure.

FIG. 3 is a rear view of a user 104 wearing an HCD 102, according to an embodiment of the disclosure. FIG. 3 further illustrates how FFC 112 drapes down to the bottom of the neck and forms a seal therearound, although other lengths and designs are possible. For example, the FFC may extend to and rest on the shoulders of the user. In other embodiments, the FFC may extend down the back of the user below the shoulders.

FIG. 3 further shows a second fan unit 124. Both fan units are mounted into the frame 106. The FFC 112 comprises openings wherein the fans 122, 124 pass through when placing the FFC on the frame. In other embodiments, the fans may only be attached to the FFC.

FIG. 3 further illustrates the air exhaust port 126 of the first fan 122 and the air exhaust port 128 of the second fan 124. The exhaust ports exit air to the environment. The fans may be operated in parallel or series mode. The fans 122, 124 are arranged on each side of the FFC in FIG. 3 but may be arranged in other ways. For example, one fan may be placed at the top of the FFC while a second fan may be arranged directly below the first fan such as near the base of the FFC. In a preferred embodiment, the fans are arranged in a manner such that it provides balanced weight to the HCD 102.

The one or more fans may be powered by a battery, such as a rechargeable lithium ion battery, nickel cadmium battery, or a nickel metal hydride battery. The batteries may be located near the top of the rigid frame. The fans may be powered by a solar cell and where the solar cell may be mounted in the HCD. The fans may be removable to replace the batteries or if the fan is damaged, breaks down, loses efficiency, etc. The fans may be dual speed or other variable speed fans. The speed may be controlled by the user of the HCD. The fans may be capable of delivering more than about 1 cfm of air. The fans may be capable of delivering about 1-10 cfm of air. The fans may run intermittently with feedback to deliver a desired amount of air to the user and to keep the air fresh inside the HCD. The HCD may comprise an air flow sensor or an air pressure sensor to monitor air flow and pressure within the HCD.

Figure 4:
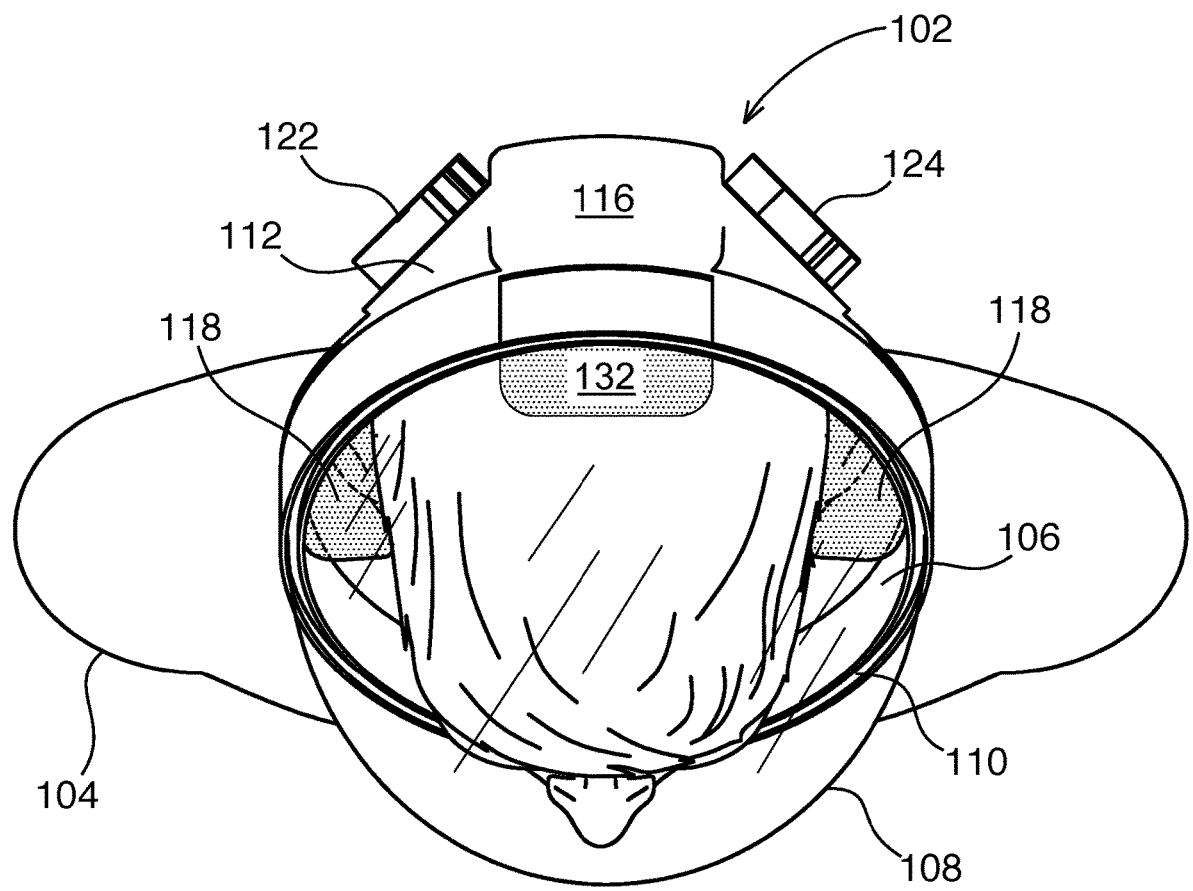
FIG. 4 is an overhead view of a user 104 wearing an HCD 102, according to an embodiment of the disclosure.

FIG. 4 is an overhead view of a user 104 wearing an HCD 102, according to an embodiment of the disclosure. FIG. 4 further illustrates how the HCD is arranged on the head of a user with the resting pad 132. FIG. 4 further illustrates how the frame 106 comprises a channel 110. The face shield 108 sits in the channel. In some embodiments, the FFC may also be stretched over the same channel as the face shield, followed by inserting the face shield on top of the FFC and into the channel to assemble the HCD. An attaching mechanism may then be used to secure the parts of the HCD together. The attaching mechanism may be clips, screws, hook and loop fasteners, magnets, or another device.

In other embodiments, the face shield fits into one channel and the FFC fits into a second channel on the other side of the frame. The face shield can be held in its channel by similar means to those described above. The FFC can be held in its channel by any of those same means.

FIG. 5 is an exploded view of an HCD 102, according to an embodiment of the disclosure. FIG. 5 further illustrates the three primary components of the HCD. FIG. 5 shows further how the fans 122, 124 are mounted to the frame 106 along with compartment 116 which contains the battery pack to provide power to the fans. The compartment is covered by the FFC 112 and can be accessed when the FFC is removed from the frame. In other embodiments, the FFC may comprise an opening to access the compartment when the HCD is assembled. The opening may be a flap that can be opened and shut. The flap may be closed and secured with a zipper, hook and loop fastener, or other means.

Preferably, the frame 106 comprises two exhaust channels, one on each side of the frame. Air is drawn into each exhaust channel, through air intake 134, by the negative pressure created by the fan and then out the exhaust port. Intake 134 is located at the bottom of the frame near the mouth area of a user. The intake may be a single opening (such as a slit) or a plurality of openings aligned in parallel as illustrated in FIG. 5. Intakes may be any shape or size that allows the proper air flow. Through the exhaust channels, the intakes 134 are in fluidic communication with fans 122, 124 and exhaust ports 126, 128 (see FIG. 3).

In some embodiments, such as where the fans are located within the exhaust channels, the ends of the exhaust channels form the exhaust ports. In other embodiments, such as where the fans are outside the exhaust channels, the air exits the exhaust channels and is drawn through the fans and then out a separate exhaust port.

The exploded view of FIG. 5 further illustrates the FFC 112. The FFC comprises openings 136 and 138 for fans 124 and 122 to pass through, respectively. The FFC further comprises an opening 142 to place over the head of a user 104. In some embodiments, the FFC may only comprise an opening for a single air moving device. In other embodiments, the FFC may comprise openings for more than two air moving devices. The openings in the FFC may be lined with a stretchable, resilient material, such as an elastic polyurethane film to create a seal around one or more air moving devices.

Figure 6A:
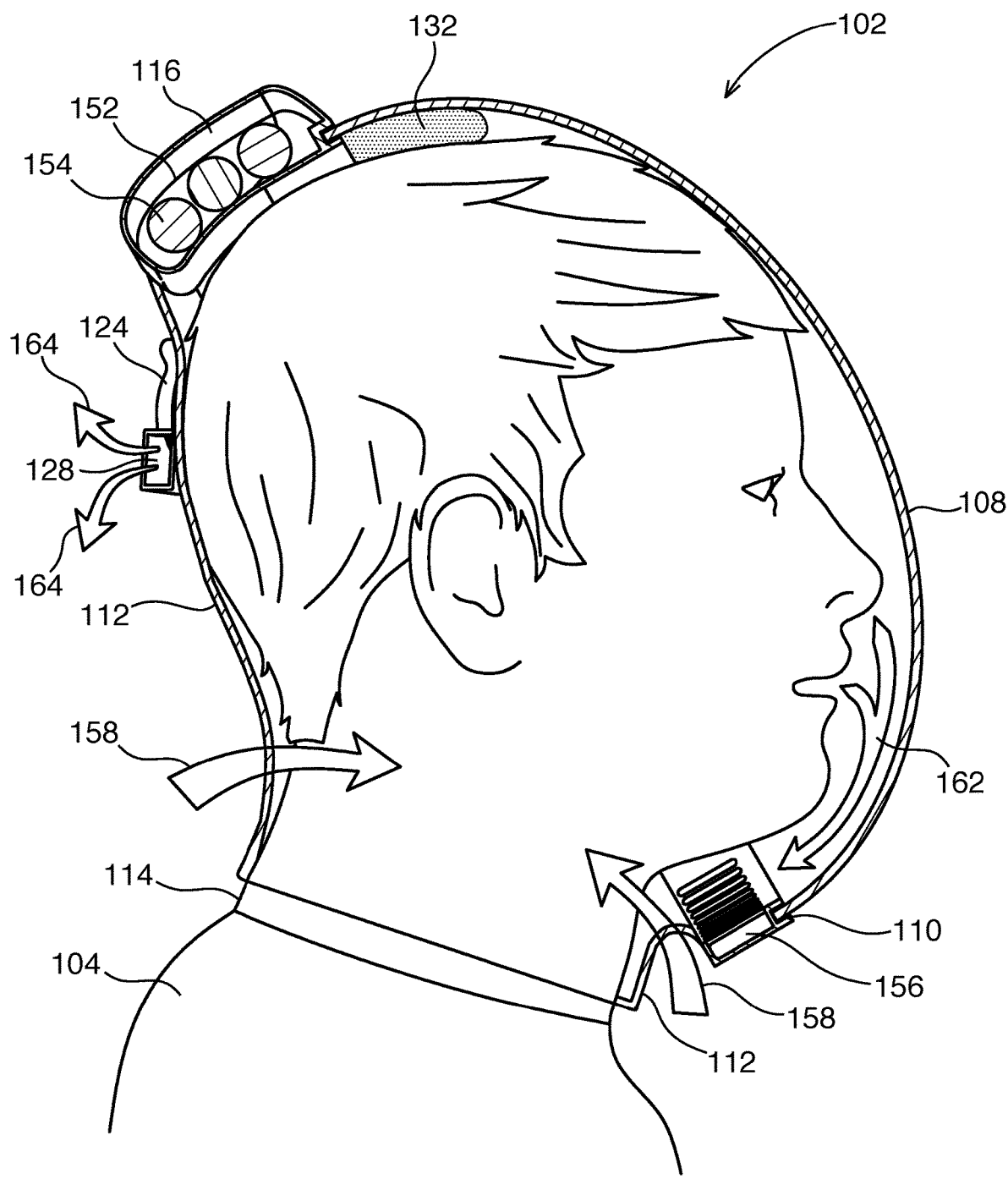
FIG. 6A illustrates a cross-sectional view of an HCD with the head of a user in it and negative air flow, according to an embodiment of the disclosure.

FIG. 6A illustrates a cross-sectional view of an HCD with the head of a user in it and negative air flow, according to an embodiment of the disclosure. FIG. 6 illustrates a battery pack 152 located in compartment 116 further comprising one or more batteries 154. The batteries may be rechargeable and can be recharged by connection to a power outlet or a solar cell. In other embodiments, the batteries may be located in the frame 106.

At the bottom of the frame near the mouth area of the user 104 is seen a cross-section of the exhaust channel 156 that runs from the bottom of the frame towards the fans 122, 124. Air enters the exhaust channel through the intake 134. The fans pull the air through the exhaust channels and pulls the air up through the exhaust port 128.

The negative air flow in the HCD 102 is illustrated in FIG. 6A as follows. Air from the environment outside of the HCD may pass through the fabric of the FFC 112 as intake air 158. Intake air 158 may be also drawn in by the inhale of a user 104 or by the fans 122, 124. When a user exhales from the nose or mouth, the exhale air 162 may then be pulled and drawn into the exhaust channel intake 134 near the mouth of the user by the fans pulling a negative air flow. As air enters intakes 134, the air enters air exhaust channel 156 in the frame. The air then flows from the bottom of the frame towards the top of the frame through the exhaust channel where the fans are located. The exhaust air 164 is then exhausted into the environment out air exhaust ports 126, 128. Thus, the environment, the FFC, the user, intake 134, air flow channel 156, fans 122, 124 and air exhaust ports 126, 128 are in fluidic communication. The air flow process may quickly replace the air in the HCD with outside air from the environment that is filtered through the FFC, to thereby provide a consistent, comfortable, and safe environment for the user.

Figure 6B:
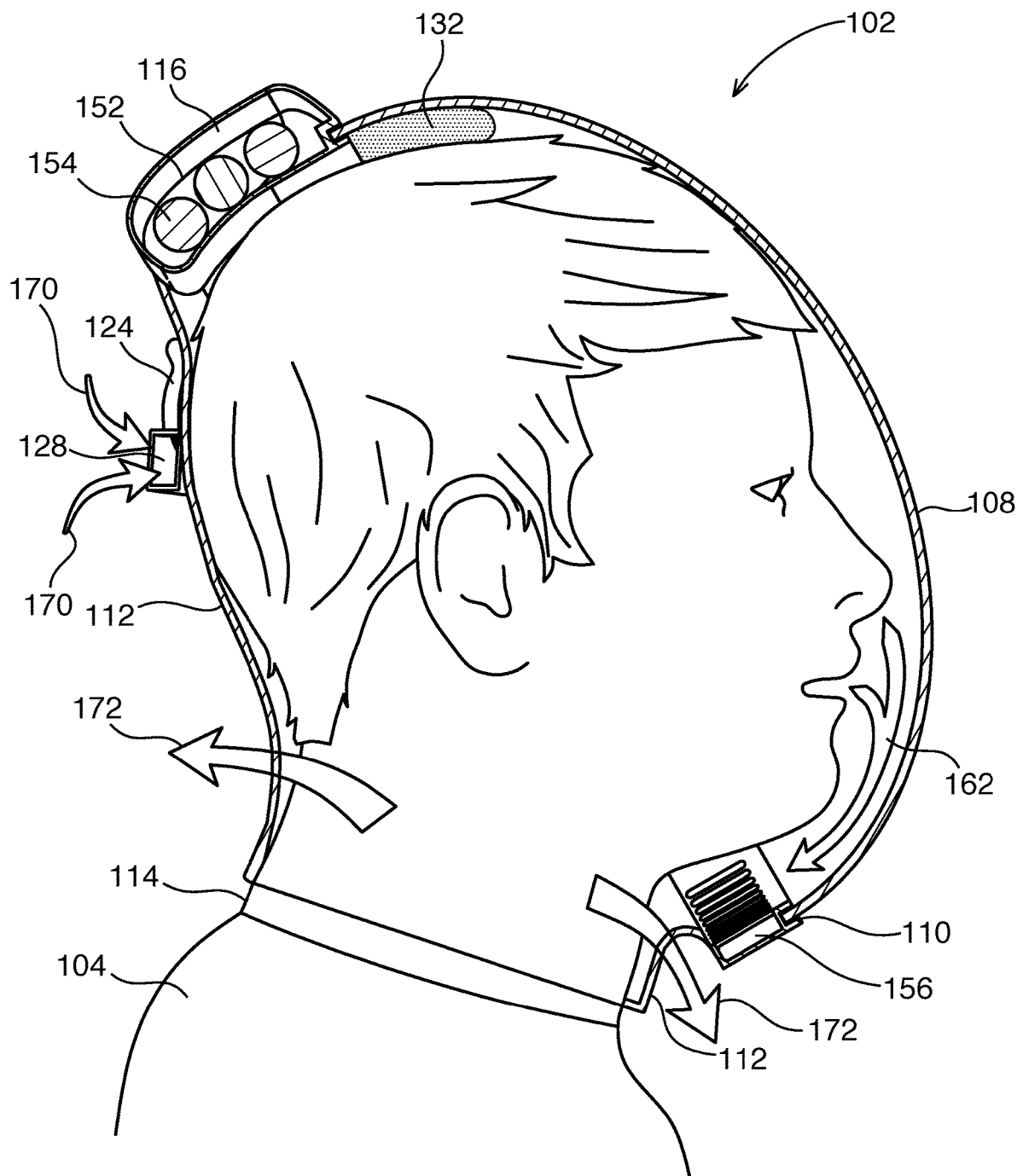
FIG. 6B illustrates a cross-sectional view of an HCD with the head of a user in it and positive air flow, according to an embodiment of the disclosure.

FIG. 6B illustrates a cross-sectional view of an HCD with the head of a user in it and positive air flow, according to an embodiment of the disclosure. The HCD can also operate in a positive air flow mode. The positive air flow in HCD 102 is illustrated as follows. Air 170 is pulled into the HCD by fans 122, 124. Air inside the HCD is replaced by this air and is pushed out of the device as exhaust air 172 through the filtering fabric 112. Exhale air 162 can also be exhausted through the filtering fabric. A filter may be placed over the intake of the fans to filter the incoming air.

In some instance, HCD 102 may also operate in neutral mode. Neutral mode is where the air is balanced by the fans such that air moving in and out of the HCD is controlled by the breathing of the user. In some embodiments, one fan is pushing air into the HCD while the other fan is pulling air out of the HCD.

In some embodiments, such as those depicted in FIGS. 1-6, the air passing out the exhaust ports is filtered by a portion of the FFC that covers the ports. In other embodiments, a separate air exhaust filter may be placed over the air exhaust ports. In either event, this prevents contagion from the user, for example if the user is sick with a respiratory illness, being exhausted into his immediate environment. In other words, this should reduce the amount of microorganisms such as viral, fungal, or bacterial particles that are emitted from the HCD 102. The filter may be made from cotton, foam, paper, or stainless steel. The filter may be a coarse filter, fine filter, semi-HEPA (high efficiency particulate air) filter, HEPA filter, or an ultra-low particulate air (ULPA) filter. The filter may be a combination hydrogen fluoride and hydrogen chloride filter. The filter may be replaceable if clogged, damaged, etc. The filter may be a UV filter or ultrasonic filter to clean and purify the exiting air stream. Alternatively, the filter may be enhanced with electrostatic filtering or water filtering of the air. The air exhaust filter may block at least 95% of particles 0.3 microns or larger (N95) or at least 99.95% of particles 0.3 microns or larger (N99) or at least 99.97% of particles 0.3 microns or larger (N100). As mentioned, in some embodiments, the air exhaust filter may be the portion of the FFC that covers the exhaust ports.

Alternative Frame Design for HCD with Filtering Fabric

The following embodiments describe a different design of the frame than what is previously depicted in FIGS. 1-6 and described above.

Figure 7B:
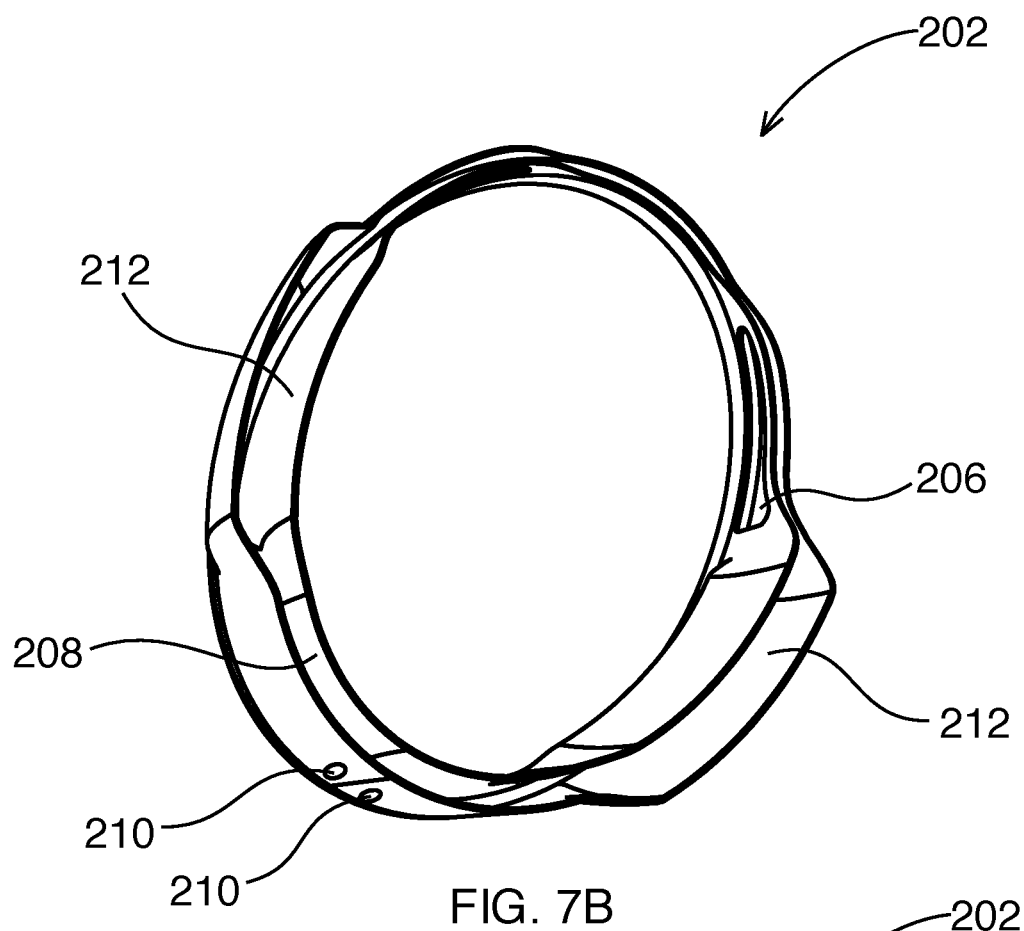
FIG. 7B illustrates a bottom view of a frame comprising compartments for an air moving device and battery for an HCD, according to an embodiment of the disclosure.
Figure 7A:
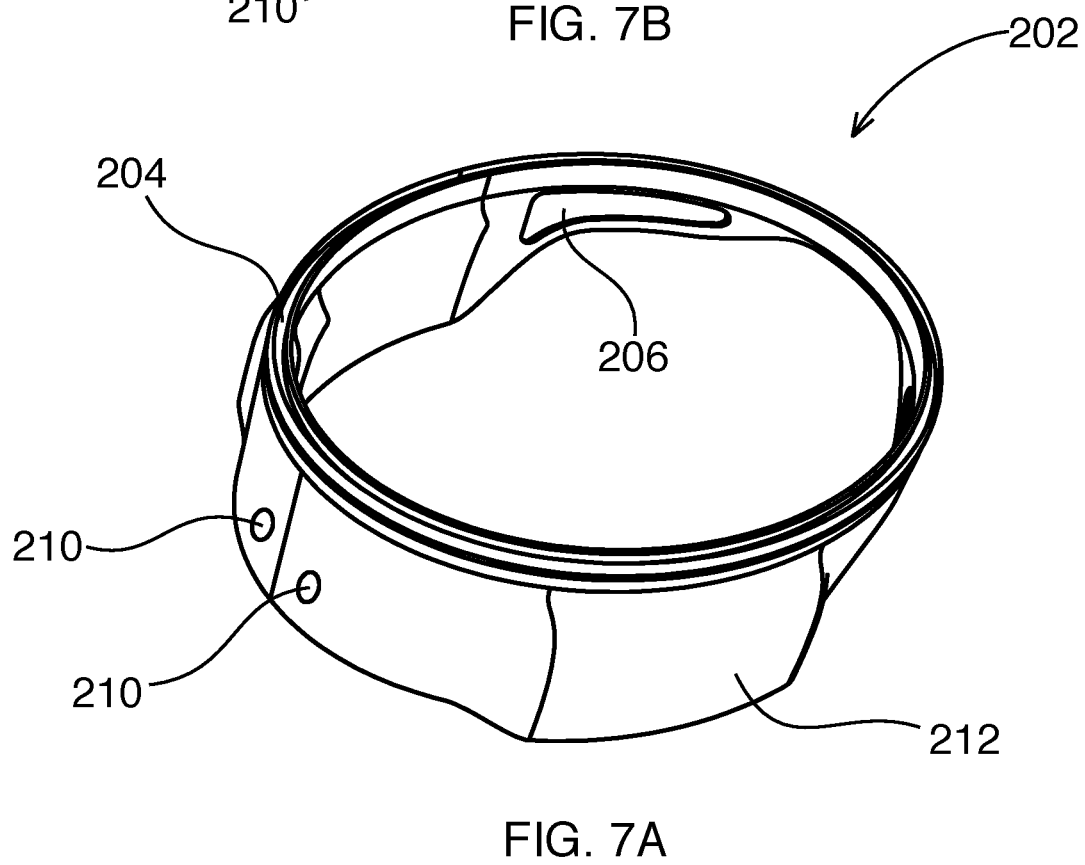
FIG. 7A illustrates a top view of a frame comprising compartments for an air moving device and battery for an HCD, according to an embodiment of the disclosure.

FIG. 7A illustrates a top view of a frame 202 comprising compartments for an air moving device and battery for an HCD, according to an embodiment of the disclosure. FIG. 7B illustrates a bottom view of a frame 202 comprising compartments for an air moving device and battery for an HCD, according to an embodiment of the disclosure. The frame is a hoop-like structure with a generally elliptical shape, but may also be generally circular-like, or some other appropriate shape. The frame comprises a top channel 204 of a constant width along the entire perimeter. The top channel allows for a face shield to be placed and secured to the frame. The top channel may include a gasket or O-ring to aid in securing the frame and to make a seal to a face shield.

Frame 202 further comprises an air intake 206 near the bottom of the frame 206 and near the mouth area of a user. This is similar to intake 134 in frame 106. The frame also comprises a second intake port on the other side of the frame. The frame comprises a second channel 208 on the underside or bottom of the frame. An outer wall and inner wall that are joined at the top but not the bottom forms the channel. The second channel runs along the perimeter and underside of the frame.

Frame 202 further comprises air exhaust ports 210 on the outer wall of the frame. Exhaust ports 210 are located at about the opposite side of the frame from intakes 206. In other embodiments, a partition may be located between the air exhaust ports 210 within channel 208.

The inner width between the inner and outer walls of the second channel 208, varies along the perimeter. The narrowest portion of the frame is in the region between the intake ports 206. The second channel widens along the perimeter towards the exhaust ports 210. The widest portion forms compartments 212. The compartments may also be referred to as "bump outs". In these compartments may be located one or more air moving devices, such as centrifugal fans. The compartments may also contain one or more power sources such as one or more battery packs. The second channel narrows near the air exhaust ports 210.

Figure 8:
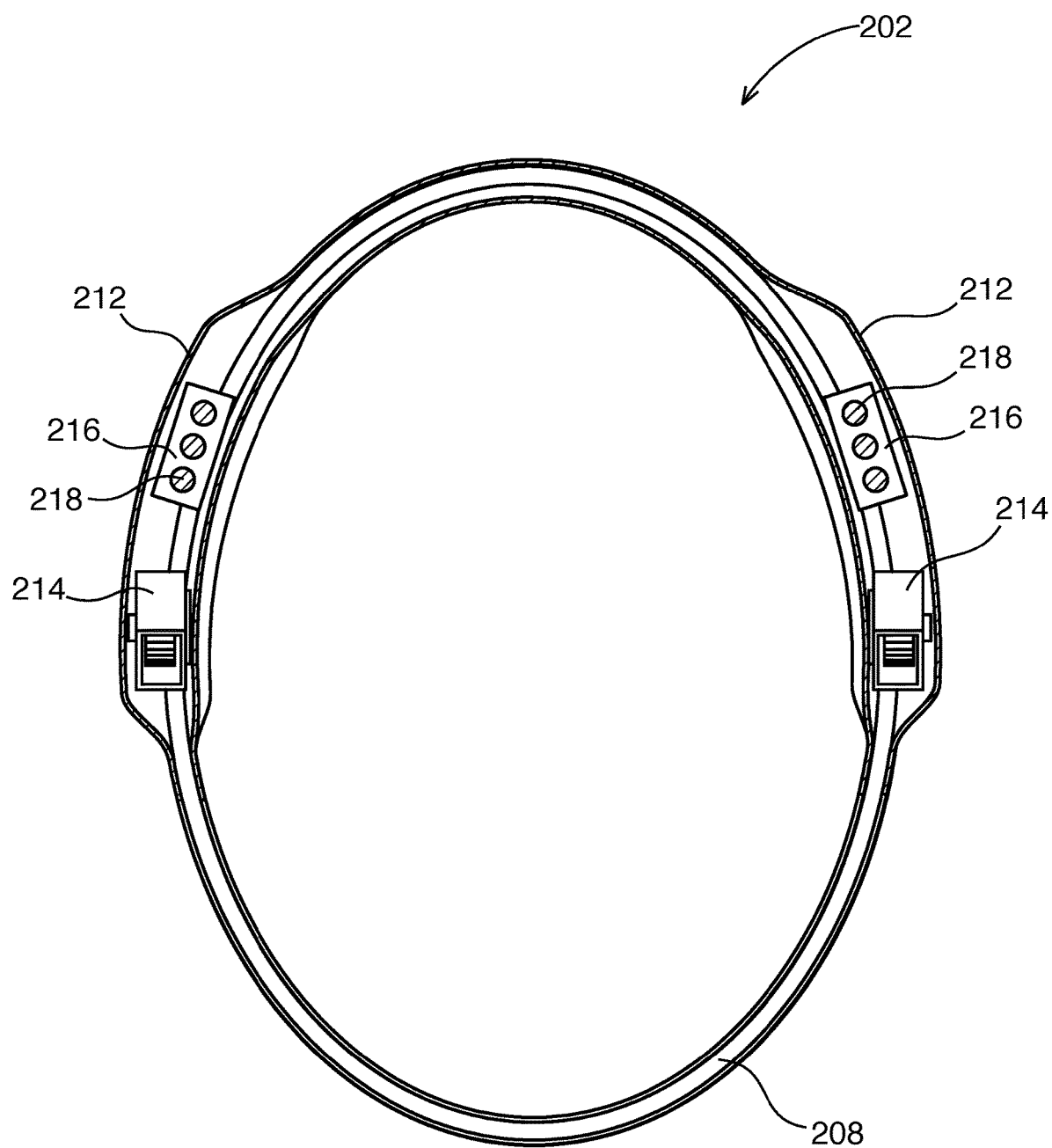
FIG. 8 is a cross-sectional view of a frame comprising an air moving device and battery for an HCD, according to an embodiment of the disclosure.

FIG. 8 is a cross-sectional view of a frame 202 comprising an air moving device and battery for an HCD, according to an embodiment of the disclosure. FIG. 8 illustrates how an air moving device and power source may be arranged in a frame. One or both compartments 212 further comprise a fan 214 to move air. The fan 214 may be a centrifugal fan. The compartments may further comprise a power source such as a battery pack 216 that is in electrical communication with the fan. The battery pack comprises one or more batteries 218. The frame may comprise only one battery pack that may power one or more fans.

Air may flow in frame 202 in an HCD as follows. Air may enter intake ports 206 near the mouth of a user. One or more fans 214 aid in drawing exhaust air into the intake ports. Air then flows through second channel 208 towards the air exhaust ports 210 on the opposite end of the frame from the air intake ports 206. The air may be exhausted into the environment as the air passes through the exhaust ports or through a filter before it is exhausted to the environment.

In some embodiments, there is no frame. The face shield may be directly attached to the FFC. Either the face shield, the FFC, or both may comprise pathways or channels to direct to bring air to the air moving devices and out the exhaust ports.

Flip Up Face Shield for a HCD with Filtering Fabric

The following embodiments describe a design of an HCD with a face shield that can easily be opened and closed for access to the face of a user.

Figure 9:
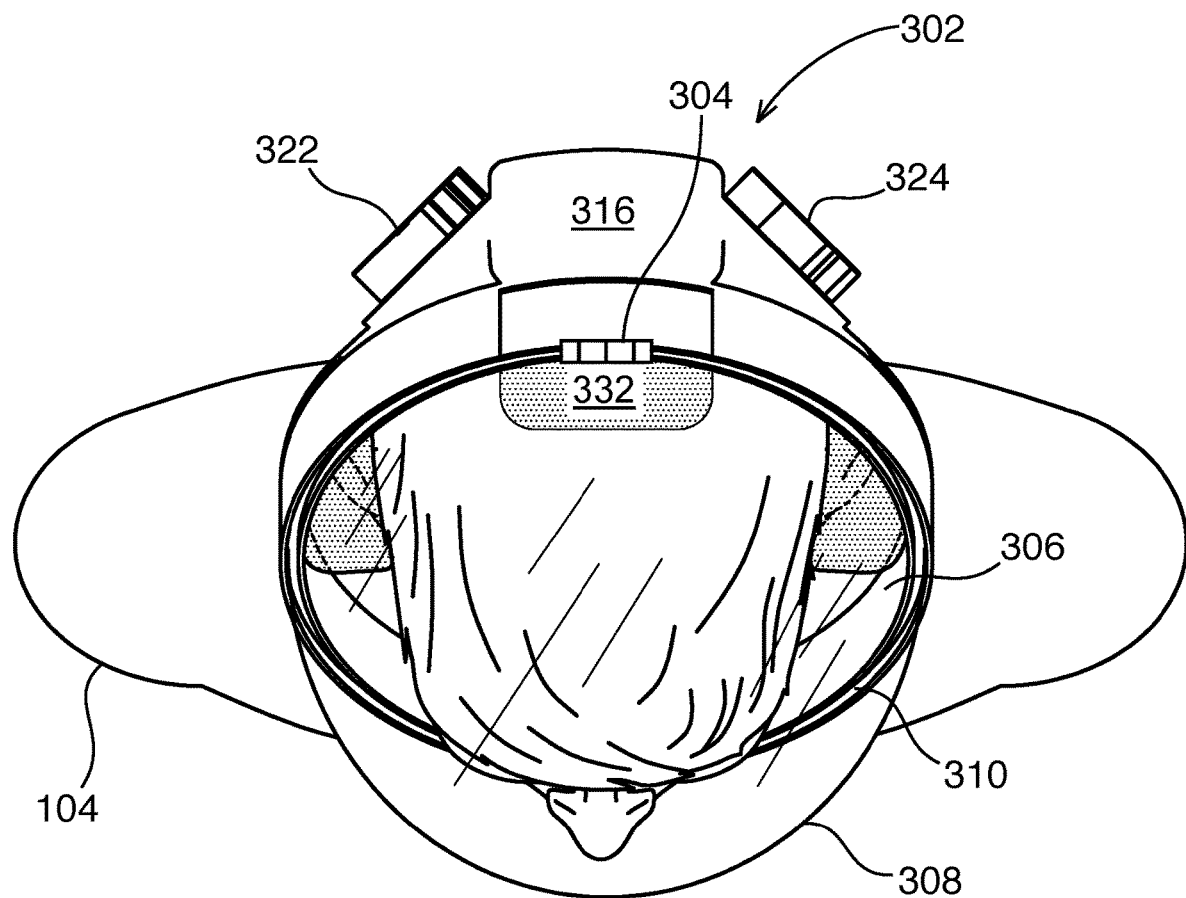
FIG. 9 is a top view of a user wearing an HCD comprising a flip up face shield, according to an embodiment of the disclosure.

FIG. 9 is a top view of a user wearing an HCD 302 comprising a flip up face shield, according to an embodiment of the disclosure. The view in FIG. 9 further shows an HCD 302 comprising a channel 310, fans 322, 324, resting pad 332, and a compartment 316. FFC The HCD further comprises a face shield 308 connected to the frame 306. The face shield is connected by a movable joint, such as the depicted simple hinge 304, to allow for the face shield 308 to be easily opened and pivoted away from the face of the user without removing the face shield entirely from the HCD 302. Alternatively, the movable joint may be a fabric, strap hinge, butt hinge, concealed hinge, plano hinge, offset hinge, overlay hinge, hidden barrel hinge, or a scissor hinge. In a preferred embodiment, the movable joint 304 is a spring-loaded hinge. The spring-loaded hinge can hold the face shield open without the user having to do so. The moveable joint 304 is preferably located at the top of the face shield and connected to the frame as shown in FIG. 9. In other embodiments, the moveable joint may be located at the bottom of the face shield and connected to the bottom of the frame. The moveable joint may be located on either side of the face shield such that the face shield can be opened from the right or left of the user. Preferably, the HCD 302 includes a latch or other locking means, such as magnets, to keep the face shield in place when not opened.

Figure 10:
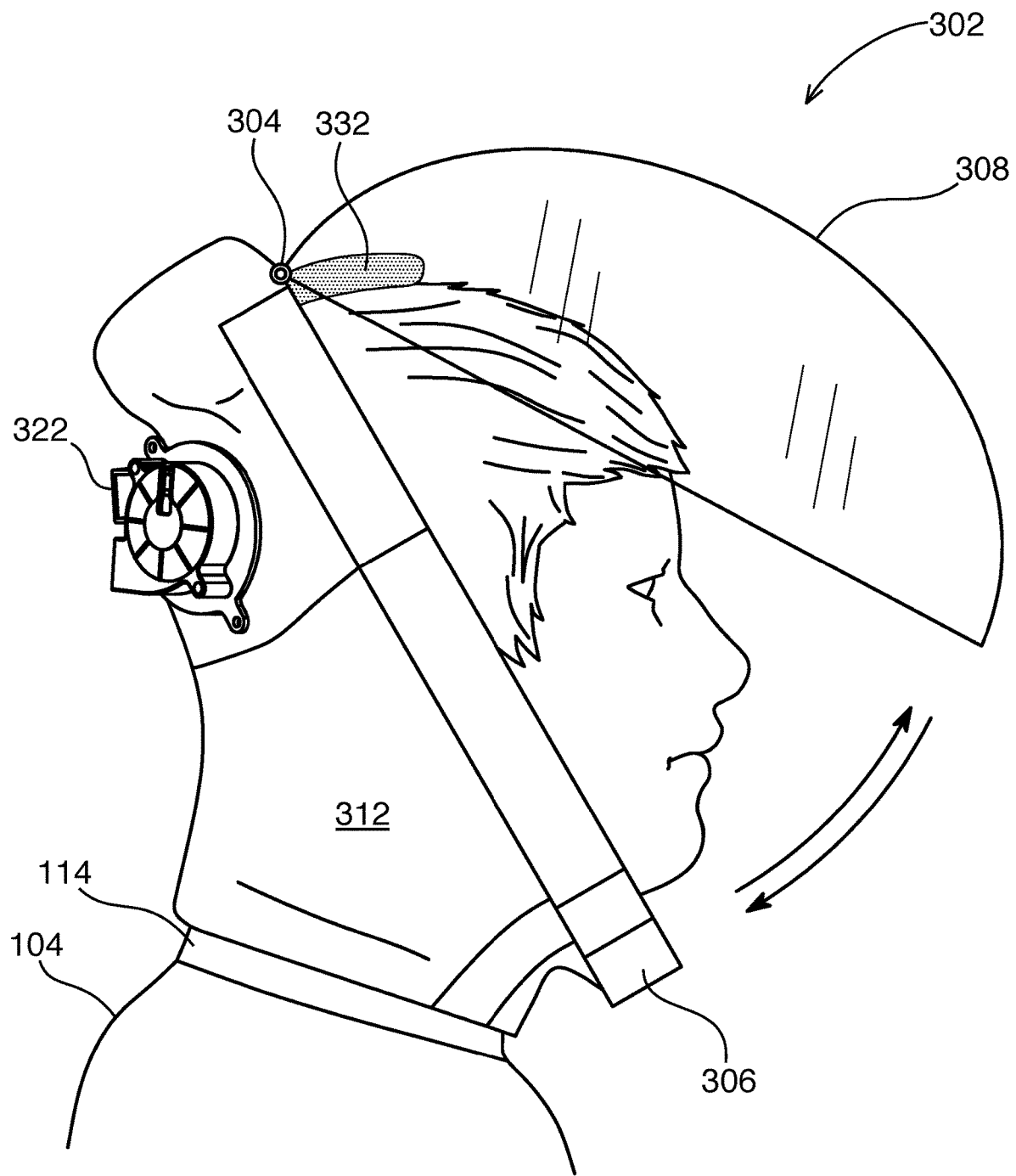
FIG. 10 is a side view of a user wearing an HCD with an opened face shield, according to an embodiment of the disclosure.

FIG. 10 is a side view of a user wearing an HCD 302 with an opened face shield, according to an embodiment of the disclosure. FIG. 10 shows an opened face shield 308 that is connected to the HCD 302 at the top of the frame 306 with a hinge 304. The face shield can be readily opened and closed for quick access to the face of a user 104. The face shield may be able to snap in and out of the frame as it is opened and closed to secure the face shield.

Automatic Air Mover for an HCD with Filtering Fabric

The following embodiments relate to air movers that automatically start when a user places the HCD over their head. The air mover automatically turns off when the user removes the HCD. The air mover may also adjust according to a pre-determined threshold.

Figure 11:
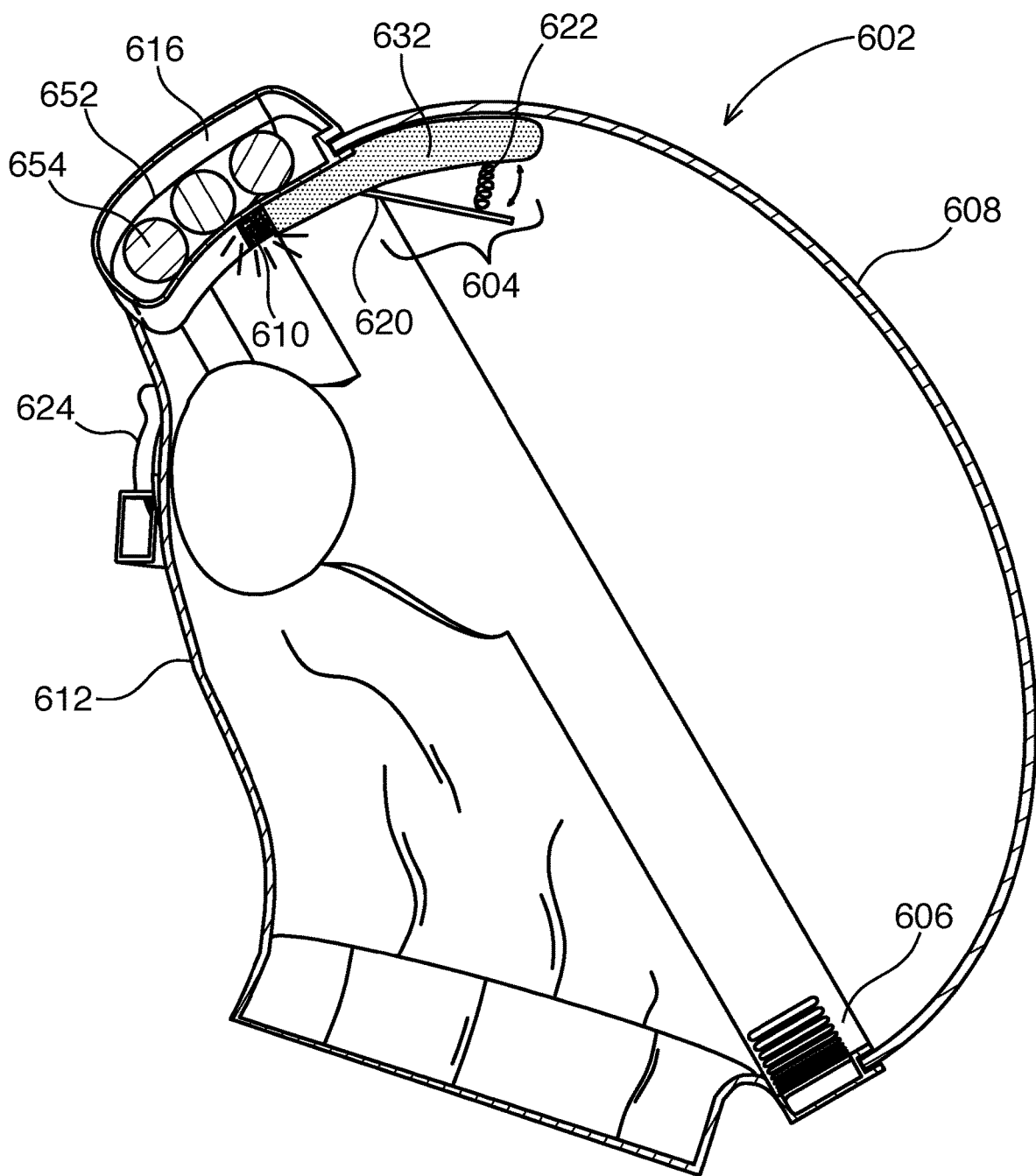
FIG. 11 is a cross-sectional view of an HCD equipped with an automatic air mover, according to an embodiment of the disclosure.

FIG. 11 is a cross-sectional view of an HCD 602 equipped with an automatic air mover, according to an embodiment of the disclosure. HCD 602 embodiment comprises a spring-loaded lever switch 604. The lever switch is located at the top of the HCD near head resting pad 632. The lever switch comprises a lever 620. The lever switch further comprises a resilient device, such as the depicted spring 622. In an exemplary embodiment, the lever may be a part of resting pad. The lever may protrude out of the resting pad such that when it is depressed, it retracts into the resting pad such that when a user places the HCD on, the user cannot feel the lever. The user instead feels the resting pad to provide a comfortable experience.

When the HCD 602 is placed on the head of a user, the lever is depressed and pushed into the resting pad (such as a resting pad cavity) or other location so that it is not uncomfortable to a user. By depressing the lever, the switch completes an electrical circuit such that power from battery pack 652 located in a compartment 616 comprising one or more batteries 654 or other power source provides an electrical current to an air moving device, such as a fan 624. The air mover then automatically turns on. When a user removes the HCD, the lever is extended by the spring which breaks the electrical circuit between the air mover and power source which automatically shuts down the air mover.

HCD 602 preferably comprises one or more sensors 610. The sensor can detect the head of a user and sends a signal to turn on the air mover. The sensor may be a temperature sensor, pulse rate sensor, IR sensor, optical sensor, humidity sensor, proximity sensor, motion sensor, skin moisture sensor, force sensor, or a biometric sensor. Upon detection of the head of the user placing the HCD on, the automatic air mover turns on. This may be done by measuring the temperature of a user or a proximity sensor of a nearby object, such as the head of a user. When the HCD is removed, the sensor no longer detects the head of a user and the automatic air mover then turns off. The sensor may be located anywhere within the HCD, such as on the face shield 608, in the frame 606.

The sensor may detect a change in the biometric data of a user which may be relayed to a controller. The controller would then adjust the air flow from an air mover until a pre-determined biometric data target is reached. The biometric data may include skin temperature, pulse rate, skin moisture, or oxygen saturation. A processor may also be combined to process the signals from the sensors.

The HCD may further comprise a controller that is configured to adjust the rate at which the air mover moves air. A sensor detects the air flow. When the air flow falls below a pre-determined threshold of air flow, the sensor relays the information to a controller that adjusts the rate of air flow from an air mover. The air mover increases the air flow until the threshold is reached. In some instances, the air flow may rise above a pre-determined threshold such that the controller decreases the air flow. The HCD further comprises a sensor for generating signals indicative of at least one of air pressure, ambient temperature, body temperature, skin moisture, blood oxygen saturation, respiration rate and pulse rate, and a processor for processing signals from the sensor and providing instructions to the controller to adjust the rate of the air mover according to predetermined parameters.

The HCD may further comprise a communication module for receiving signals relating to at least one of air pressure, ambient temperature, body temperature, skin moisture, blood oxygen saturation, respiration rate and pulse rate, and a processor for processing signals from the communication module and providing instructions to the controller to adjust the rate of the air mover according to predetermined parameters. The communication module is configured to receive signals from the user's smart device. The device is configured to communicate with an app running on a user's smart device, which app is configured to provide alerts to the user and to allow the user to adjust the rate of the air mover. The communication module is configured to receive signals from the user's wearable smart device.

The HCD may further comprise a sensor for generating signals indicative of the concentration of oxygen, and a processor for processing signals from the sensor and providing instructions to the controller to increase the rate of the air mover when the oxygen concentration of oxygen falls below a predetermined level. The device further comprises a user warning system, configured to alert the user when the concentration of oxygen falls below the predetermined level.

The HCD further comprises a sensor for generating signals indicative of the concentration of carbon dioxide, and a processor for processing signals from the sensor and providing instructions to the controller to increase the rate of the air mover when the concentration of carbon dioxide rises above a predetermined level. The device further comprises a user warning system, configured to alert the user when the concentration of carbon dioxide rises above the predetermined level. The HCD further comprises a second sensor for generating signals indicative of the concentration of oxygen, and wherein the processor processes signals from the sensor and the second sensor and provides instructions to increase the rate of the air mover when either the concentration of carbon dioxide rises above a predetermined level or the concentration of oxygen falls below a second predetermined level.

The HCD may further comprise two or more electrodes. The electrodes may be located in the FFC, in the resting pad, or elsewhere in the device where the skin of the user comes into contact with the electrodes. By coming into contact with the electrodes, the circuit is closed and a current is able to pass. This current is detected by a sensor that initiates the starting of the air mover.

In some embodiments, the automatic air mover may be combined with a head covering device that comprises a flip-up shield. The flip-up shield may be connected by a hinge to the frame, as previously illustrated herein in FIG. 10. The air moving device may shut off when the shield is flipped open by the user and pivoted away from the face of the user. The air moving device may turn on when the shield is closed.

Shroud for HCD with Filtering Fabric

The following embodiments include a shroud-like component that can at least partially cover the transparent face shield in an HCD when a user desires to have a darkened environment to relax, sleep, or for enhanced privacy. In some embodiments, the shroud completely covers the transparent face shield, while in others, the shroud only partially covers the transparent face shield, so as to provide privacy, while allowing some light inside the device.

Figure 12:
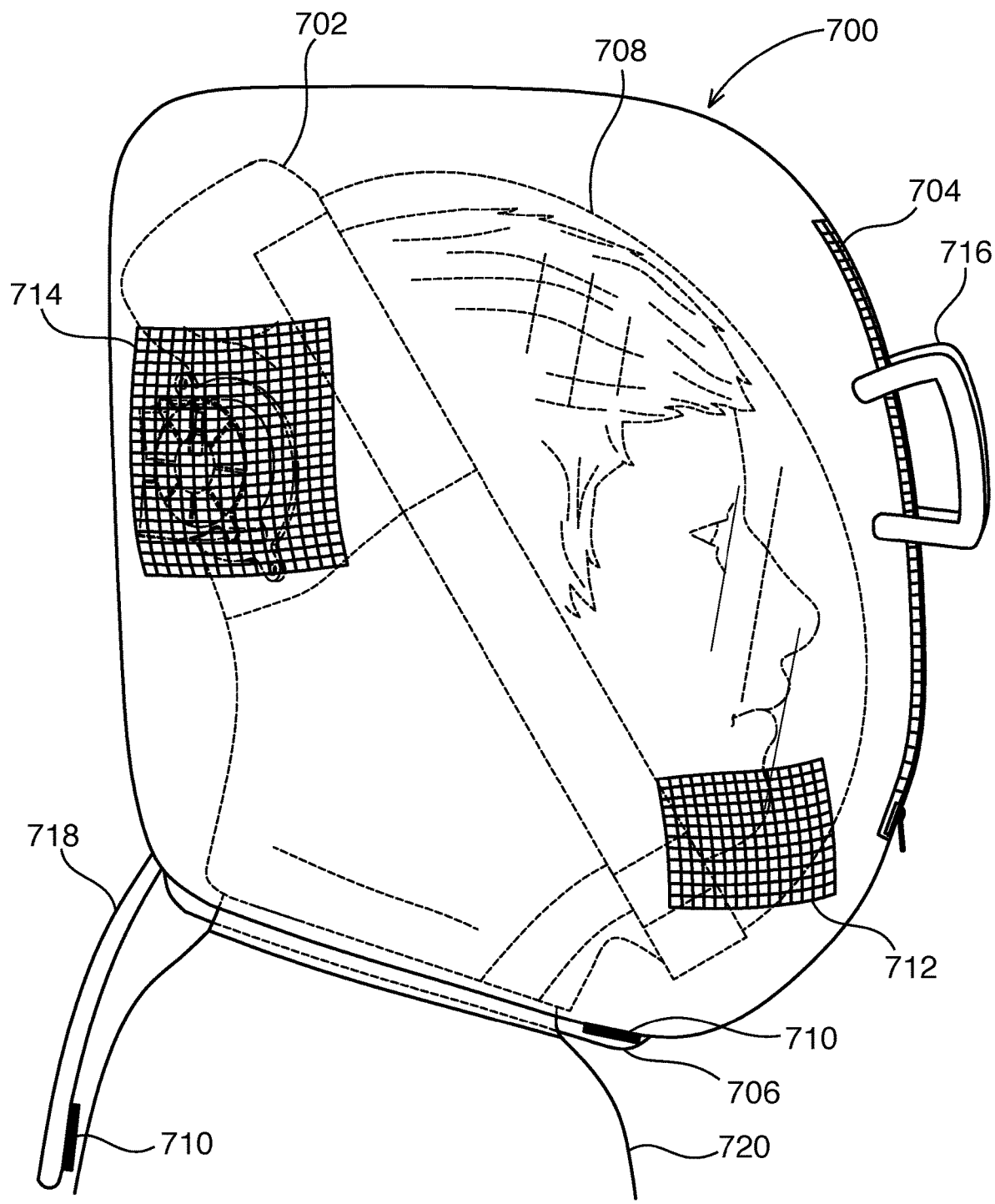
FIG. 12 is a side view of a user wearing an HCD equipped with a shroud, according to an embodiment of the disclosure.

FIG. 12 is a side view of a user wearing an HCD 702 equipped with a shroud 700, according to an embodiment of the disclosure. A user 720 wearing an HCD 702 further comprises a shroud 700 that is placed or slipped over the HCD. The shroud 700 comprises a flexible, stretchable, or stiff fabric and may also be referred to as a cover, blackout cover, sleep cover, or privacy cover. In preferred embodiments, the shroud is opaque. The shroud may comprise a polymeric material such as nylon, rayon, spandex, lycra, viscose, or a natural fabric such as cotton or wool. Preferably, the shroud comprises a sealing device 704 to seal shut the shroud when placed over an HCD 702. The sealing device may be a zipper as shown in FIG. 12 but may also be a hook and loop fastener, a drawstring, laces, or other device. In some embodiments, the shroud may be stretched and fit snuggly over the HCD such as how a sock fits over a foot. In a preferred embodiment, the shroud has a much higher porosity and higher permeability than the fabric in an HCD to allow for unrestricted air low. The shroud may have twice as high air permeability than the filtering fabric. The shroud may be constructed entirely of mesh except the portion that covers the face shield. The shroud may partially or completely cover the face shield in an HCD. The shroud may partially cover the transparent face shield, so as to provide privacy, while allowing some light inside the device.

The shroud 700 further comprises an opening 706 so that the head of a user 720 or a user wearing an HCD can pass. The opening comprises a flap 718 that can be closed when the user is not using the HCD. In a preferred embodiment, the flap may be held shut using hook and loop pads but may also be a zipper, clasps, or buttons.

The shroud 700 further comprises one or more openings 712 for intake air. The intake air opening 712 allows air to pass through the shroud, through the HCD and then to the user wearing the HCD. The intake air opening preferably is a mesh material that minimally restricts air flow.

The shroud preferably further comprises one or more openings 714 for exhaust air. Exhaust air opening 714 allows for air to pass from the fan exhaust port to outside the shroud to the environment. The exhaust air opening is preferably a mesh material that minimally restricts air flow to escape the shroud. The openings 712, 714 allow unrestricted air flow by one or more air moving devices in an HCD while a user safely relaxes or sleeps.

The shroud further comprises one or more optional handles 716. The handles are to provide a way for a user to carry the HCD when stored or toted in the shroud. The shroud further protects the face shield 708 from getting scratched or damaged.

Figure 13:
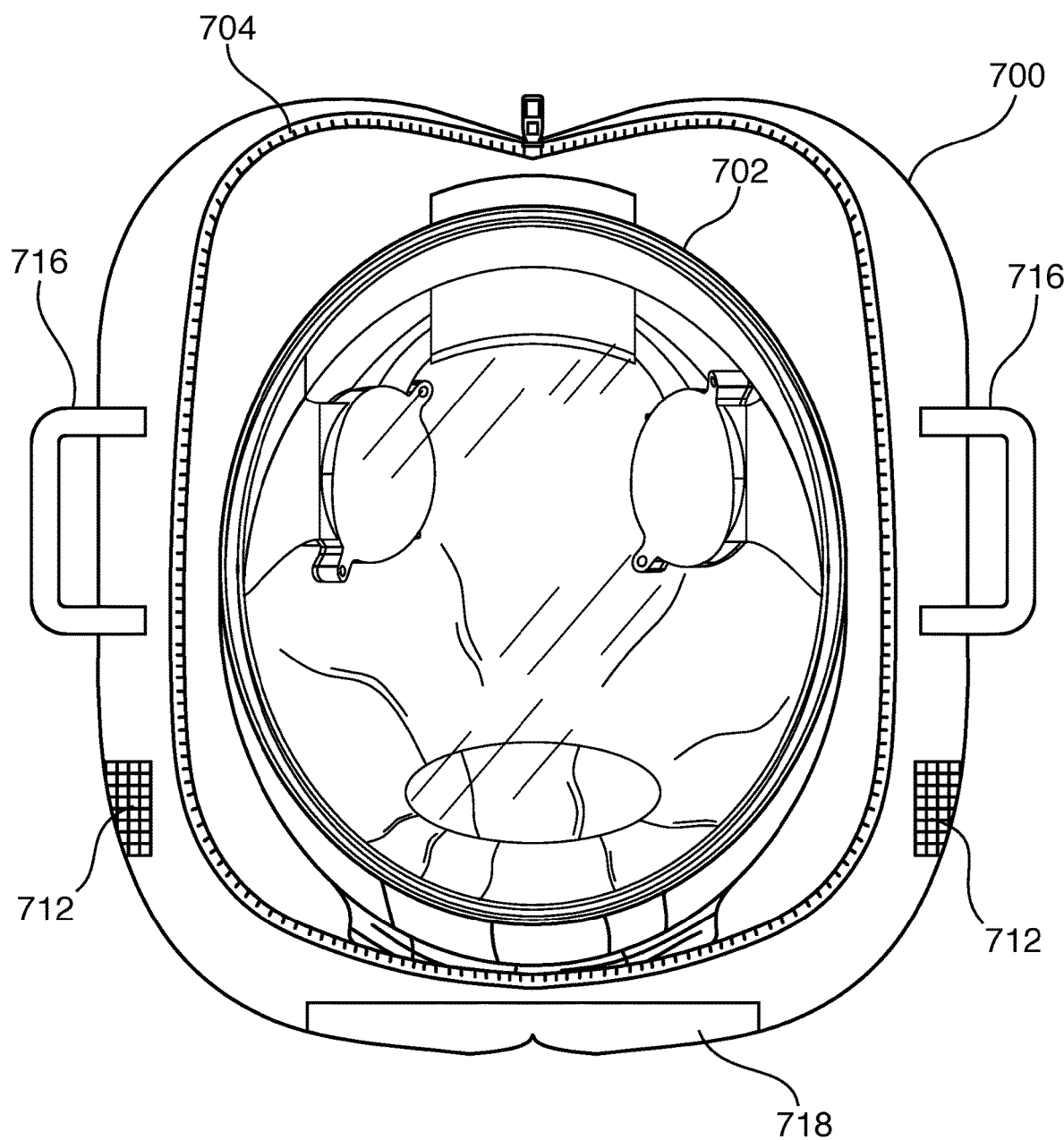
FIG. 13 is a view of an empty HCD placed in a shroud, according to an embodiment of the disclosure.

FIG. 13 is a view of an empty HCD 702 placed in a shroud, according to an embodiment of the disclosure. FIG. 153 shows how an HCD fits into a shroud 700 which can also act as a carrying case. In this view, the flap 718 is closed.

Figure 14:
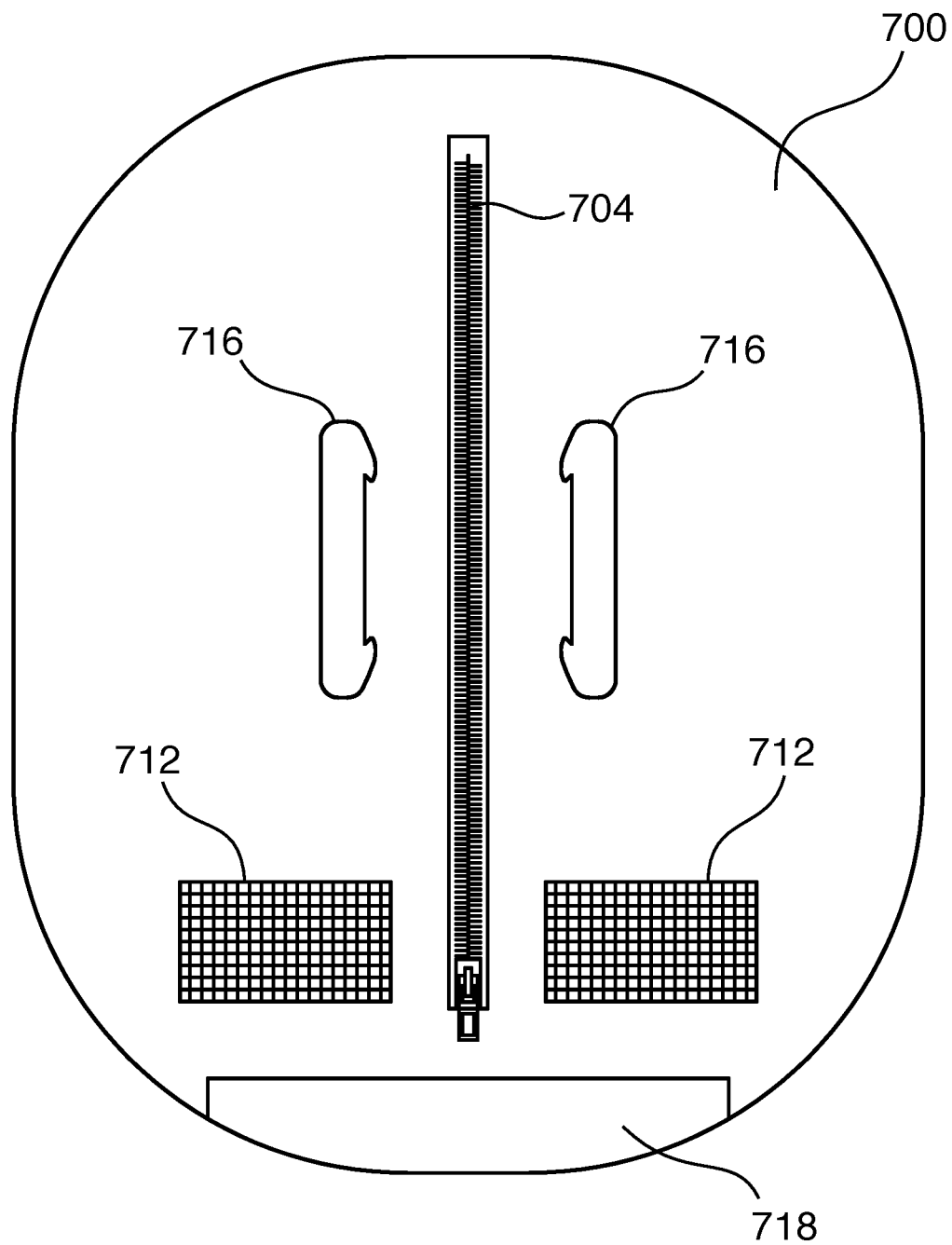
FIG. 14 is a view of a closed shroud 700, according to an embodiment of the disclosure.
Figure 16:
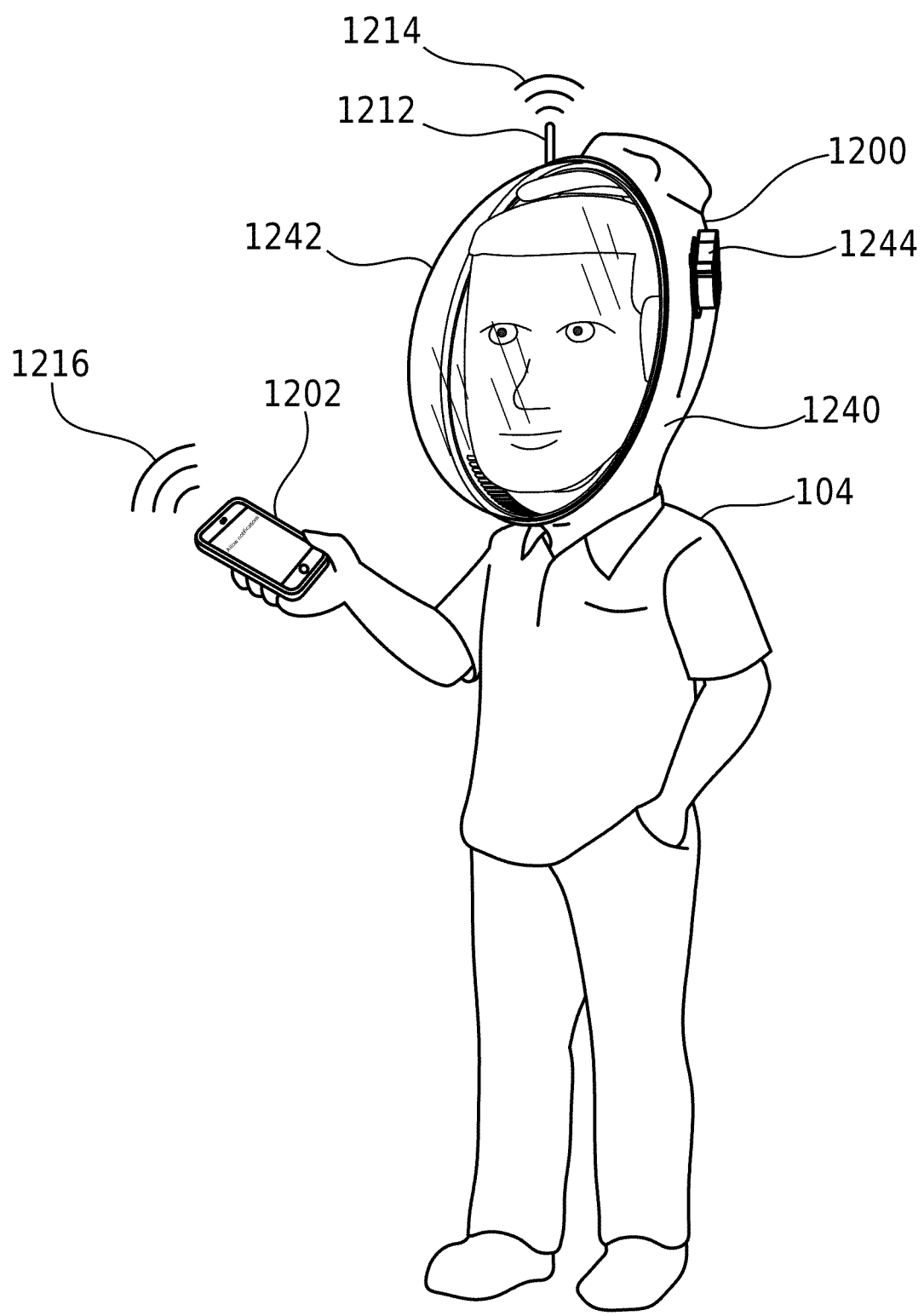
FIG. 16 is a view of user with an HCD that is controlled and monitored by an app on a smart device, according to an embodiment of the disclosure.

FIG. 14 is a view of a closed shroud 700, according to an embodiment of the disclosure. FIG. 16 illustrates a closed shroud 700 with zipper 704 closed. In this view, the flap 718 is closed. The shroud comprising an HCD inside may be stored until next use or carried to a different location while protecting the face shield 708 from getting scratched or damaged.

Figure 15:
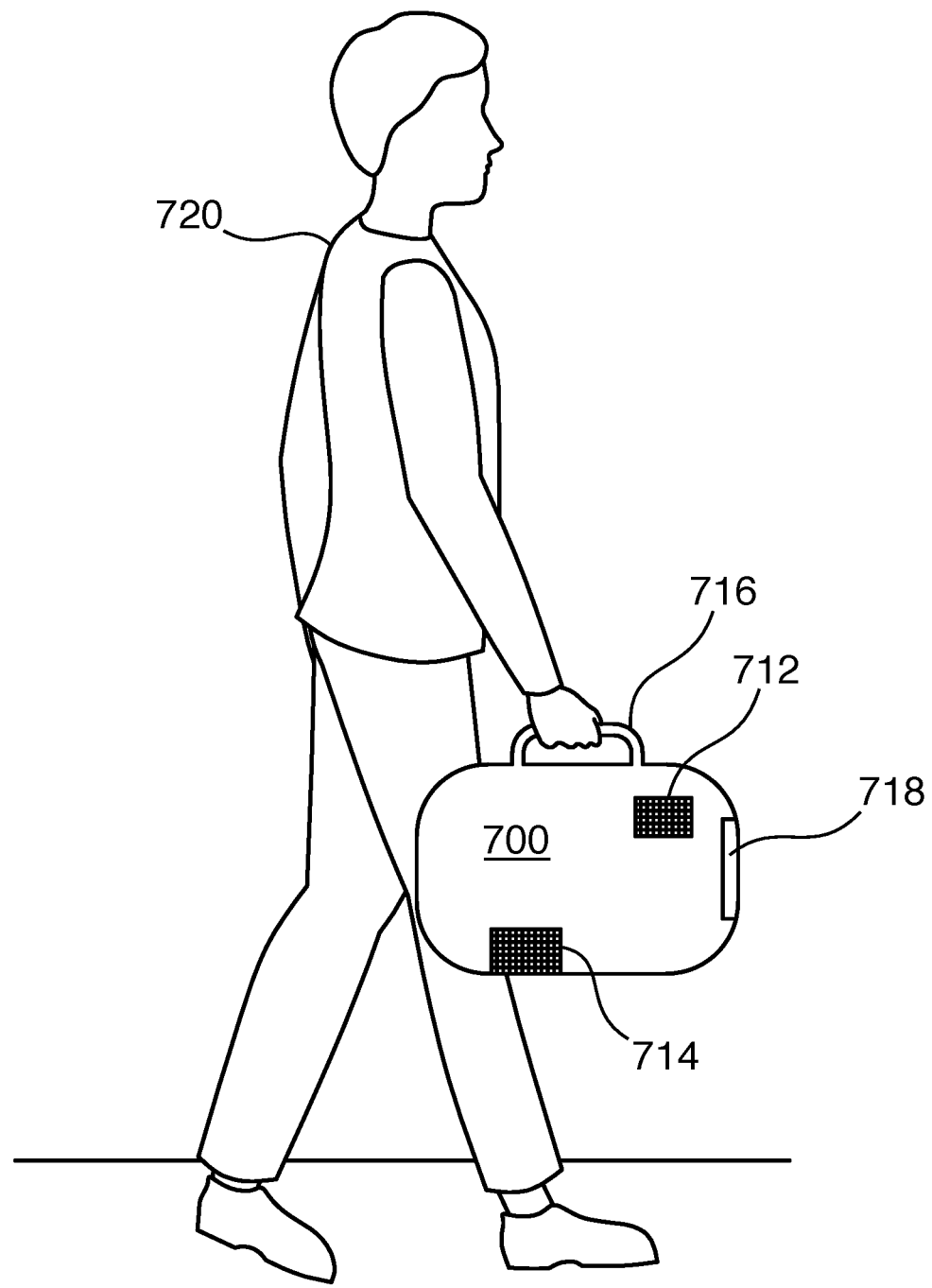
FIG. 15 is a view of an HCD in a shroud being carried by a user, according to an embodiment of the disclosure.

FIG. 15 is a view of an HCD in a shroud 700 being carried by a user, according to an embodiment of the disclosure. FIG. 15 further shows a user 720 carrying a shroud 700 by the handles 716. In some embodiments, shroud may instead be just a carrying case and not be used for a blackout device. In some embodiments, the carrying case may be comprised of a rigid material. The shroud can serve as a protective cover for the device when not in use.

Smart App for Working with an HCD with Filtering Fabric

The following embodiments describes a personal air filtration system (PAFS), such as an HCD, wherein the electronic functions can be controlled and monitored by a configured smart app running on a user's smart device. The smart app may be compatible with smart devices, such as smart phones, tablets, and wearables. The smart app may also include natural language processing (NLP) capabilities to allow for hands-free device usage, greater accessibility for individuals with disabilities, convenience, and novelty. The smart app may have augmented reality capabilities. The smart app may include predictive analytics for a more personal and engaging experience based on past movements and activities. The smart app may utilize biometric data, GPS, or other sensory hardware to provide information about the user, their environment, and their location. The smart app can be downloaded onto a mobile device such as a wearable, tablet, laptop, or cell phone. The smart app can be downloaded onto a non-mobile device such as a desk top computer.

FIG. 16 is a view of user with an HCD 1200 that is controlled and monitored by an app on a smart device 1202, according to an embodiment of the disclosure. The HCD is similar to other HCD embodiments described herein comprising a flexible FFC component 1240, rigid face shield component 1242, air moving device 1244, and compartment 1210 to store a power source such as rechargeable batteries. The HCD further comprises an antenna 1212 to receive a wireless signal that is extended from the top of the HCD. The extending antenna may be rigid or a flexible whip antenna. In other embodiments, the antenna may be hidden from view within the frame of the HCD or under the FFC. In other embodiments the antenna may be in the form of wires located on the surface of the rigid face shield or frame.

The HCD comprises a controller that may include one or more communication systems, including Bluetooth communication chips, Internet Wi-Fi transceivers, network transceivers, a wireless mesh network device such as Z-Wave network transceiver, or a combination thereof to wirelessly communicate with a smart device. The controller may be mounted in the rigid component of the HCD. The controller is able to control various components of the HCD such as the rate of the air mover, humidity level, temperature, dimming of the face shield using an electrochromic layer, audio visual and communication components such as an image or video display, microphone, or speaker on demand from the user using an app on a smart device. The smart device may be a stand-alone smart device or integrated with the rigid component of the HCD. The one or more communication systems may communicate by a wireless signal 1214 with at least one of external remote controllers and a cloud-based network in real-time, intermittent time, or in pre-determined time intervals and lengths of time or a combination thereof.

The one or more communication systems may receive instructions from the external remote controller, generate signals 1216 instructing components of the HCD to operate and to monitor the status of various components. The communications system may generate a signal 1214 informing the external remote controller of the status of at least one device in the HCD. In an exemplary embodiment, the remote controller is a smart device such as a tablet, wearable, or mobile phone 1202.

The smart device communicates to a plurality of devices within the HCD. The smart device may also include a wireless transmitter and wireless transceiver and have a connection to each network device of the one or more HCD devices. The connection may include a wired or wireless interface such as Bluetooth, WIFI, mesh network or similar wireless protocol.

Figure 17:
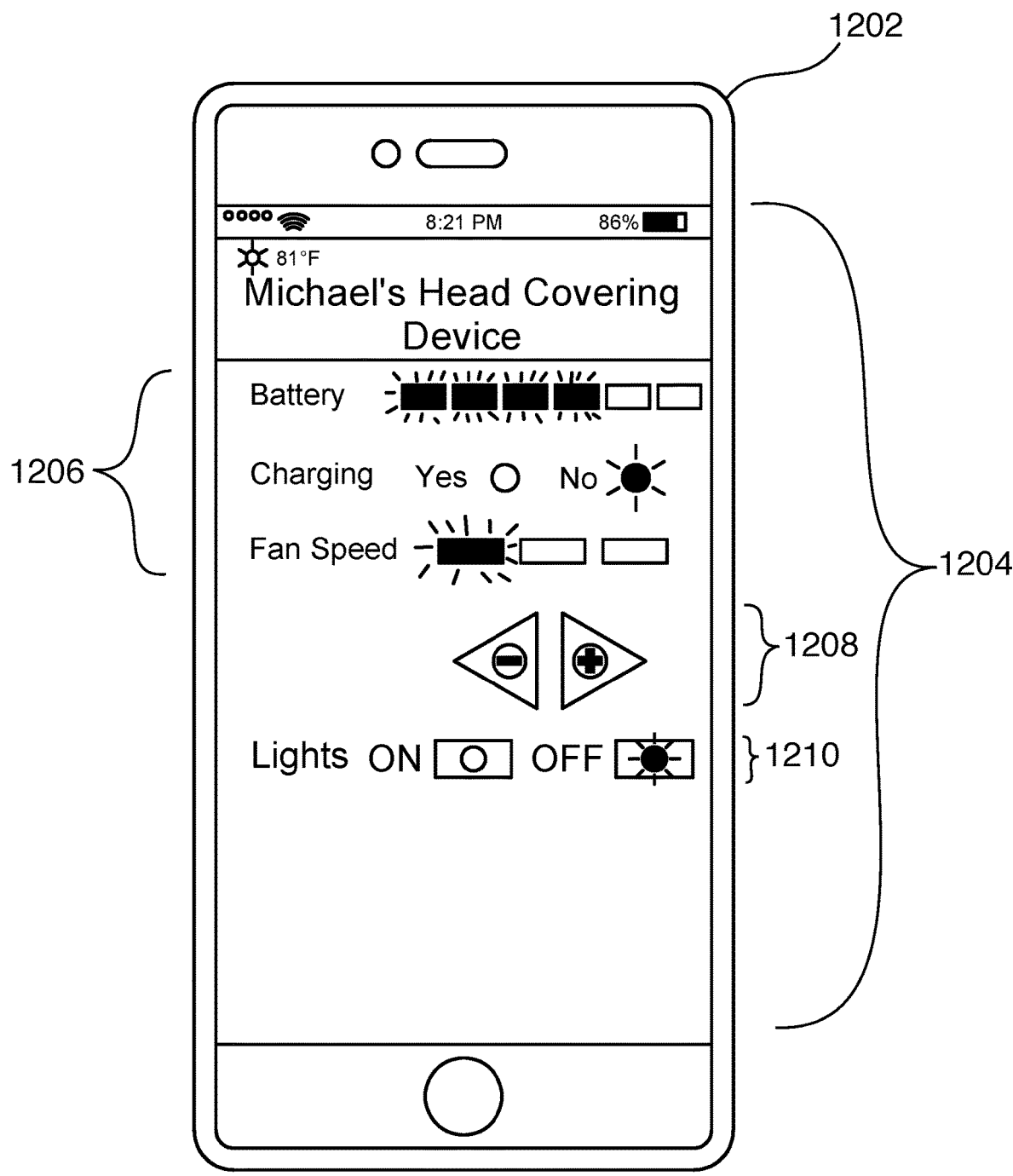
FIG. 17 shows a graphical user interface for monitoring and controlling functions of an HCD, according to an embodiment of the disclosure.
Figure 18:
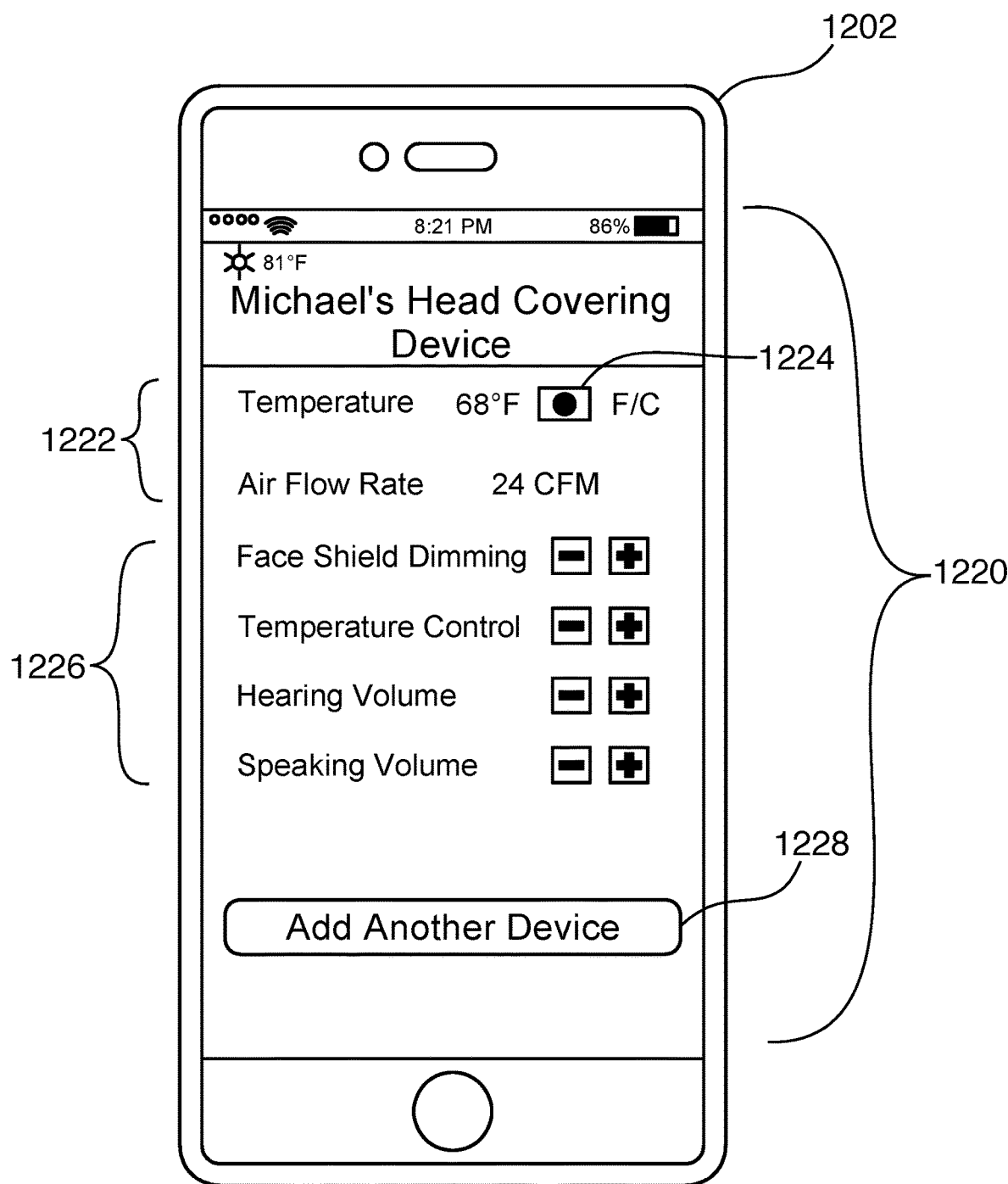
FIG. 18 shows a graphical user interface for monitoring and controlling functions of an HCD, according to an embodiment of the disclosure.
Figure 19:
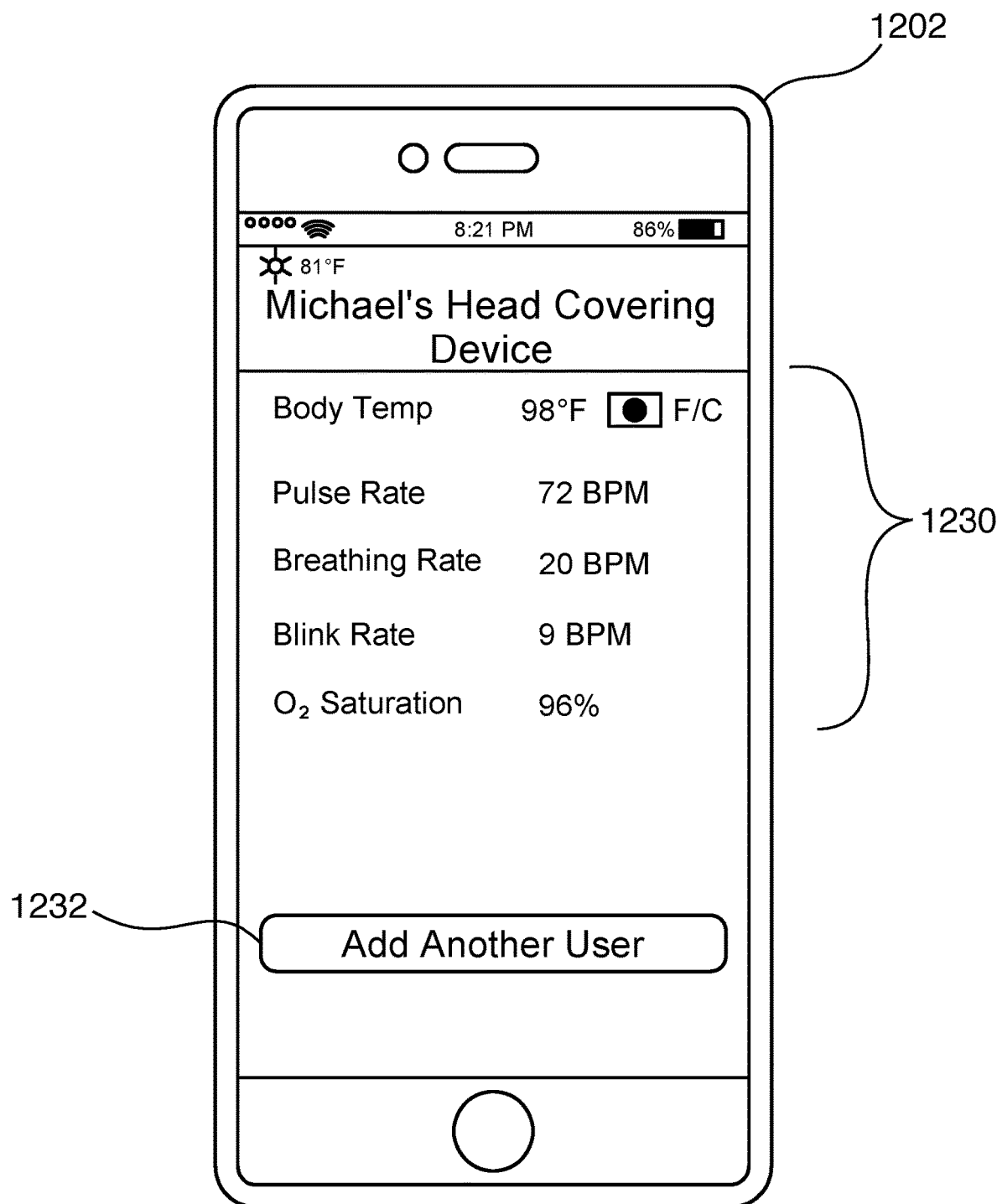
FIG. 19 shows a graphical user interface for monitoring biometric information, according to an embodiment of the disclosure.

FIGS. 17 through 19 show various exemplary graphical user interface (GUI) pages associated with an application configured to execute on a mobile device. Nevertheless, in other embodiments, the application may be configured to execute on a desktop computer, workstation, tablet, laptop, or other suitable computing device.

FIG. 17 shows a graphical user interface for monitoring and controlling functions of an HCD with an app, according to an embodiment of the disclosure. The GUI example embodiment 1204 displayed on a mobile phone 1202 displays various information and multiple indicators and control functions. The name "Michael's Head Covering Device" as displayed at the top of the screen along with standard information such as the time, temperature, weather conditions, and battery charge level of the smart device. Although the name "Michael's Head Covering Device" is used for the name of the HCD for illustrative purposes, the user can give the HCD device any name. In this embodiment, the battery charge status, whether the HCD is plugged in a charging, and the variable fan speed indicators 1206 are displayed. The app may provide an audible alert or a visual alert for the user on the GUI if the battery level goes below a certain level where a limited amount of usage time is left. Controls for the fan speed 1208 are also shown wherein touching "-" decreases the fan speed and pressing "+" increases the fan speed. Towards the bottom of the GUI is a control function where a user can touch "ON" or "OFF" to turn the lights on in an HCD. The lights may be lights inside or outside of the HCD.

FIG. 18 shows a graphical user interface for monitoring and controlling functions of an HCD, according to an embodiment of the disclosure. In this GUI embodiment 1220, the temperature and air flow rate 1222 inside the HCD are displayed. The temperature can be switched by touching an icon 1224 on the screen to toggle between ° F. and ° C. depending on what is desired by a user. Other functions 1226 may be controlled such as activating an electrochromic layer to dim the face shield, control the internal temperature of the HCD, turn up the hearing volume for the user to hear others, or turn up the speaking volume for others to better hear the user of an HCD. Electromagnetic radiation sensors may be used to determine if the electrochromic layer needs to be activated to limit amount of light entering the face shield and provide shade (i.e., shade function) to the user or by a command from the user.

In some embodiments, the mobile device app may be able to monitor and control more than one HCD. At the bottom of GUI embodiment 1220, a user can touch "Add New Device" 1228 to add another HCD. The HCD could be added by a QR code located on the HCD or search by the name of the HCD. A Bluetooth verification method could be used to create a connection between the mobile phone device and the HCD. A QR code located on an HCD device could also be scanned to link the HCD to the mobile phone app.

FIG. 19 shows a graphical user interface for monitoring biometric information, according to an embodiment of the disclosure. In this example, various biometric data are displayed 1230 such as body temp, pulse rate (beats per minute (BPM)), breathing rate (breaths per minute (BPM)), blink rate (blinks per minute (BPM)), and oxygen ($O_2$) saturation levels that are collected by various sensors in the HCD. Other biometric data may be displayed such as head orientation, closed eyes, and combinations thereof. The app may be able to store and monitor the biometric data for more than one user. This can be achieved by touching "Add Another User" 1232 shown at the bottom of the GUI. The biometric data can be selectively collected on a user if the designated user is confirmed by a fingerprint or retinal scanner. An HCD may further comprise a processor for receiving signals from biometric sensors and communicate biometric information to the smart device, and wherein the app is configured to receive and process biometric information and provide reports to the user.

The app may provide alerts for any information collected by the HCD such as performance of the HCD itself or biometric data collected on the user. The alerts may be programmed and set by the user or may be set based on the age, weight, height, or other information of the user.

The app may receive signals from one or more sensors to test and/or monitor fitment of the system such as the detection of leaks around the seal of the flexible fabric component and the neck area of the user. The sensors may be able to detect a gas for use in testing fitment.

The app may provide alerts for information collected by safety sensors in occupational safety applications such as exterior temperature, noise level, or air quality. The app may be configured to control the temperature, air flow, and volume inside of the HCD based on the ambient noise levels in occupational and non-occupational settings. Air pressure differences may also be monitored by one or more sensors and relayed to the smart device and displayed by the app.

In some embodiments, the app may provide audio assistance to users who are blind and cannot read the GUI. The audio assistance would read what is one the GUI to the user. The volume of the audio could be controlled for the hearing impaired. The app may be used to control video images or projections within the HCD.

The app may be configured to provide an intercom system with one or more users using a similar HCD system.

The app may be configured to provide filter end of useful life alerts to the user based on at least one of age of the filter, increased head pressure on the filter and optical readings indicating a dirty filter.

Variable Flow Head Covering Device (VFHCD)

The following embodiments relate to a variable flow head covering device (VFHCD) capable of negative, positive, or neutral air flow to provide a comfortable and controlled environment for a user.

Figure 20:
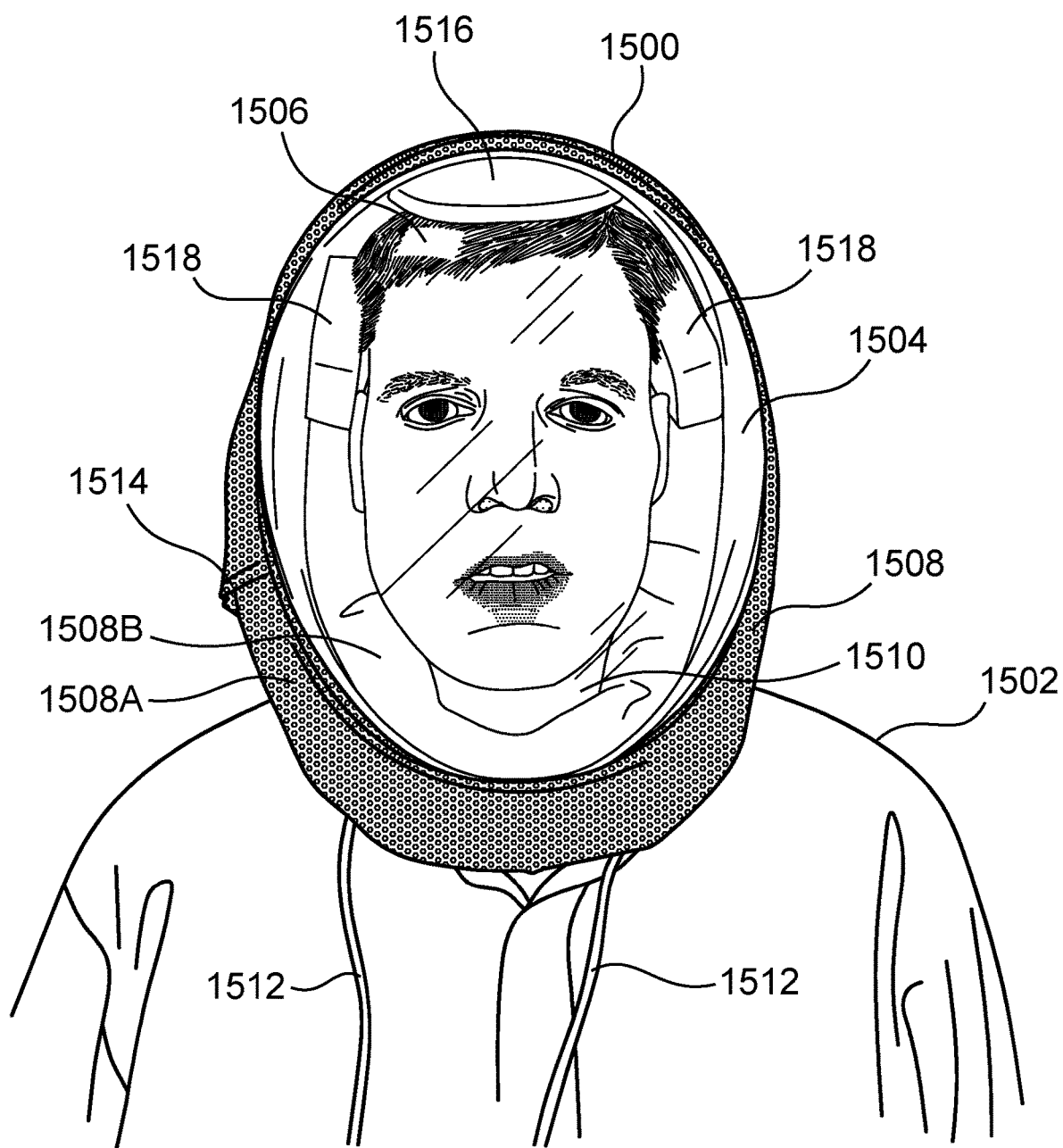
FIG. 20 is a front view of a user wearing a variable flow head covering device (VFHCD), according to an embodiment of the disclosure.

FIG. 20 is a front view of a user wearing a variable flow head covering device (VFHCD) 1500, according to an embodiment of the disclosure. A VFHCD 1500 is placed over the head of a user 1502. The VFHCD comprises a rigid frame 1504 and a rigid transparent face shield 1506. Frame 1504 may be constructed from a rigid or semi-rigid material. Frame 1504 is a hoop-like structure wherein the perimeter of the frame has a generally oval shape but may also be generally circular or some other appropriate shape, such as pear-shaped. Frame 1504 comprises a channel 1508. The edge of the face shield 1506 may be placed in and sit in the channel.

Frame 1504 may be constructed from a rigid polymer or metal or a combination thereof. The polymer may comprise fiberglass, carbon fiber, graphene, polyamide, polycarbonate (PC), polyester, high density or low density polyethylene, polyethylene terephthalate (PET), polypropylene (PP), polystyrene (PS), polyurethane, polyvinyl chloride (PVC), polyvinylidene chloride, acrylonitrile butadiene styrene (ABS), polymethylmethacrylate (PMMA), polytetrafluoroethylene (PTFE), phenolic, polyetheretherketone (PEEK), maleimide, bismaleimide, polyetherimide, polyimide, plastarch, furan, silicone, polysulfone, rubber, or a combination thereof. The frame may have a generally oval shape and circles a user's head, with a lower half passing below the user's chin and an upper half passing above a user's forehead.

The face shield 1506 is shaped as a hemi-ellipsoid and is preferably set close enough to the face of a user where the user's eyes are unable to focus on the inner surface of the face shield, and thus not interfere with the vision of the user. The face shield may be permanently attached to the frame 1504 or may be detachable from frame. If permanently attached, this may be accomplished by using an adhesive, thermal welding, or some other means. If detachable, the face shield may be held securely to the frame using an attaching device, such as a hook and loop fastener (Velcro®), clamps, clasps, magnets, screws, or other means.

The face shield may have a thickness in the range of about 0.05-0.25 inches. In the depicted embodiment, the face shield 108 has a thickness of about 0.125 inches. The face shield may be constructed from materials that are approved for impact resistance by the American National Standards Institute (ANSI). The face shield may be double-walled, preferably with a vacuum therebetween, for extra insulation. The face shield may comprise a scratch resistant coating or layer on the inner and/or outer surface to prevent abrasions or other damage. The face shield may comprise an anti-fogging coating on the inner or outer surface. A replaceable protective layer may be placed over the outer surface of the face shield. Naturally, the replaceable protective layer should comprise a transparent polymer.

A top portion of the transparent face shield may extend above a user's eyes, a bottom portion extends below the user's mouth and a first and second side portion extend beyond the user's side peripheral vision. The top portion of face shield may extend above a user's forehead and the bottom portion extends below the user's chin.

In a preferred embodiment, face shield 1506 is a rigid transparent polymer or glass. The polymer may comprise an acrylic such as polymethylmethacrylate. The polymer may comprise polystyrene (PS), polycarbonate, glycol modified polyethylene terephthalate (PETG), or cellulose acetate butyrate or a combination thereof. In some embodiments, the face shield is made from a laminate of polymeric films, each contributing to the structural or optical properties of the face shield. As an example, one layer of the laminate may be included to provide shatter resistance.

In some embodiments, the face shield further comprises an area in the line of sight for a user that provides eye correction and improved vision. The VFHCD may be able to project images on the internal surface of the face shield. For example, the VFHCD may be capable of AR for a user.

In other embodiments, the transparent face shield further comprises a mechanical wiper and motor to clear debris from the front surface of the face shield. In still other embodiments, the transparent face shield further comprises a vibrator to vibrate the face shield to clear debris from the front surface of the face shield. The vibrator may be an ultrasonic vibrator or a pneumatic hammer.

FIG. 20 also illustrates a view of a fabric component 1508. The fabric component may also be referred to as a neck skirt, neck seal, neck collar, or neck shroud. The fabric preferably fits snugly around the neck 1510 of a user 1502, such that particulates do not able to pass between the fabric and the neck of the user. The fabric may be flexible or stretchable and may be made of a polymer such as polyester, polypropylene, polytetrafluorethylene (PTFE), polyether ether ketone (PEEK), polyethene-co-chlorotrifluoroethene (E-CTFE), silicone, rayon, spandex, Lycra®, viscose, stretched polytetrafluoroethylene (PTFE), or nylon. The fabric may be made of a natural fabric such as cotton or wool, a composite of a natural fabric and a polymer, or a pharmaceutical grade textile.

As depicted, the fabric component 1508 is comprised of a single sheet of fabric. The single sheet of fabric, together with the transparent face shield and the frame, cover a user's entire head and a lower portion of the single sheet of fabric encircles the user's neck and forms a seal therewith. The fabric component comprises a drawstring 1512 to tighten around the neck of a user for better sealing properties. In some embodiments, it is preferred to include buttons on the drawstrings to hold the drawstrings in the tightened position. The drawstring is to facilitate the fabric component forming a seal around the user's neck. Alternatively, the single sheet of fabric may possess enough stretch to allow the device to be placed over the user's head while leaving the lower portion of the single sheet of fabric intact and still capable of forming a seal around the user's neck.

The fabric component shown in FIG. 20 comprises a portion 1508A that is permeable or porous to air and a portion 1508B that is impermeable to air. The impermeable portion may be substantially air-tight and does not cover the frame. The air permeable portion is stretched around the frame 1504, covers the air movers, and allows air to pass through. The fabric component can be releasably attached by stretching around the frame. The fabric component may comprise an elastic band to facilitate stretching around the frame. The air impermeable portion 1508B seals around the neck of a user. The air impermeable portion may be baggy and stretchable to allow a user to stretch the fabric with their hand to dab or scratch their face without breaking the seal around the use's neck. The air permeable and air impermeable portions may comprise materials of the same composition or different compositions. The air permeable and air impermeable portions may be joined by a seam. The fabric component may be removable and washable.

The fabric component 1508 may comprise two or more layers. For example, the air impermeable portion may comprise an inner softer second sheet of fabric located between the air impermeable portion and the skin of the user. The inner sheet may be soft, washable and absorbent.

The fabric component further comprises an access 1514. The access allows a user to access the controls to the device located on the frame underneath the fabric. The access may be a flap that can be opened and closed and secured shut with a zipper, hook and loop fastener, button, or other method. The access may be located anywhere on the fabric on the periphery of the frame.

In some embodiments, the fabric component or portion may comprise a small foam block or insert that a user can use to scratch their noses without having to remove the VFHCD. The foam block or insert may be mounted on the face shield or on the frame. In other embodiments, the fabric component comprises finger sockets that protrude into the facial area of the VFHCD. Finger sockets allow a user to insert their fingers without compromising the environment inside the VFHCD but yet allow the user to scratch or rub an itch. The fabric component may be baggy and stretchable enough for a user to scratch their nose or dab their face without breaking the seal around the user's neck.

As shown in FIG. 20, the VFHCD 1500 rests on top of the head of the user. A resting pad 1516 is placed at the top of the face shield 1506 that provides support and cushion between the device and the head of the user. The resting pad may comprise a cushion-like material such as cloth, foam, rubber, or other soft material and may be replaceable and washable. Multiple materials, sizes and/or shapes of removable resting pads may be available, so that the user can select the most comfortable one for their size and shape of head.

Also shown in the VFHCD in FIG. 20 are earpieces 1518 to reduce noise, and dampen sound, and reverberations inside of the device as previously described herein. In a preferred embodiment, the earpieces are placed in front of the ears. As with the resting pad, multiple materials, sizes and/or shapes may be available and adaptable to provide comfort to the user depending on the shape and size of their head.

Figure 21:
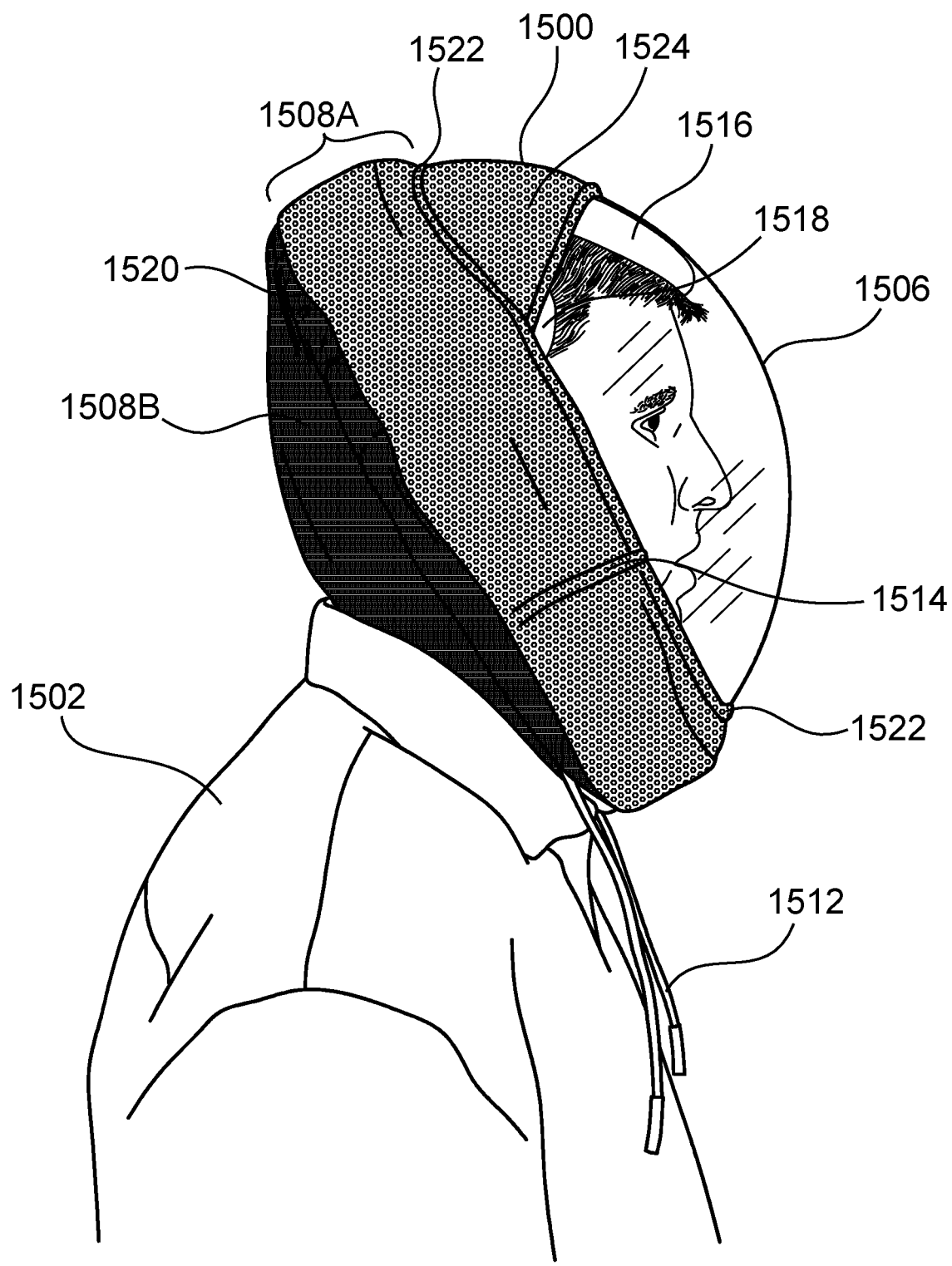
FIG. 21 is a side view of a user wearing a variable flow head covering device (VFHCD), according to an embodiment of the disclosure.

FIG. 21 is a side view of a user wearing a variable flow head covering device (VFHCD) 1500, according to an embodiment of the disclosure. This view further illustrates how the fabric component 1508 is composed of an air permeable portion 1508A and an air impermeable portion 1508B. The fabric component further comprises a first seam 1520 that connects the air permeable portion to the air impermeable portion. The fabric component further comprises a second seam 1522 that connects the air permeable portion 1508A to a top portion 1524 of the fabric. The seams may comprise an elastic material to hold the fabric securely onto the frame. The top portion of the fabric 1524 also aids in preventing the fabric from slipping off the frame. The top portion may be permeable or non-permeable. The first seam 1520 helps to form a seal around the bottom of the frame to prevent air in the neck from escaping that does not pass through a filter.

Figure 22:
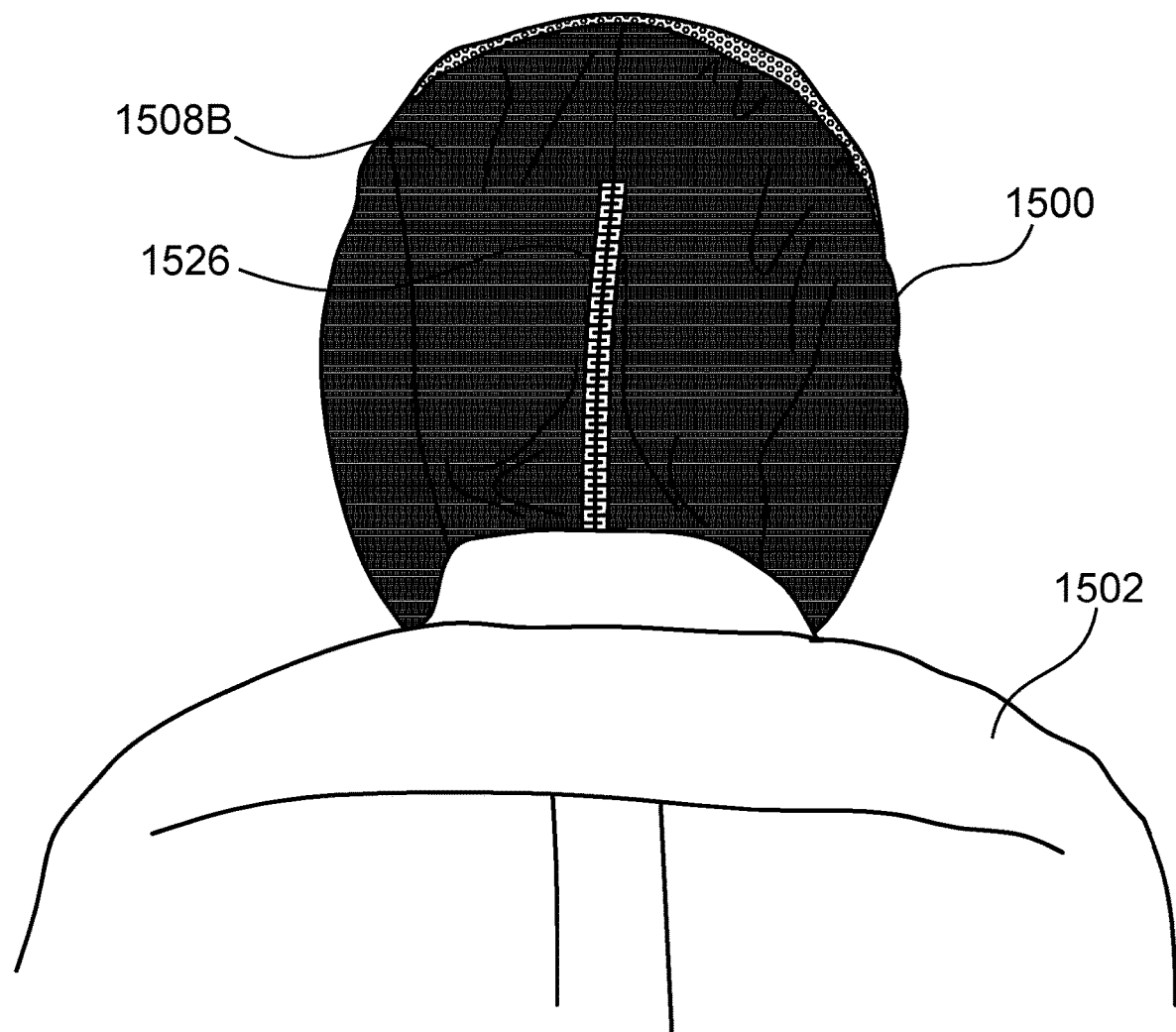
FIG. 22 is a rear view of a user wearing a variable flow head covering device (VFHCD), according to an embodiment of the disclosure.

FIG. 22 is a rear view of a user wearing a variable flow head covering device (VFHCD) 1500, according to an embodiment of the disclosure. This view illustrates how the device may be designed so that it can opened and closed without messing up the hair or makeup of a user. This embodiment comprises a zipper 1526. When the zipper is unzipped, allows the device to be fit over the user's head, and when zipped facilitates the fabric component forming a seal around the user's neck. Other embodiments may comprise an ultra-stretchable fabric that can be opened widely enough to not mess up the hair or makeup of a user.

Figure 23:
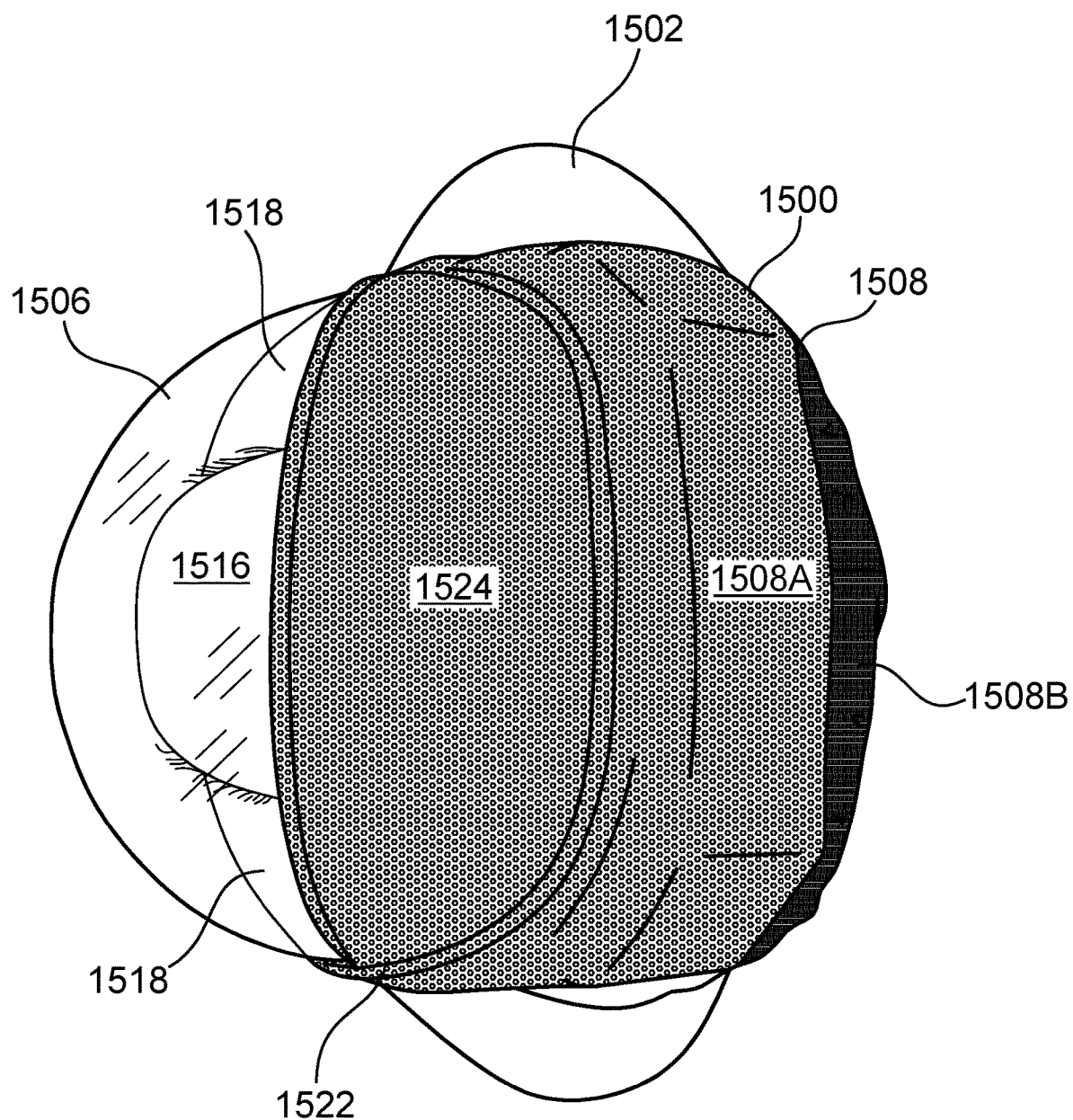
FIG. 23 is an overhead view of a user wearing a variable flow head covering device (VFHCD), according to an embodiment of the disclosure.

FIG. 23 is an overhead view of a user wearing a variable flow head covering device (VFHCD) 1500, according to an embodiment of the disclosure. This view further illustrates how the fabric component 1508 is secured over the frame. The top portion 1524 of the fabric extends over the face shield 1506. The resting pad 1516 extends over the top of the head of the user 1502.

Figure 24:
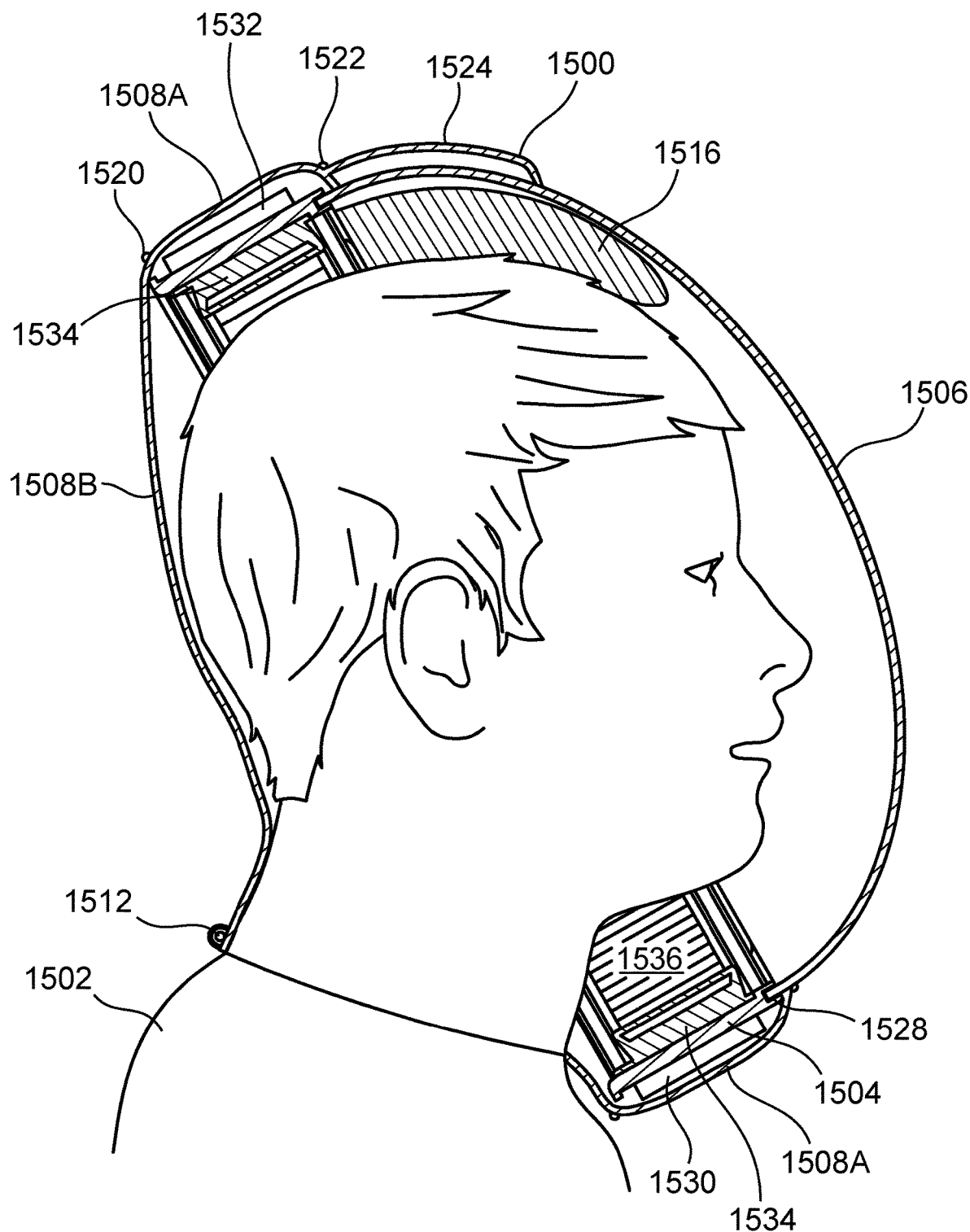
FIG. 24 is a cross-sectional view of a user wearing a variable flow head covering device (VFHCD), according to an embodiment of the disclosure.

FIG. 24 is a cross-sectional view of a user wearing a variable flow head covering device (VFHCD) 1500, according to an embodiment of the disclosure. This view better illustrates the frame and other components of the VFHCD. The face shield sits in a channel 1528 in the frame 1504. The channel runs along the top edge of the frame. The face shield may be reversibly removed from or placed in the channel.

Mounted to the frame is an air mover 1530. The air mover may be a fan or other air moving device as previously described herein. In this embodiment, the air mover may be located near the mouth of a user or may be mounted at any other location on the frame. The frame may comprise one or more air moving devices. The air mover moves air into or out of a port in the frame. The air mover is powered by one or more batteries in a battery pack 1532 that is also mounted to the frame. The battery pack may be mounted at any location on the frame, such as the upper portion of the frame.

The VFHCD further comprises a filter assembly 1534 located on the inside of the frame. In other embodiments, the filter assembly may be located on the outside of the frame. The filter assembly further comprises a filter 1536. The filter assembly can be connected to the frame by hook-and-loop fasteners, clips, snaps, channels, or other mechanism. In a preferred embodiment, the filter assembly can be reversibly removed or attached to the frame. The VFHCD may comprise two or more filter assemblies. The filter is to filter incoming air or outgoing air from inside the device.

Figure 25:
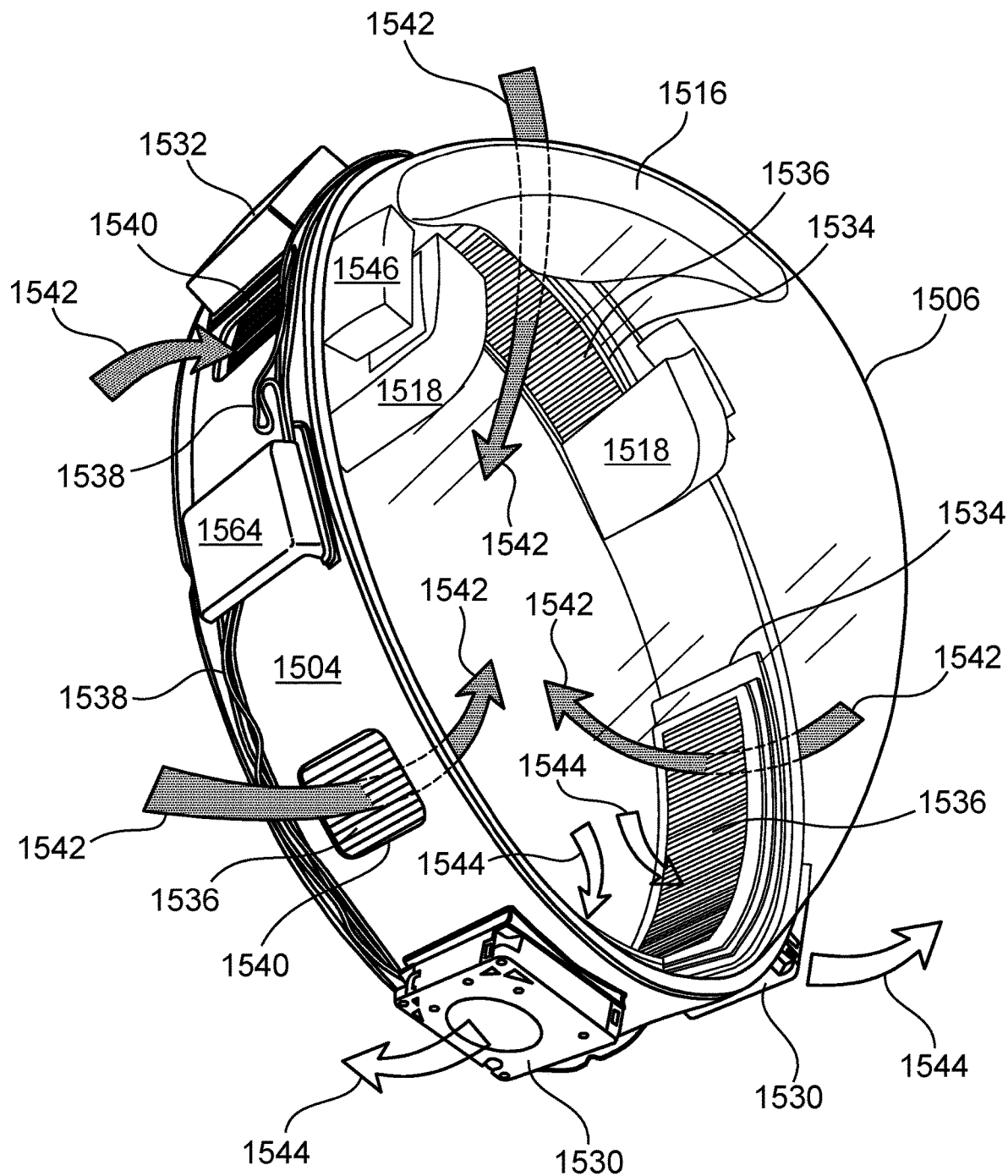
FIG. 25 is a perspective view of the variable flow head covering device (VFHCD) without the fabric and illustrating negative air flow, according to an embodiment of the disclosure.

FIG. 25 is a perspective view of the variable flow head covering device (VFHCD) 1500 without the fabric and illustrating negative air flow, according to an embodiment of the disclosure. This view further illustrates the components of the VFHCD that are typically hidden from view when the fabric component is stretched over the frame 1504. The fans 1530 and battery pack 1532 are mounted to the outer surface of the frame and are in electronic communication with the control box 1564 via electrical wiring 1538. The control box comprises an on/off air mover switch, charge port, and LED (light emitting diode) indicator lights. The control box may comprise other controls to operate components of the VFHCD such as lights, sensors, or air mover speeds.

FIG. 25 further illustrates a port 1540 in the frame. The port may be an air inlet or air outlet port. There may be one or more ports. Air may move into or out of the ports depending on how the air movers 1530 are designed. An air mover may be placed over one, two, three, four, five or all six of the ports in the frame to assist the movement of both inlet and exhaust air. Some air movers may pull air into the device and some air movers push air out of the device. For example, two air movers may pull air out of the device while another two air movers may push air into the device. In another embodiment, two air movers may pull air out of the device while another four air movers my push air into the device. Other combinations of air movers may be used to pull air into the device and push air out of the device.

As illustrated in FIG. 25, air movers, such as fans, can pull air from inside the VFHCD device through the fans to outside of the device forming a negative air flow. This is illustrated by arrows 1544 that pass through a filter 1536 in a filter assembly 1534. The air that enters the device passes through a filter 1536 located in an intake port 1540 (also referred to herein as an inlet port and used interchangeably). Air that is in the device and exhaust air from a user may be exhausted through a filter and out an air mover 1530. This exhaust air is represented by arrows 1544. Each fan is situated directly over a port. There are twice as many additional ports as ports that are situated over the fans. As illustrated in FIG. 25, there are two fans attached to the frame and each fan is located over a port. There are an additional four more ports 1540 to allow for unrestricted air flow that are not located over a fan. Only two are in view in FIG. 25 as the other two are hidden by the filter assemblies. Two fans pull air out of the device through to exhaust ports and filters, while air enters the device through four intake ports and intake filters.

In some embodiments, the air movers may comprise a pressure sensor and a processor receiving input from the pressure sensor. The pressure sensor and processor can be adapted to increase or decrease power to the air mover to thereby regulate the pressure inside the head covering device. In some instances, the user may desire to have neutral air flow in addition to negative or positive air flow. The sensor and processor may be used to control and regulate the desired air flow.

In some embodiments, the inlet port or exhaust port further comprises filter covers to reduce noise entering or exiting the VFHCD 1500. In some embodiments, the fans may be attached with a resilient mount to the frame to reduce noise and vibration.

The filters 1536 located over the air inlet and outlet ports are pleated. This increases the surface are of the filter to increase filtering efficiency and to prevent air flow from being restricted. The surface area of the filters in the device may be greater than 50 inch$^2$. In other embodiments, the surface area of the filters in the device may be greater than 100 inch$^2$. In a preferred embodiment, the surface area of the filters in the device may be greater than 200 inch$^2$. In other embodiments, the filters may not be pleated.

The inlet filter is adapted to block the passage of a virus, bacteria, smog, noxious gas, poisonous gas, smoke, or a combination thereof, to purify the incoming air for a user. The outlet filter may also filter the exhaust air. This is beneficial if a user has an infectious disease which would prevent non-wearers of the VFHCD from being infected. This device could be used in a hospital, nursing home, or other facility by an infected nurse, doctor, or other health care worker without the risk of infecting the patients that they are treating that may have compromised immune systems. The filters can be readily changed depending on the environment where the device is being used. In a preferred embodiment, the filter is a HEPA filter.

Also shown in FIG. 25 are the earpieces 1518 and how they are attached to the face shield. The earpieces are attached to a mount 1546 that is further attached to the face shield. The earpieces can be reversibly removed and reattached to the mounts such as when they may need to be washed or replaced. The earpieces may be attached by hook-and-loop fasteners, an adhesive, snaps, or other mechanism.

Figure 26:
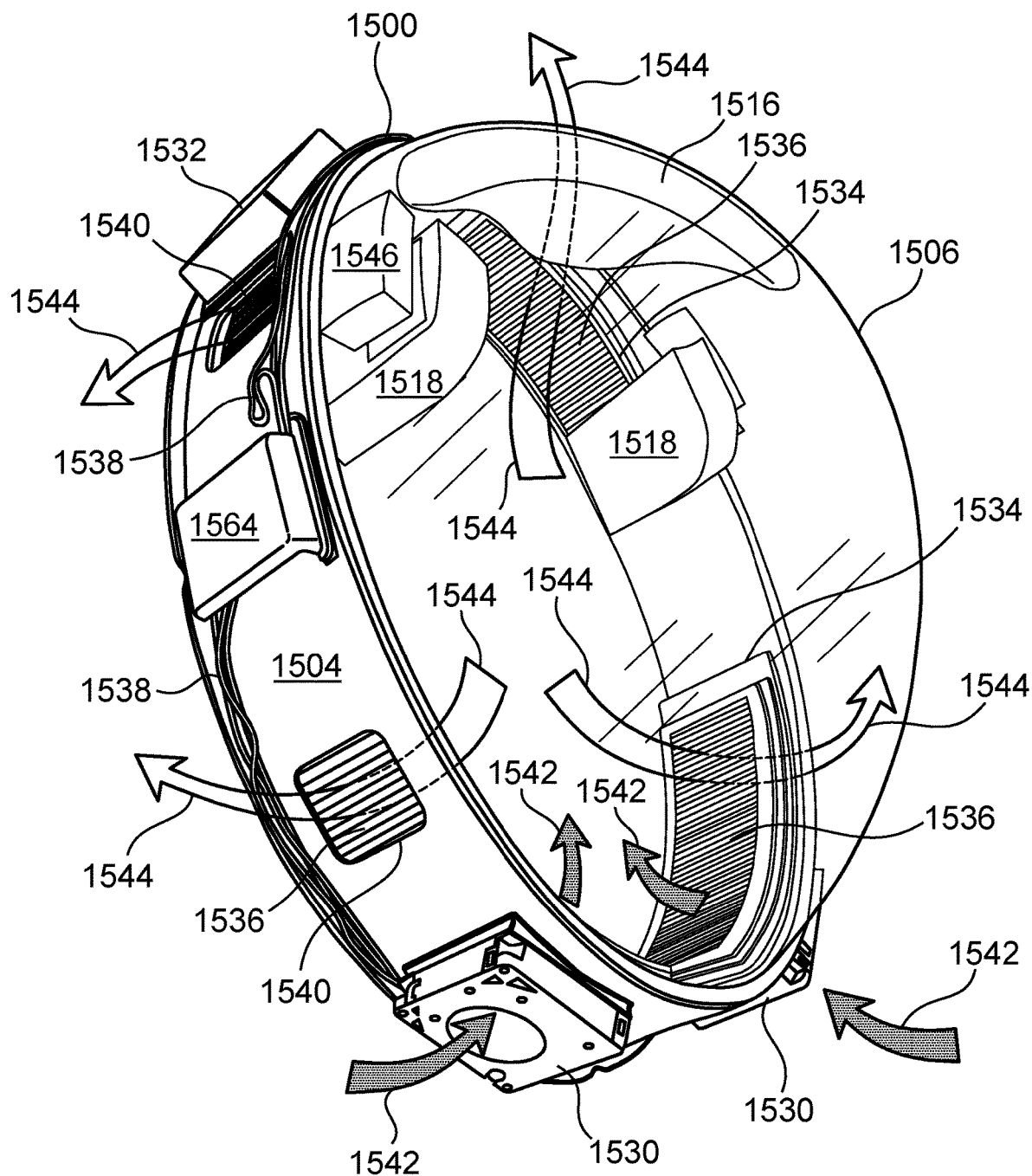
FIG. 26 is a perspective view of the variable flow head covering device (VFHCD) without the fabric and illustrating positive air flow, according to an embodiment of the disclosure.

FIG. 26 is a perspective view of the variable flow head covering device (VFHCD) 1500 without the fabric and illustrating positive air flow, according to an embodiment of the disclosure. As illustrated in FIG. 26, air movers, such as fans, can pull ambient air into the VFHCD device through the fans from outside of the device forming a negative air flow. This is illustrated by arrows 1542. The air that enters the device passes through a filter 1536 located in a filter assembly 1534. Air that is in the device and exhaust air from a user may be exhausted through a filter and out an air outlet 1540. This exhaust air is represented by arrows 1544. Each fan is situated directly over a port. There are twice as many additional ports as ports that are situated over the fans. As illustrated in FIG. 26, there are two fans attached to the frame and each fan is located over a port. There are an additional four more ports 1540 to allow for unrestricted air flow that are not located over a fan. As explained previously herein, many different combinations of air movers may be used that pull air in the device or pull air out of the device.

Figure 27:
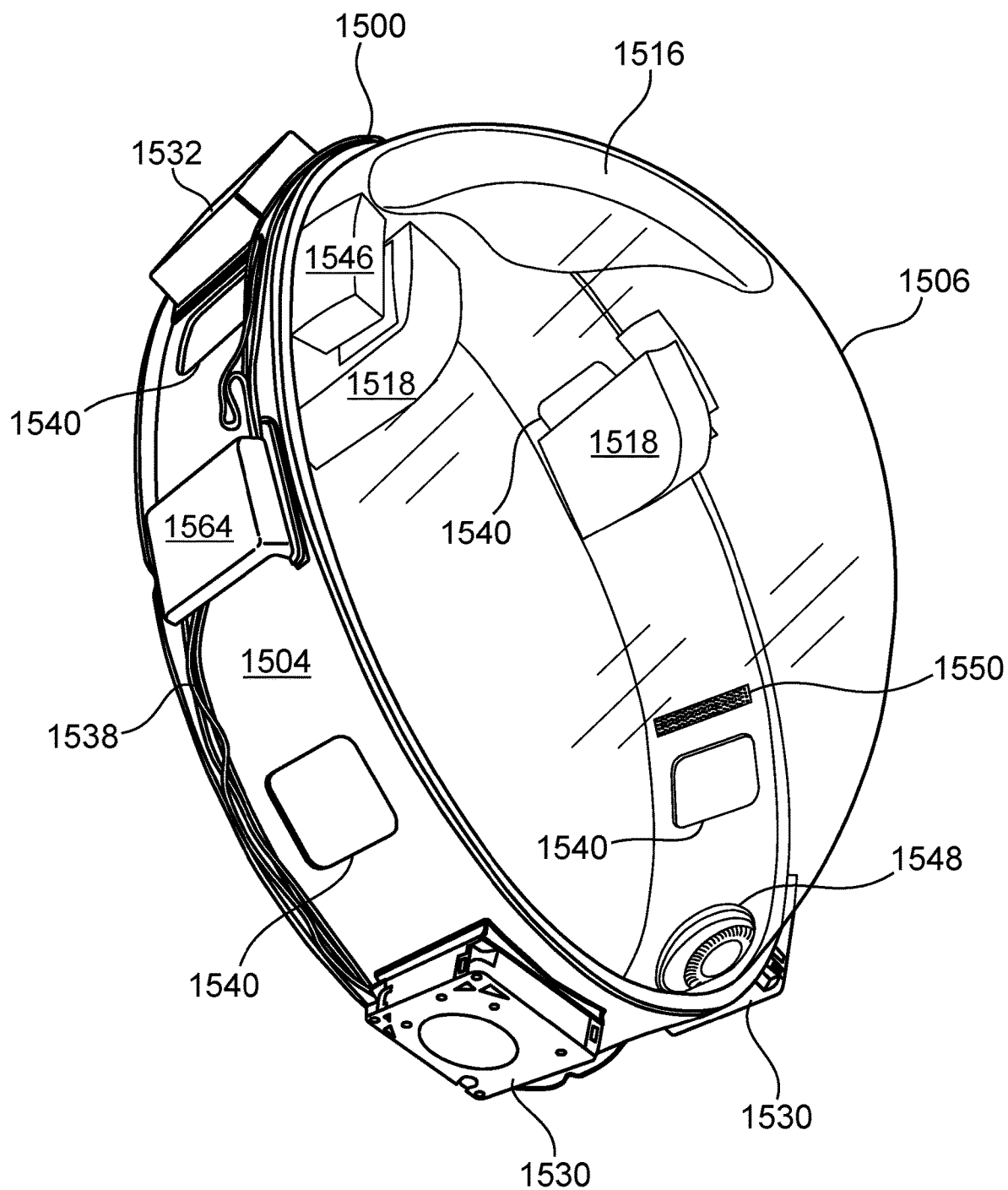
FIG. 27 is a perspective view of the variable flow head covering device (VFHCD) without the fabric and filter assemblies, according to an embodiment of the disclosure.

FIG. 27 is a perspective view of the variable flow head covering device (VFHCD) 1500 without the fabric and filter assemblies, according to an embodiment of the disclosure. Also shown in this view, inlet and outlet ports can be seen. A circular port 1548 can be seen that is located next to a fan 1530. The port may also be square or rectangular-like in shape. Also shown is a hook and loop fastener strip 1550 on the inner side of the frame to where a filter assembly may be attached to. Other devices may be used to attach the filter assembly.

Figure 28:
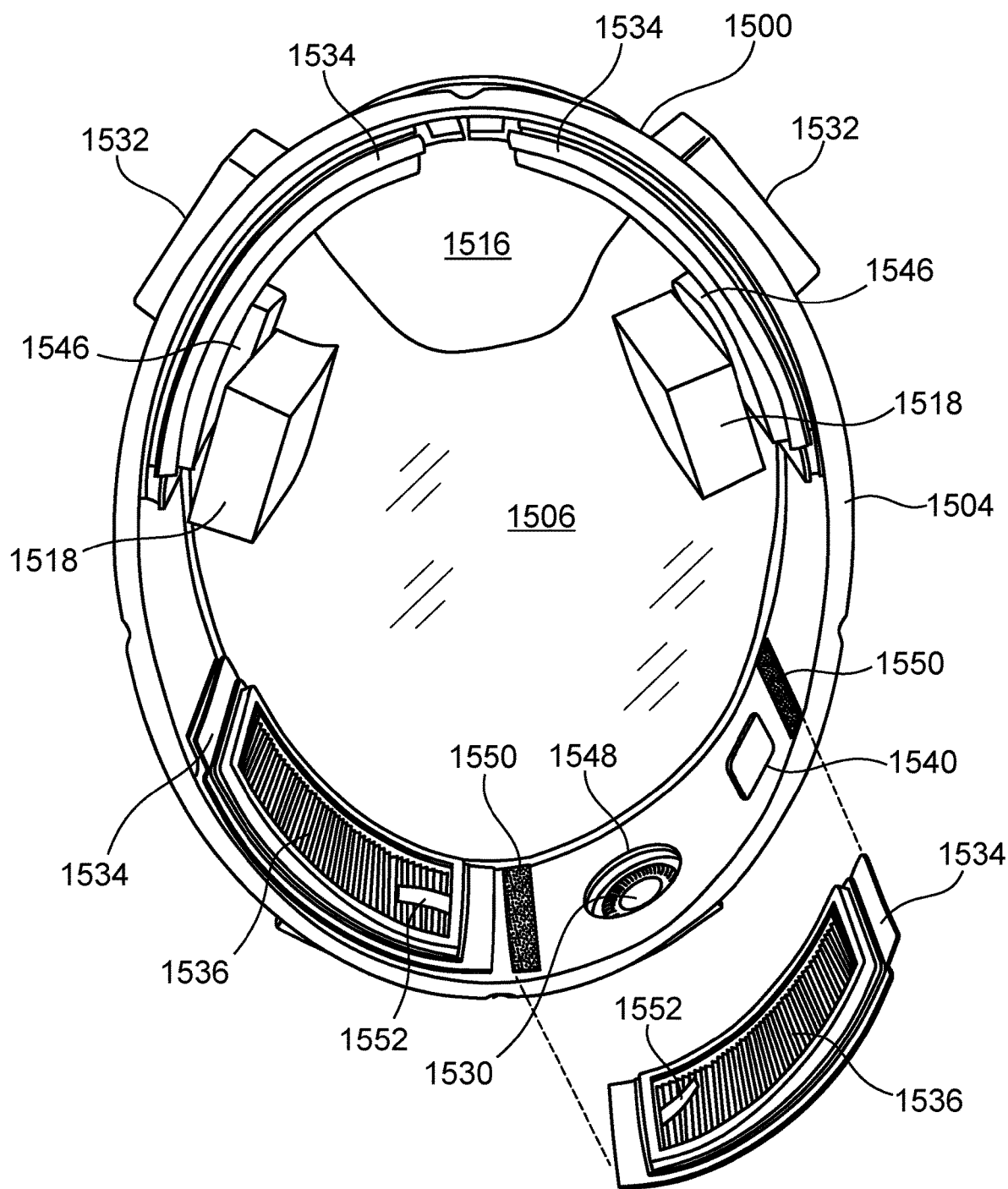
FIG. 28 is a bottom view of the underside of the variable flow head covering device (VFHCD) without the fabric and showing how the filter assemblies are attached, according to an embodiment of the disclosure.

FIG. 28 is a bottom view of the underside of the variable flow head covering device (VFHCD) 1500 without the fabric and showing how the filter assemblies are attached, according to an embodiment of the disclosure. In this view, a filter assembly 1534 has been removed and showing how it sits in the frame as one of four filter assemblies. A hook and loop fastener strip is located on either side of the ports 1540, 1548. Each of the filter assemblies near the bottom of the frame nearest the mouth of a user spans both ports. The filter assemblies at the top of the frame only span a single port 1540. The filter assemblies may be reversibly removed and reattached.

The filter assemblies further comprise a tab 1552. The tab may be used to grab and pull the filter assembly off the hook and loop fastener strips and away from the frame. The filter assemblies have a radius of curvature similar to the radius of curvature of the frame in order to form a uniform distance along the length of the filter assembly between the filter assembly and the frame.

Figure 29:
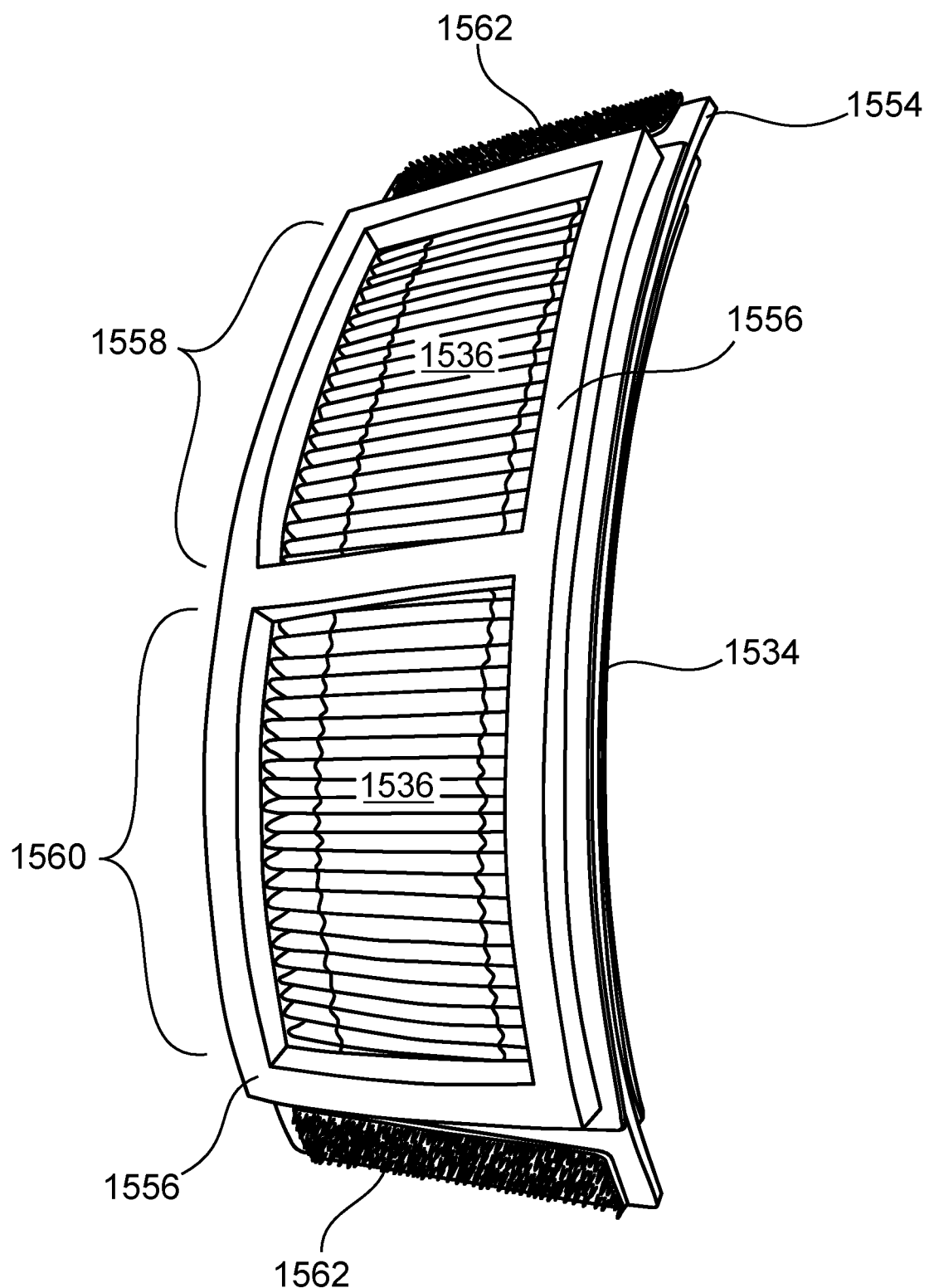
FIG. 29 is a close-up view of a filter assembly, according to an embodiment of the disclosure.

FIG. 29 is a close-up view of a filter assembly 1534, according to an embodiment of the disclosure. The filter assembly comprises a rigid support 1554. The support may comprise a polymer such as polystyrene (PS), high or low density polyethylene, polypropylene (PP), polyacrylonitrile, acrylonitrile butadiene styrene (ABS), polyvinyl chloride (PVC), polycarbonate (PC), polyethylene terephthalate (PET), polytetrafluoroethylene (PET), polymethylmethacrylate (PMMA), polyetheretherketone (PEEK), polyamide, polyimide, or a combination thereof. The support may comprise a metal such as aluminum. The filter assembly comprises a compartment further comprising a filter 1536 that spans the length of the assembly.

The filter assembly further comprises a gasket 1556. The gasket is preferably a soft and flexible material that can form a seal between the filter assembly and the surface of the frame. The gasket may comprise a foam rubber-like material. The gasket can be designed to form a first area 1558 and a second area 1560 wherein the first area is divided from the second area. The first area covers an inlet port and the second area covers an outlet port in the frame. The gasket can substantially prevent inlet air from entering an outlet port and outlet air from entering the inlet port.

The filter assembly further comprises an attaching device to attach the filter assembly to the inner surface of the frame. In a preferred embodiment as illustrated in FIG. 28, the attaching device is a hook-and-loop fastener such as a hook and loop fastener strip 1562. Strip 1562 connects to a receiving strip 1550 located on the frame.

Figure 30:
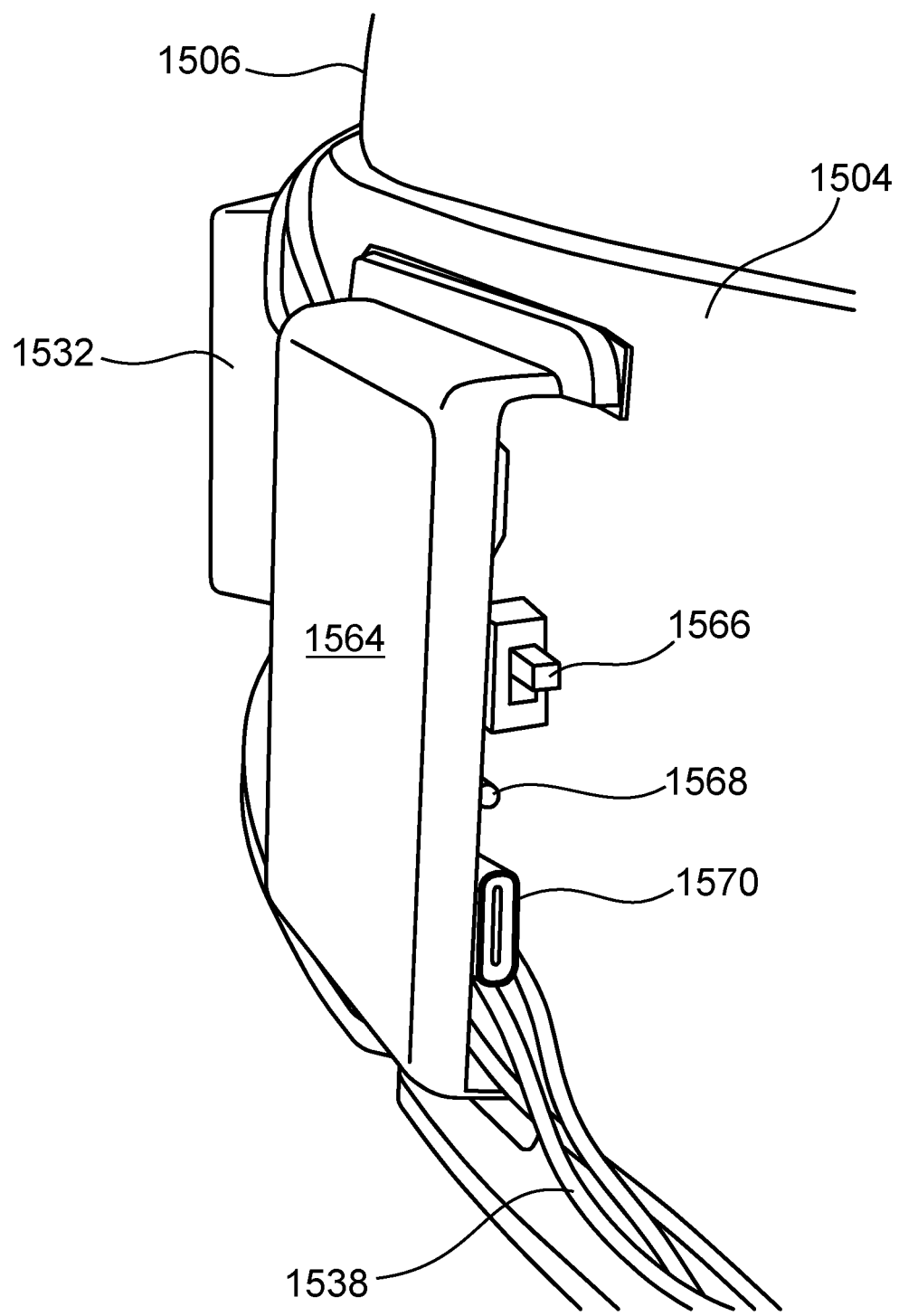
FIG. 30 is a close-up view of the control box, according to an embodiment of the disclosure.

FIG. 30 is a close-up view of the control box 1564, according to an embodiment of the disclosure. The control box is in electrical communication with a battery pack and an air mover. The control box comprises an on/off air mover switch 1566, LED indicator light 1568, and charge port 1570. Other controls may be in the control box such a flow or pressure sensor, an air flow controller, or a combination thereof to control other components of the device. In a preferred embodiment, the charge port to recharge the batteries in the battery pack is a USB-C plug. The charge port may be a USB-A, USB 3.0 A SS, USB B, USB 3.0 B SS, USB mini-A, USB mini-AB, USB mini-B, USB micro-AB, USB micro-B, or a USB 3.0 micro-B SS plug.

Figure 31:
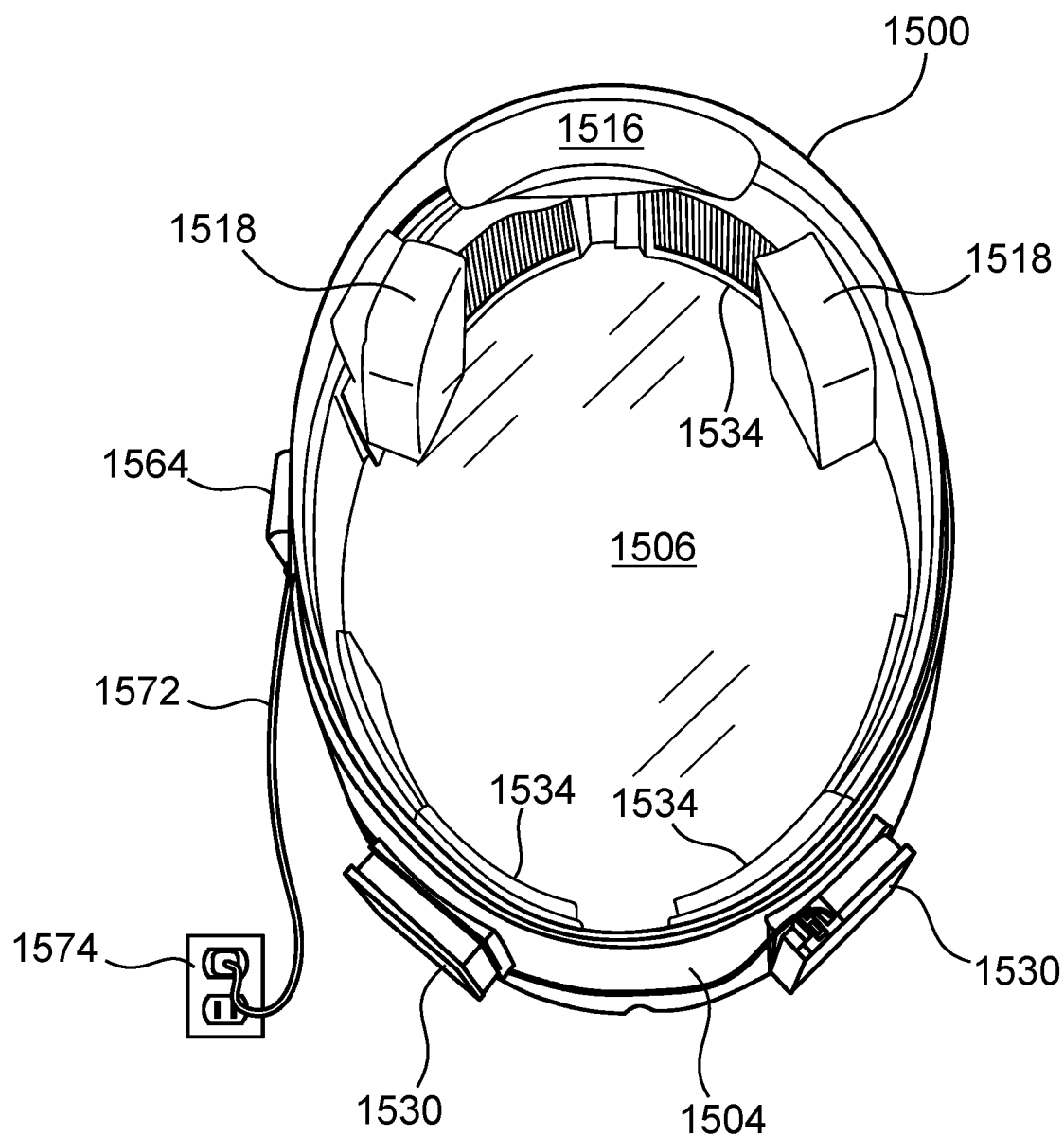
FIG. 31 is a view of the variable flow head covering device (VFHCD) being charged, according to an embodiment of the disclosure.

FIG. 31 is a view of the variable flow head covering device (VFHCD) being charged, according to an embodiment of the disclosure. In a preferred embodiment, the battery pack 1532 comprises one or more rechargeable batteries. The rechargeable batteries may comprise a rechargeable Li ion-based battery such as a $LiCoO_2$, $LiFePO_4$, $LiMnNiCoO_2$, $LiNiCoAlO_2$, or $LiMn_2O_4$-based battery. The rechargeable batteries may comprise a nickel-cadmium or nickel metal hydride battery. FIG. 31 illustrates a charge cord 1572 connecting to the charge port 1570 in the control box 1564 of the VFHCD to a wall socket 1574. The fabric component 1508 has been removed to better illustrate charging. When the fabric component is stretched over the frame, a charge cord may be connected to the charge port in the control box by way of access 1514 previously described herein. In other embodiments, the battery pack may comprise a non-rechargeable primary battery such as an alkaline cell.

Alternative Fan Location in a Variable Flow Head Covering Device (VFHCD)

The following embodiments illustrate alternative locations for the fans in a variable flow head covering device (VFHCD).

Figure 32:
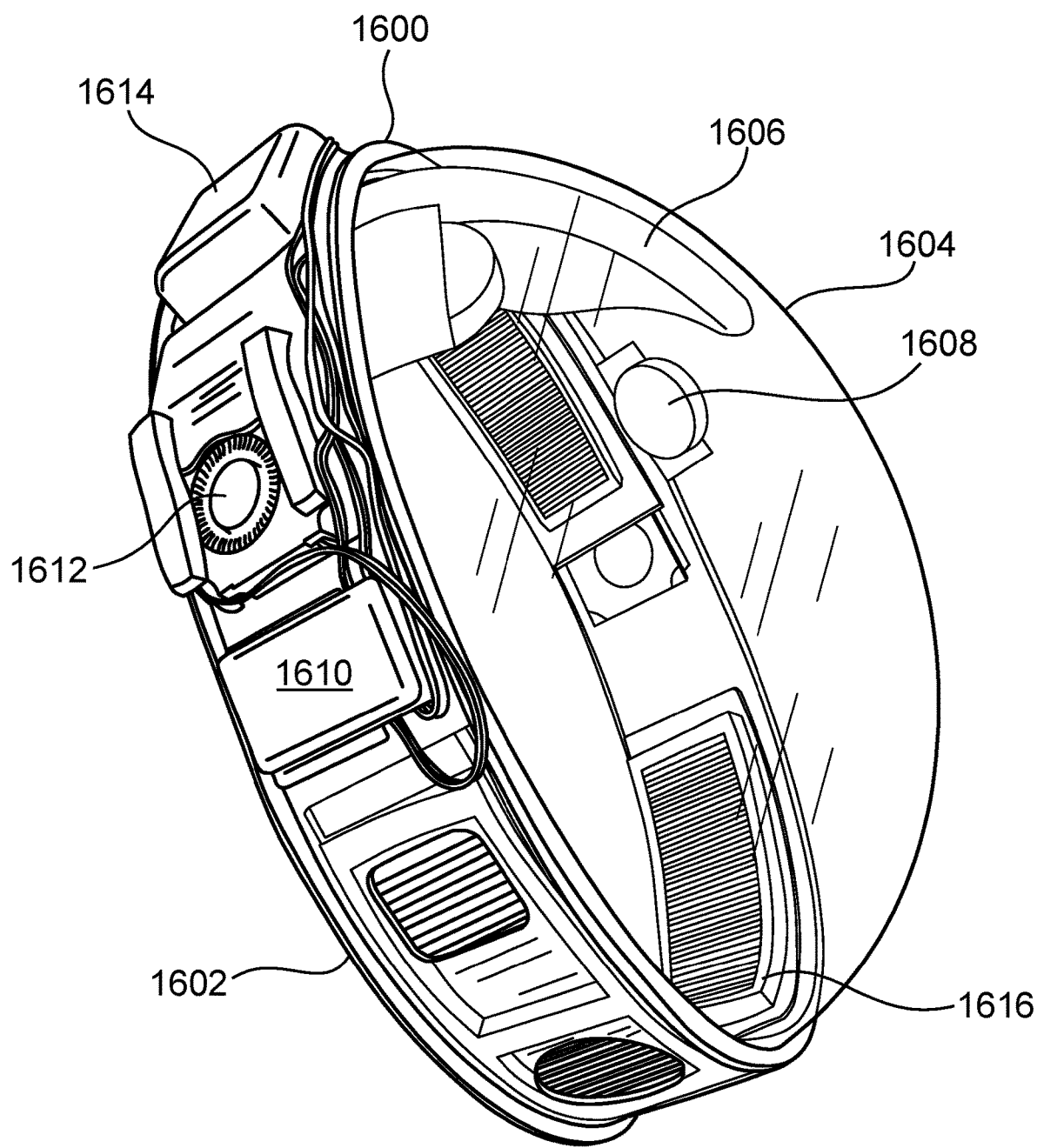
FIG. 32 is a view of a variable flow head covering device (VFHCD) with alternative fan locations, according to an embodiment of the disclosure.

FIG. 32 is a view of a variable flow head covering device (VFHCD) 1600 with alternative fan locations, according to an embodiment of the disclosure. VFHCD 1600 is similar to the disclosed VFHCD 1500 embodiment described previously herein. The VFHCD 1600 embodiment in FIG. 32 does not include a fabric component in order to better view where the fans are placed. VFHCD 1600 similarly includes a frame 1602, transparent face shield 1604, resting pad 1606, earpieces 1608, control box 1610, fans 1612, battery pack 1614, and filter assembly 1616.

In this embodiment, the fans 1612 are moved towards the top of the frame near the battery pack. In the VFHCD 1500 embodiment they are near the mouth of the user. By moving the fans toward the top of the frame, the weight distribution of the device is improved in the VFHCD 1600 embodiment.

Flip Up Face Shield for a Variable Flow Head Covering Device (VFHCD)

The following embodiments describe a design of a VFHCD with a face shield that can easily be opened and closed for access to the face of a user.

Figure 33:
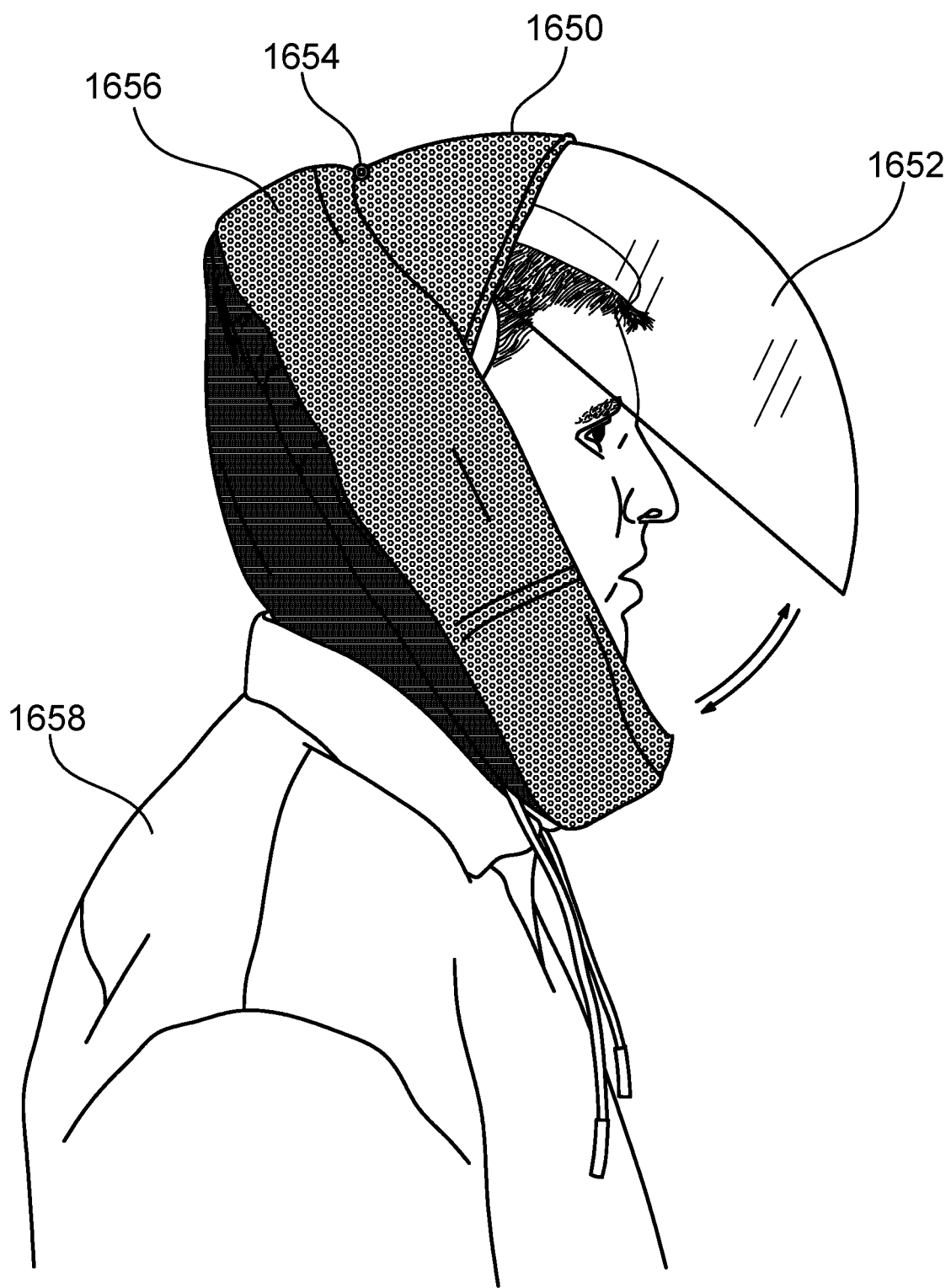
FIG. 33 is a side view of a user wearing a variable flow head covering device (VFHCD) with an opened face shield, according to an embodiment of the disclosure.

FIG. 33 is a side view of a user wearing a variable flow head covering device (VFHCD) 1650 with an opened face shield, according to an embodiment of the disclosure. The face shield 1652 is connected by a movable joint, such as the depicted simple hinge 1654, underneath the fabric component 1656 to allow for the face shield to be easily opened without removing the face shield entirely from the VFHCD. Alternatively, the movable joint may be a fabric, strap hinge, butt hinge, concealed hinge, plano hinge, offset hinge, overlay hinge, hidden barrel hinge, or a scissor hinge. In a preferred embodiment, the movable joint is a spring-loaded hinge. The spring-loaded hinge can hold the face shield open without the user having to do so. The face shield can be readily opened and closed for quick access to the face of a user 1658. The face shield may be able to snap in and out of the frame as it is opened and closed to secure the face shield. The fabric may be flexible or slide up the face shield to allow for opening of the face shield.

In other embodiments, the moveable joint may be located at the bottom of the face shield and connected to the bottom of the frame. The moveable joint may be located on either side of the face shield such that the face shield can be opened from the right or left of the user. Preferably, the VFHCD 1650 includes a latch or other locking means, such as magnets, to keep the face shield in place when not opened.

Automatic Air Mover for a Variable Flow Head Covering Device (VFHCD)

The following embodiments relate to air movers that automatically start when a user places a VFHCD over their head. The air mover automatically turns off when the user removes the VFHCD. The air mover may also adjust according to a pre-determined threshold.

Figure 34:
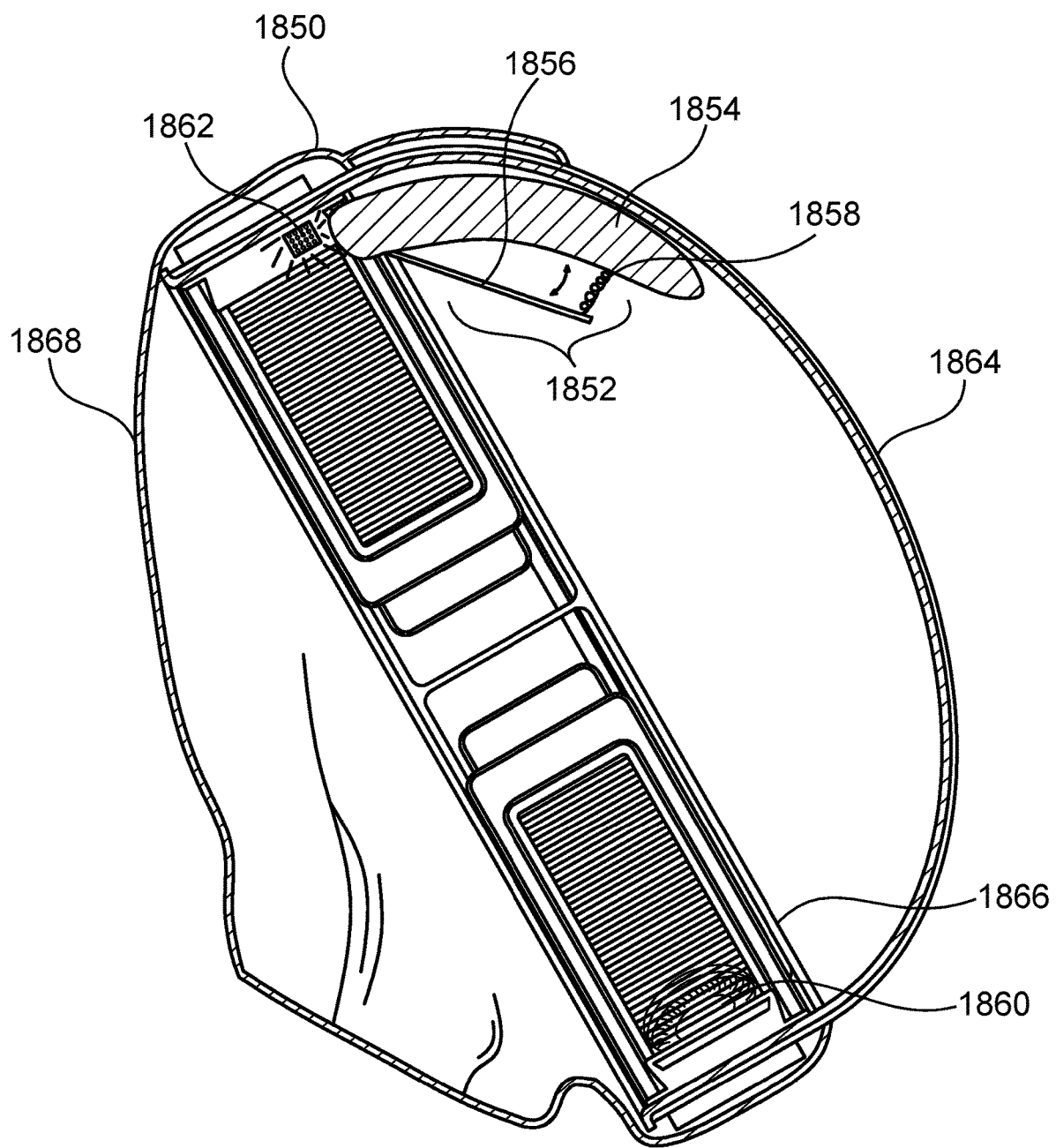
FIG. 34 is a cross-sectional view of a variable flow head covering device (VFHCD) 1850 equipped with an automatic air mover, according to an embodiment of the disclosure.

FIG. 34 is a cross-sectional view of a variable flow head covering device (VFHCD) 1850 equipped with an automatic air mover, according to an embodiment of the disclosure. VFHCD 1850 embodiment comprises a spring-loaded lever switch 1852. The lever switch is located at the top of the VFHCD near head resting pad 1854. The lever switch comprises a lever 1856. The lever switch further comprises a resilient device, such as the depicted spring 1858. In an exemplary embodiment, the lever may be a part of resting pad. The lever may protrude out of the resting pad such that when it is depressed, it retracts into the resting pad such that when a user places the device on, the user cannot feel the lever. The user instead feels the resting pad to provide a comfortable experience.

When the VFHCD 1850 is placed on the head of a user, the lever is depressed and pushed into the resting pad (such as a resting pad cavity) or other location so that it is not uncomfortable to a user. By depressing the lever, the pressure switch completes an electrical circuit such that power from battery pack comprising one or more batteries or other power source provides an electrical current to an air moving device, such as a fan 1860. The air mover then automatically turns on. When a user removes the device from their head, the lever is extended by the spring which breaks the electrical circuit between the air mover and power source which automatically shuts down the air mover.

VFHCD 1850 preferably comprises one or more sensors 1862. The sensor can detect the head of a user and sends a signal to turn on the air mover. The sensor may be a temperature sensor, pulse rate sensor, IR sensor, optical sensor, humidity sensor, proximity sensor, motion sensor, skin moisture sensor, force sensor, or a biometric sensor. Upon detection of the head of the user placing the device on, the automatic air mover turns on. This may be done by measuring the temperature of a user or a proximity sensor of a nearby object, such as the head of a user. When the device is removed, the sensor no longer detects the head of a user and the air mover then turns off. The sensor may be located anywhere within the VFHCD, such as on the face shield 1864, in the frame 1866.

The sensor may detect a change in the biometric data of a user which may be relayed to a controller. The controller would then adjust the air flow from an air mover until a pre-determined biometric data target is reached. The biometric data may include skin temperature, pulse rate, skin moisture, or oxygen saturation. A processor may also be combined to process the signals from the sensors.

The VFHCD may further comprise a controller that is configured to adjust the rate at which the air mover moves air. A sensor detects the air flow. When the air flow falls below a pre-determined threshold of air flow, the sensor relays the information to a controller that adjusts the rate of air flow from an air mover. The air mover increases the air flow until the threshold is reached. In some instances, the air flow may rise above a pre-determined threshold such that the controller decreases the air flow. The VFHCD further comprises a sensor for generating signals indicative of at least one of air pressure, ambient temperature, body temperature, skin moisture, blood oxygen saturation, respiration rate and pulse rate, and a processor for processing signals from the sensor and providing instructions to the controller to adjust the rate of the air mover according to predetermined parameters.

The HCD may further comprise a communication module for receiving signals relating to at least one of air pressure, ambient temperature, body temperature, skin moisture, blood oxygen saturation, respiration rate and pulse rate, and a processor for processing signals from the communication module and providing instructions to the controller to adjust the rate of the air mover according to predetermined parameters. The communication module is configured to receive signals from the user's smart device. The device is configured to communicate with an app running on a user's smart device, which app is configured to provide alerts to the user and to allow the user to adjust the rate of the air mover. The communication module is configured to receive signals from the user's wearable smart device.

The VFHCD may further comprise a sensor for generating signals indicative of the concentration of oxygen, and a processor for processing signals from the sensor and providing instructions to the controller to increase the rate of the air mover when the oxygen concentration of oxygen falls below a predetermined level. The device further comprises a user warning system, configured to alert the user when the concentration of oxygen falls below the predetermined level.

The VFHCD further comprises a sensor for generating signals indicative of the concentration of carbon dioxide, and a processor for processing signals from the sensor and providing instructions to the controller to increase the rate of the air mover when the concentration of carbon dioxide rises above a predetermined level. The device further comprises a user warning system, configured to alert the user when the concentration of carbon dioxide rises above the predetermined level. The device further comprises a second sensor for generating signals indicative of the concentration of oxygen, and wherein the processor processes signals from the sensor and the second sensor and provides instructions to increase the rate of the air mover when either the concentration of carbon dioxide rises above a predetermined level or the concentration of oxygen falls below a second predetermined level.

The VFHCD may further comprise two or more electrodes. The electrodes may be located in the fabric 1868, in the resting pad 1854, or elsewhere in the device where the skin of the user comes into contact with the electrodes. By coming into contact with the electrodes, the circuit is closed and a current is able to pass. This current is detected by a sensor that initiates the starting of the air mover.

In some embodiments, the air moving device may be combined with a head covering device that comprises a flip-up shield. The flip-up shield may be connected by a hinge to the frame, as previously illustrated herein in FIG. 33. The air moving device may shut off when the shield is flipped open by the user. The air mover may turn on when the shield is closed.

Shroud for Variable Flow Head Covering Device (VFHCD)

The following embodiments include a shroud-like component that can at least partially cover the transparent face shield in a VFHCD when a user desires to have a darkened environment to relax, sleep, or for enhanced privacy. In some embodiments, the shroud completely covers the transparent face shield, while in others, the shroud only partially covers the transparent face shield, so as to provide privacy, while allowing some light inside the device.

Any of the variable flow head covering device (VFHCD) 1500,1600 embodiments described may also be equipped with a shroud, such as shroud 700 shown in FIG. 12. A user wearing a VFHCD can place or slip the shroud over the HCD. The shroud comprises a flexible, stretchable, or stiff fabric and may also be referred to as a cover, blackout cover, sleep cover, or privacy cover. Preferably, the shroud comprises a sealing device as previously described herein to seal shut the shroud when placed over a VFHCD. In a preferred embodiment, the shroud has a much higher porosity and higher permeability than the fabric component in a VFHCD to allow for unrestricted air low. The shroud may have twice as high air permeability than the fabric component. The shroud may be constructed entirely of mesh except the portion that covers the face shield. The shroud may partially or completely cover the face shield in a VFHCD. The shroud may partially cover the transparent face shield so as to provide privacy, while allowing some light inside the device.

A variable flow head covering device (VFHCD) can be placed in a shroud 1902 where the shroud can also act as a carrying case. The shroud comprising a VFHCD inside may be stored until next use or carried by a user to a different location while protecting the face shield from getting scratched or damaged. In some embodiments, shroud may instead be just a carrying case and not be used for a blackout device. In some embodiments, the carrying case may be comprised of a rigid material. The shroud can serve as a protective cover for the device when not in use.

Smart App for Working with a Variable Flow Head Covering Device (VFHCD)

The following embodiments describes a variable flow head covering device (VFHCD) wherein the electronic functions can be controlled and monitored by a smart app on a smart device. The smart app may be compatible with smart devices, such as smart phones, tablets, and wearables. The smart app may also include natural language processing (NLP) capabilities to allow for hands-free device usage, greater accessibility for individuals with disabilities, convenience, and novelty. The smart app may have augmented reality capabilities. The smart app may include predictive analytics for a more personal and engaging experience based on past movements and activities. The smart app may utilize biometric data, GPS, or other sensory hardware to provide information about the user, their environment, and their location. The smart app can be downloaded onto a mobile device such as a wearable, tablet, laptop, or cell phone. The smart app can be downloaded onto a non-mobile device such as a desk top computer.

Any of the variable flow head covering device (VFHCD) embodiments described herein may be controlled and monitored by an app on a smart device as further previously described herein. The VFHCD may comprise an antenna to receive a wireless signal that is extended from the top of the VFHCD. The extending antenna may be rigid or a flexible whip antenna. In other embodiments, the antenna may be hidden from view within the frame of the VFHCD or under the fabric component. In other embodiments the antenna may be in the form of wires located on the surface of the face shield.

The VFHCD comprises a controller that may include one or more communication systems, including Bluetooth communication chips, Internet Wi-Fi transceivers, network transceivers, a wireless mesh network device such as Z-Wave network transceiver, or a combination thereof to wirelessly communicate with a smart device. The controller may be mounted in the rigid component of the VFHCD. The controller is able to control various components of the VFHCD such as the rate of the air mover, humidity level, temperature, dimming of the face shield using an electrochromic layer, audio visual and communication components such as an image or video display, microphone, or speaker on demand by the user using an app on a smart device. The smart device may be a stand-alone smart device or integrated with the rigid component of the VFHCD. The one or more communication systems may communicate by a wireless signal with at least one of external remote controllers and a cloud-based network in real-time, intermittent time, or in pre-determined time intervals and lengths of time or a combination thereof.

The one or more communication systems may receive instructions from the external remote controller, generate signals instructing components of the VFHCD to operate and to monitor the status of various components. The communications system may generate a signal informing the external remote controller of the status of at least one device in the VFHCD. In an exemplary embodiment, the remote controller is a smart device such as a tablet, wearable, or mobile phone controlled by a user.

The smart device communicates to a plurality of devices within the VFHCD. The smart device may also include a wireless transmitter and wireless transceiver and have a connection to each network device of the one or more devices. The connection may include a wired or wireless interface such as Bluetooth, WIFI, mesh network or similar wireless protocol.

A graphical user interface for monitoring and controlling functions of a variable flow head covering device (VFHCD) with an app may be used. The GUI displayed on a smart device can display various information and multiple indicators and control functions. Information may include time, temperature, weather conditions, battery charge status of the smart device along with the VFHCD battery charge status, whether the VFHCD is plugged in and charging, and variable fan speed indicators. The app may provide an audible alert or a visual alert for the user on the GUI if the battery level goes below a certain level where a limited amount of usage time is left. Touch controls may be provided to control the fan speed, power, or lights inside or outside of the VFHCD.

Other functions and capabilities of a VFHCD may be monitored and controlled by a GUI as previously described herein and illustrated in FIGS. 16-19. Biometric information may be monitored such as body temp, pulse rate (beats per minute (BPM)), breathing rate (breaths per minute (BPM)), blink rate (blinks per minute (BPM)), and oxygen saturation levels (% $O_2$) that are collected by various sensors in the VFHCD. Other biometric data may be displayed such as head orientation, closed eyes, and combinations thereof. The app may be able to store and monitor the biometric data for more than one user. The biometric data can be selectively collected on a user if the designated user is confirmed by a fingerprint or retinal scanner. A VFHCD may further comprise a processor for receiving signals from biometric sensors and communicate biometric information to the smart device, and wherein the app is configured to receive and process biometric information and provide alerts and reports to the user.

The app may provide alerts for information collected by safety sensors in occupational safety applications such as exterior temperature, noise level, or air quality. The app may be configured to control the temperature, air flow, volume inside of the HCD based on the ambient noise levels in occupational and non-occupational settings. Air pressure differences may also be monitored by one or more sensors and relayed to the smart device and displayed by the app.

The app may be configured to provide filter end of useful life alerts to the user based on at least one of age of the filter, increased head pressure on the filter and optical readings indicating a dirty filter.

The invention has been described with reference to various specific and preferred embodiments and techniques. Nevertheless, it is understood that many variations and modifications may be made while remaining within the spirit and scope of the invention.

What is claimed is:

1. An air filtering device comprising: a rigid component comprising a rigid oval-shaped frame, with a top, oval-shaped edge, and a transparent face shield, the transparent face shield having a bottom, oval-shaped edge, the bottom, oval-shaped edge is attached along an entire top, oval-shaped edge of the frame;
    wherein a bottom portion of the oval-shaped frame is configured to pass below the chin of a user and an upper portion of the oval-shaped frame is configured to pass above the user's forehead;
    a substantially air-tight fabric component attached around the entire oval-shaped frame;
    wherein the rigid component and the fabric component are configured to combine to cover an entire head of the user and configured to form a seal around the user's neck;
    an intake port with an inlet filter located on the rigid oval-shaped frame to filter intake air entering the air filtering device;
    an exhaust port with an exhaust filter located on the rigid oval-shaped frame to filter exhaust air exiting the air filtering device;
    an air mover affixed to the oval-shaped frame causing filtered air to enter the intake port from outside the air filtering device and exhaust air to exit the exhaust port; and
    a controller configured to adjust a rate at which the air mover moves air.

2. The air filtering device of claim 1, wherein the controller turns the air mover on when the head covering device is configured to be placed on the head of the user and turns the air mover off when the head covering device is configured to be removed from the head of the user.

3. The air filtering device of claim 2, further comprising a sensor for detecting a proximity of the user's head.

4. The air filtering device of claim 2, further comprising a switch comprising a spring loaded lever that is configured to be depressed when the air filtering device is configured to be placed over the head of the user and turns on the air mover.

5. The air filtering device of claim 1, further comprising two or more electrodes and wherein when the electrodes are configured to come into contact with the skin of the user, the air mover is turned on.

6. The air filtering device of claim 5, wherein the electrodes are located in the fabric component.

7. The air filtering device of claim 1, wherein at least a portion of the transparent face shield comprises a hinge to allow the portion of the transparent face shield to be pivoted away from the user's face, and wherein the air mover is configured to be turned off when the portion of the transparent face shield is pivoted away from the user's face.

8. The air filtering device of claim 1, further comprising a sensor for generating signals indicative of at least one of air pressure, ambient temperature, body temperature, skin moisture, blood oxygen saturation, respiration rate and pulse rate, and a processor for processing signals from the sensor and providing instructions to the controller to adjust the rate of the air mover according to predetermined parameters.

9. The air filtering device of claim 8, wherein the device is configured to communicate with an application running on a user's smart device, wherein the application is configured to provide alerts to the user and to allow the user to adjust the rate of the air mover.

10. The air filtering device of claim 1, further comprising a communication module for receiving signals relating to at least one of air pressure, ambient temperature, body temperature, skin moisture, blood oxygen saturation, respiration rate and pulse rate, and a processor for processing signals from the communication module and providing instructions to the controller to adjust the rate of the air mover according to predetermined parameters.

11. The air filtering device of claim 10, wherein the communication module is configured to receive signals from a user's smart device.

12. The air filtering device of claim 11, wherein the air filtering device is configured to communicate with an application running on the user's smart device, wherein the application is configured to provide alerts to the user and to allow the user to adjust the rate of the air mover.

13. The air filtering device of claim 10, wherein the communication module is configured to receive signals from a user's wearable smart device.

14. The air filtering device of claim 1, further comprising a sensor for generating signals indicative of a concentration of oxygen, and a processor for processing signals from the sensor and providing instructions to the controller to increase the rate of the air mover when the concentration of oxygen falls below a predetermined level.

15. The air filtering device of claim 14, wherein the air filtering device further comprises a user warning system, configured to alert the user when the concentration of oxygen falls below the predetermined level.

16. The air filtering device of claim 1, further comprising a sensor for generating signals indicative of a concentration of carbon dioxide, and a processor for processing signals from the sensor and providing instructions to the controller to increase the rate of the air mover when the concentration of carbon dioxide rises above a predetermined level.

17. The air filtering device of claim 16, wherein the air filtering device further comprises a user warning system, configured to alert the user when the concentration of carbon dioxide rises above the predetermined level.

18. The air filtering device of claim 16, further comprising a second sensor for generating signals indicative of a concentration of oxygen, and wherein the processor processes signals from the sensor and the second sensor and provides instructions to increase the rate of the air mover when either the concentration of carbon dioxide rises above the predetermined level or the concentration of oxygen falls below a second predetermined level.

19. The air filtering device of claim 1, further comprising a privacy shroud to cover the air filtering device to provide a more comfortable sleeping environment for the user.

20. The air filtering device of claim 19, wherein the air filtering device is configured to detect when the privacy shroud is placed over the air filtering device and increase the rate of the air mover in response thereto.

21. The air filtering device of claim 1, wherein the inlet filter and the exhaust filter are different portions of the same filter.

22. The air filtering device of claim 21, wherein the inlet filter portion and the exhaust filter portion are isolated from each other.

* * * * *